United States Patent
Nakagawa et al.

(10) Patent No.: US 6,251,891 B1
(45) Date of Patent: Jun. 26, 2001

(54) CARBAPENEM DERIVATIVES

(75) Inventors: Susumu Nakagawa, Nukata-gun; Norikazu Otake, Tsukuba; Hideo Kiyonaga, Tsukuba; Koji Yamada, Tsukuba; Hideki Jona, Tsukuba; Shigemitsu Okada, Okazaki; Masayuki Ogawa, Osato; Hideaki Imamura, Tsukuba; Ryosuke Ushijima, Okazaki, all of (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/294,091

(22) Filed: Apr. 19, 1999

Related U.S. Application Data

(63) Continuation-in-part of application No. 08/793,891, filed as application No. PCT/JP95/01140 on Jun. 7, 1995, now abandoned.

(30) Foreign Application Priority Data

Sep. 16, 1994  (JP) .................................................. 6-248610

(51) Int. Cl.[7] ..................... C07D 477/20; C07D 519/06; A61K 31/407; A61K 31/4178; A61P 31/04
(52) U.S. Cl. ........................................ 514/210.1; 540/350
(58) Field of Search ........................... 514/210.1; 540/350

(56) References Cited

U.S. PATENT DOCUMENTS 4,997,936  3/1991  Christensen et al. ................. 540/350

FOREIGN PATENT DOCUMENTS

| 0 050 334 | 4/1982 | (EP) . |
| 0 202 048 | 11/1986 | (EP) . |
| 57-175192 | 1/1993 | (JP) . |

OTHER PUBLICATIONS

J. Antimicrobial Chemotherapy 1983 12, Suppl. D, 1–35 Kahan et al Thienamycin: development etc.

Antimicrobial Agents and Chemotherapy 1982 vol. 22, No. 1 pp 62–70 "Kropp et al Metabolism of Thienamycin and Related Carbapenem Antibiotics by the Renal Dipeptidase, Dehydropeptidase–I".

Antimicrobial Agents and Chemotherapy 1983 vol. 23, No. 2 pp 300–307 Norrby et al Urinary Recovery of N–formimidoyl Thienamycin (MK0787) etc.

J. Medicinal Chemistry vol. 22, No. 12 1979 Communications to the Editor Leanza et al "N–Acetimidoyl– and N–formimidoylthienamycin etc."

J. Amer. Chem. Society 100(20) 6299–6548 (1978) Schönberg et al "Structure and Absolute Configuration of Thienamycin".

Primary Examiner—Mark L. Berch
(74) Attorney, Agent, or Firm—Nixon & Vanderhye

(57) ABSTRACT

A compound represented by the general formula

[I]

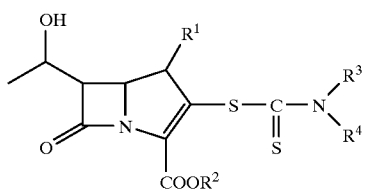

wherein $R^1$ either represents a hydrogen atom or a lower alkyl group, $R^2$ represents a hydrogen atom, an ester residue, an alkali metal or negative charge, and $R^3$ and $R^4$ are the same or different, and each represent a hydrogen atom or a hydrocarbonic group optionally containing hetero atom(s) selected from the group consisting of oxygen atom(s), sulfur atom(s) and nitrogen atom(s), or they are combined together with the nitrogen atom to which they bound to form a heterocyclic group, and the use thereof as an antibacterial agent.

3 Claims, No Drawings

CARBAPENEM DERIVATIVES

This is a continuation-in-part of application Ser. No. 08/793,891, filed Mar. 12, 1997 abandoned which in turn is a national phase entry under 37 U.S.C. §371 of PCT/JP95/01140 filed Jun. 7, 1995.

TECHNICAL FIELD

This invention relates to novel carbapenem (7-oxo-1-azabicyclo[3.2.0]hept-2-en-2-carboxylic acid) compounds, antibacterial agents containing such compounds as active ingredients, and a process for producing such compounds.

BACKGROUND ART

In recent years, new β-lactam antibiotic substances have been found in nature which have the same β-lactam rings as penicillins and as cephalosporins, but which have different basic structures.

For example, naturally derived carbapenem compounds such as thienamycin isolated from the fermentation of *Streptomyces cattleya* (J. Am. Chem. Soc., vol. 100, p. 6491 (1978)), may be mentioned. Thienamycin has an excellent antibacterial spectrum and strong antibacterial activities over a wide range against Gram-positive bacteria and Gram-negative bacteria. Therefore, its development as a highly useful β-lactam agent has been expected. However, thienamycin itself is chemically unstable, and it has been reported that it is likely to be decomposed by a certain enzyme in vivo such as renal dehydropeptidase I (hereinafter referred to simply as DHP-I), whereby the antibacterial activities tend to decrease, and the recovery rate in the urine is low (Antimicrob. Agents Chemother., vol. 22, p. 62 (1982); ibid., vol. 23, p. 300 (1983)).

Merck & Co., Inc. have synthesized many thienamycin analogs with an aim to maintain the excellent antibacterial activities of thienamycin and to secure chemical stability. As a result, imipenem: (5R,6S)-3-[[2-(formimidoylamino)ethyl]thio]-6-[(R)-1-hydroxyethyl]-7-oxo-1-azabicyclo[3.2.0]hept-2-en-2-carboxylic acid monohydrate, obtained by formimidization of the amino group of thienamycin, has been practically developed as a pharmaceutical product (J. Med. Chem., vol. 22, p. 1435 (1979)).

Imipenem has antibacterial activities of an equal or higher level than thienamycin against various types of bacteria and has β-lactamase resistance. Especially against *Pseudomonas aeruginosa*, its antibacterial activities are superior to thienamycin by from 2 to 4 times. Further, the stability of imipenem in the solid form or in an aqueous solution is remarkably improved over thienamycin.

However, like thienamycin, imipenem is decomposed by DHP-I in the human kidney, and therefore, it does not exhibit sufficient treatment effect on urinary-tract infections. Therefore, imipenem can not be administered alone and is required to be used in combination with a DHP-I inhibitor like cilastatin (J. Antimicrob. Chemother., vol. 12 (Suppl. D), p. 1 (1983)). In recent years, imipenem has been frequently used for the treatment and prophylaxis of infectious diseases. Consequently, highly methicillin-resistant *Staphylococcus aureus* which is resistant to imipenem and imipenem resistant *Pseudomonas aeruginosa* are increasing in the clinical field. Imipenem does not show adequate treating effects against these resistant bacteria.

The characteristic of the compounds of the invention is having the partial structure of S—C(=S)N in the substituent at the 2-position of the carbapenem skeleton, and carbapenem compounds having the partial structure are novel compounds not disclosed in literatures. Prior art disclosing or suggesting the invention has not been known at all.

β-Lactam antibiotics exhibit selective toxicity against bacteria and show no substantial effects against animal cells. Therefore, they are widely used for treatment of infectious diseases caused by bacteria, as antibiotics having little side effects, and thus are highly useful drugs.

However, in recent years, highly methicillin-resistant *Staphylococcus aureus* (hereinafter, abbreviated as MRSA), methicillin-resistant coagulase negative Staphylococci (hereinafter, abbreviated as MRCNS) and resistant *Pseudomonas aeruginosa* have been isolated frequently from patients with the immunity decreased, as bacteria causing hardly curable infectious diseases. This has come into a large social problem. Further, recently, the strong toxicity of vancomycin, which is selectively used against MRSA, to the kidney, and the increasing resistance of pathogenic bacteria such as MRSA and MRCNS are becoming clinically serious problems. Accordingly, it is strongly desired to develop an antibacterial agent having improved antibacterial activities against such resistant bacteria, but β-lactam antibacterial agents meeting such requirement have not yet been developed. With respect to carbapenem compounds, it is strongly desired to develop medicaments which have improved antibacterial activities against bacteria causing hardly curable infectious diseases, particularly against MRSA and MRCNS, improved stability against DHP-I, reduced toxicity against the kidney, and no side effect on the central nervous system.

DISCLOSURE OF INVENTION

The present inventors intensely studied aiming to provide novel carbapenem compounds having wide antibacterial spectra and excellent antibacterial activities, and further being DHP-I-resistant. As a result, they found that the carbapenem compounds of the invention either which have, at the 2-position of the carbapenem skeleton, groups represented by the general formula:

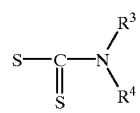

wherein $R^3$ and $R^4$ may be the same or different, and each represent a hydrogen atom or a hydrocarbonic group optionally containing hetero atom(s) selected from the group consisting of oxygen atom(s), sulfur atom(s) and nitrogen atom(s), or they are combined together with the nitrogen atom to which they bound to form a heterocyclic group, or in which the substituent $R^1$ at the 1-position of the carbapenem skeleton is bound to $R^3$ to form a heterocyclic group are novel compounds not disclosed in literatures, and have strong antibacterial activities against a wide range of Gram-positive bacteria and Gram-negative bacteria, and completed the invention.

This invention relates to a compound represented by the general formula:

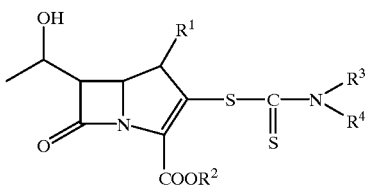

[I]

wherein $R^1$ either represents a hydrogen atom or a lower alkyl group or is bound to $R^3$ to form a heterocyclic group, $R^2$ represents a hydrogen atom, an ester residue, an alkali metal or negative charge, and $R^3$ and $R^4$ are the same or different, and each represent a hydrogen atom or a hydrocarbonic group optionally containing hetero atom(s) selected from the group consisting of oxygen atom(s), sulfur atom(s) and nitrogen atom(s), or they are combined together with the nitrogen atom to which they bound to form a heterocyclic group,
a process for producing the compound and its use as an antibacterial agent.

Explanation is made on symbols and terms mentioned in the present description. The compounds of the invention have a basic structure of the formula:

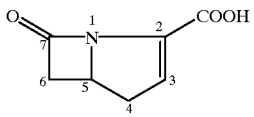

which is systematically referred to as a 7-oxo-1-azabicyclo [3.2.0]hept-2-en-2-carboxylic acid. For the convenience sake, in the description, this basic structure will be referred to as a 1-carbapen-2-em-3-carboxylic acid by putting the numbers based on a commonly widely used carbapenem of the formula:

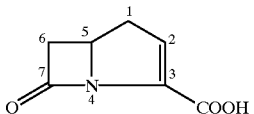

The invention includes optical isomers based on the asymmetrical carbon atoms at the 1-position, 5-position, 6-position and 8-position of the carbapenem structure and stereoisomers. Among these isomers, preferred is a compound of a (5R,6S,8R) configuration i.e. a compound having a steric configuration of (5R,6S) (5,6-trans) like thienamycin and in which the carbon atom at the 8-position takes a R-configuration, or a compound of a (1R,5S,6S,8R) configuration in a case where a methyl group is present at the 1-position.

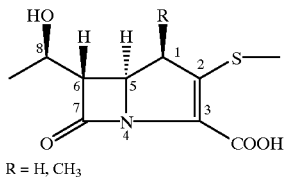

R = H, CH₃

The lower alkyl group means a straight-chain or branched alkyl group having 1 to 6 carbon atoms, and includes, for example, a methyl group, an ethyl group, a propyl group, an isopropyl group, a butyl group, a sec-butyl group, a t-butyl group, a pentyl group, a hexyl group, etc., and preferred among them are a methyl group, an ethyl group, a t-butyl group, etc.

The cyclo-lower alkyl group means a cyclic alkyl group having 3 to 6 carbon atoms, and includes, for example, a cyclopropyl group, a cyclobutyl group, a cyclopentyl group, a cyclohexyl group, etc., and preferred among them are a cyclopropyl group, a cyclobutyl group, etc.

The lower alkenyl group means a straight-chain or branched alkenyl group having 2 to 6 carbon atoms, and includes, for example, a vinyl group, a 1-propenyl group, an allyl group, an isopropenyl group, a 1-butenyl group, a 3-butenyl group, a 1,3-butadienyl group, a 2-pentenyl group, a 4-pentenyl group, a 1-hexenyl group, a 3-hexenyl group, a 5-hexenyl group, etc., and preferred among them are a 1-propenyl group, an allyl group, an isopropenyl group, a 1-butenyl group, etc.

The lower alkynyl group means a straight-chain or branched alkynyl group having 2 to 6 carbon atoms, and includes, for example, a 2-propynyl group, a 2-butynyl group, a 3-butynyl group, a 2-pentynyl group, etc., and preferred among them are a 2-propynyl group, a 2-butynyl group, etc.

The aryl group includes, for example, a phenyl group, a naphthyl group, an anthryl group, a phenanthryl group, etc., and preferred among them are a phenyl group and a naphthyl group.

The aromatic heterocyclic group includes, for example, a thiazolyl group, an isothiazolyl group, an oxazolyl group, an isoxazolyl group, a pyrazolyl group, an imidazolyl group, a triazolyl group, a pyridyl group, a pyrimidinyl group, a pyrazinyl group, a quinolinyl group, an isoquinolinyl group, a benzothiazolyl group, a benzoxazolyl group, a benzopyrazolyl group, a quinoxalinyl group, a benzimidazolyl group, benzotriazolyl group, a thiadiazolyl group, a thienyl group, a furyl group, a tetrazolyl group. etc., and preferred among them are a thiazolyl group, a benzothiazolyl group, a thienyl group, a furyl group, etc.

The aliphatic heterocyclic group means an aliphatic heterocyclic group being a monocyclic ring or a condensed ring composed of 2 or 3 rings, and it can be a saturated aliphatic heterocyclic group or an unsaturated aliphatic heterocyclic group.

Specific examples of the aliphatic heterocyclic group of a monocyclic ring include, for example, heterocyclic groups such as

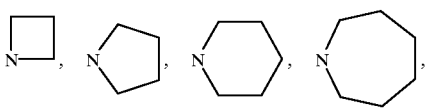

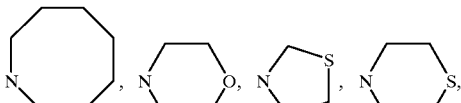

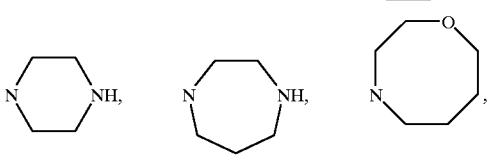

-continued

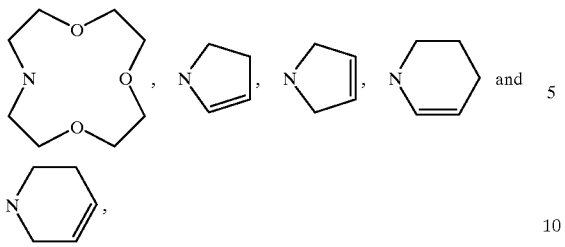

and preferred among them are heterocyclic groups such as, for example,

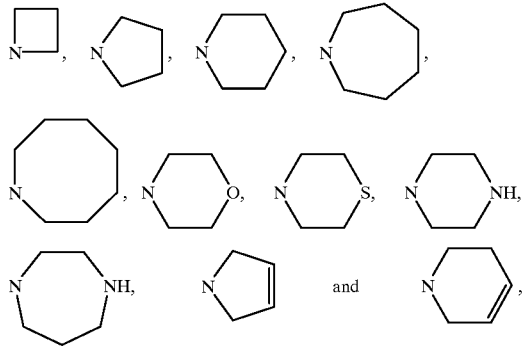

Examples of the aliphatic heterocyclic group being of a condensed ring composed of 2 or 3 rings include heterocyclic groups such as

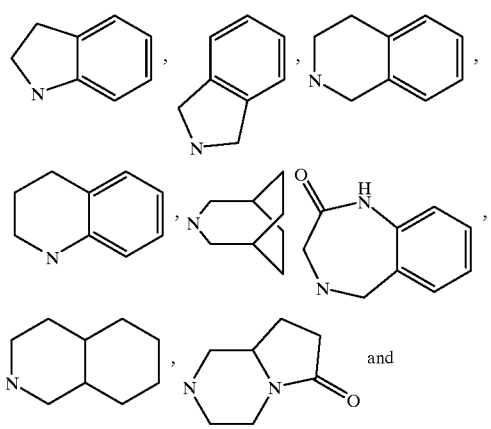

-continued

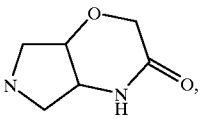

and preferred among them are heterocyclic groups such as, for example,

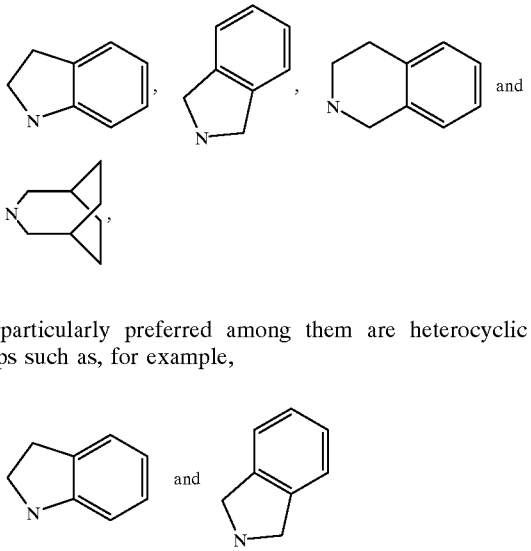

and particularly preferred among them are heterocyclic groups such as, for example,

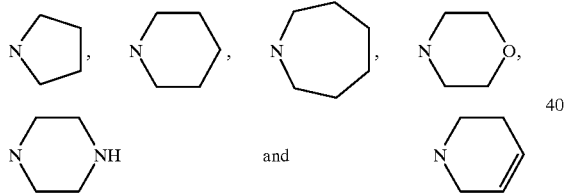

The polycyclic group means a cyclic substituent composed of 2 or 3 rings and optionally containing hetero atom(s), and includes, for example, substituents such as

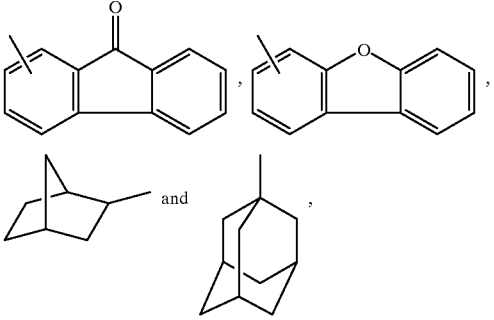

and preferred among them are substituents such as

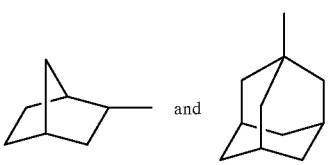

The ester residue includes, for example, alkanoyloxymethyl groups such as an acetoxymethyl group and a pivaloyloxymethyl group, alkoxycarbonyloxyalkyl groups such as a 1-(ethoxycarbonyloxy)ethyl group, a phthalidyl group, (5-substituted-2-oxo-1,3-dioxol-4-yl)methyl groups such as a (5-methyl-2-oxo-1,3-dioxol-4-yl)methyl group, etc.

The alkali metal includes, for example, alkali metals such as sodium and potassium, and preferred among them is sodium.

The hydrocarbonic group optionally containing hetero atom(s) selected from the group consisting of oxygen atom (s), sulfur atom(s) and nitrogen atom(s) means a hydrocarbonic group capable of binding to S—C(=S)N, the partial structure of the 2-position substituent of the carbapenem skeleton which is the characteristic of the invention, and can optionally contain one or plural heterocyclic groups or polycyclic groups, and each of the heterocyclic groups or polycyclic groups can have 1 to 3 substituents. Specifically, the hydrocarbonic group is represented by the formula:

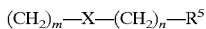

wherein $R^5$ represents a hydrogen atom or a lower alkyl group, cyclo-lower alkyl group, lower alkenyl group, lower alkynyl group, aryl group, aromatic heterocyclic group, aliphatic heterocyclic group or polycyclic group each optionally having substituent(s), X represents a single bond, an oxygen atom, a sulfur atom, a sulfinyl group, a sulfonyl group, $NR^6$, $SO_2NR^6$, $N(R^6)SO_2NR^7$, $N(R^6)SO_2$, $CH(OR^6)$, $CONR^6$, $N(R^6)CO$, $N(R^6)CONR^7$, $N(R^6)COO$, $N(R^6)CSO$, $N(R^6)COS$, $C(R^6)=CR^7$, $C\equiv C$, $CO$, $CS$, $OC(O)$, $OC(O)NR^6$, $OC(S)NR^6$, $SC(O)$, $SC(O)NR^6$ or $C(O)O$ (wherein $R^6$ and $R^7$ each represent a hydrogen atom or an optionally substituted lower alkyl group), and m and n are the same or different and each represent an integer of 0 to 10. Preferred among them are hydrocarbonic groups wherein $R^5$ is a lower alkyl group, cyclo-lower alkyl group, lower alkenyl group, aryl group, aromatic heterocyclic group or aliphatic heterocyclic group each optionally having substituent(s), X is a single bond, an oxygen atom, a sulfur atom, a sulfinyl group, a sulfonyl group, $NR^6$, $SO_2$, $NR^6$, $N(R^6)SO_2NR^7$, $N(R^6)SO_2$, $CH(OR^6)$, $CONR^6$, $N(R^6)CO$, $N(R^6)CONR^7$ or $N(R^6)COO$ (wherein $R^6$ and $R^7$ each represent a hydrogen atom or an optionally substituted lower alkyl group), and m and n each are 0 to 4, and particularly preferred among them are hydrocarbonic groups wherein $R^5$ is a lower alkyl group or lower alkenyl group each optionally having substituent(s), X is a single bond, an oxygen atom, a sulfur atom, $NR^6$, $CONR^6$ or $N(R^6)CO$ (wherein $R^6$ and $R^7$ each represent a hydrogen atom or an optionally substituted lower alkyl group), and m and n each are 0 to 2.

The heterocyclic group which is formed when $R^3$ and $R^4$ are combined together with the nitrogen atom to which they bound means a saturated or unsaturated 3 to 14-membered monocyclic ring or a saturated or unsaturated 3 to 14-membered condensed ring or assembled ring composed of 2 or 3 rings, wherein nitrogen atom(s) may be quaternary and which may have substituent(s). The heterocyclic group is a heterocyclic group capable of being formed together with S—C(=S)N, the partial structure of the 2-position substituent of the carbapenem skeleton which is the characteristic of the invention, and can further have 1 to 3 substituents.

As specific examples of the monocyclic ring and the condensed ring composed of 2 or 3 rings, there can be mentioned aliphatic heterocyclic groups being the aforesaid monocyclic rings or the condensed rings each being composed of 2 or 3 rings.

The assembled ring composed of 2 or 3 rings means a heterocyclic group having 2 or 3 rings formed when the heterocyclic group formed when $R^3$ and $R^4$ are combined together with the nitrogen atom to which they bound is combined with another substituent having 1 or 2 cyclic structures. Specific examples of the assembled ring include substituents such as, for example,

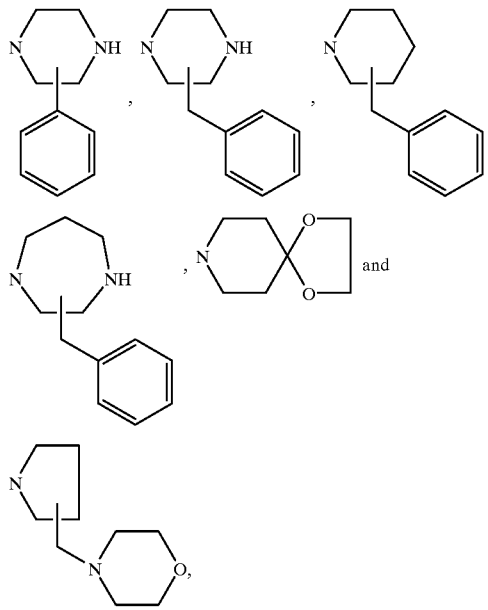

and preferred among them are substituents such as, for example,

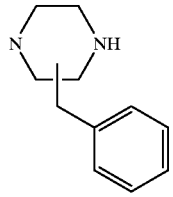

The carboxyl-protecting group includes lower alkyl groups such as, for example, a methyl group, an ethyl group, a propyl group, an isopropyl group and t-butyl group; halo-substituted lower alkyl groups such as, for example, a 2,2,2-trichloroethyl group and a 2,2,2-trifluoroethyl group; lower alkanoyloxyalkyl groups such as, for example, an acetoxymethyl group, a propionyloxymethyl group, a pivaloyloxymethyl group, a 1-acetoxyethyl group and a 1-propionyloxyethyl group; lower alkoxycarbonyloxyalkyl groups such as, for example, a 1-(methoxycarbonyloxy) ethyl group, a 1-(ethoxycarbonyloxy)ethyl group and a 1-(isopropoxycarbonyloxy)ethyl group; lower alkenyl groups such as, for example, a 2-propenyl group, a 2-chloro-2-propenyl group, a 3-methoxycarbonyl-2-propenyl group, a 2-methyl-2-propenyl group, a 2-butenyl group and a cinnamyl group; aralkyl groups such as, for example, a benzyl group, a p-methoxybenzyl group, a 3,4-dimethoxybenzyl group, an o-nitrobenzyl group, a p-nitrobenzyl group, a benzhydryl group and a bis(p-methoxyphenyl)methyl group; (5-substituted-2-oxo-1,3-dioxol-4-yl)methyl groups such as, for example, a (5-methyl-2-oxo-1,3-dioxol-4-yl)methyl group; lower alkylsilyl groups such as, for example, a trimethylsilyl group and a t-butyldimethylsilyl group; an indanyl group, a phthalidyl group and a methoxymethyl group, etc., and particularly preferred among them are a 2-propenyl group, a p-nitrobenzyl group, a p-methoxybenzyl group, a benzhydryl group, a t-butyldimethylsilyl group, etc.

The hydroxyl-protecting group includes lower alkylsilyl groups such as, for example, a trimethylsilyl group and a t-butyldimethylsilyl group; lower alkoxymethyl groups such as, for example, a methoxymethyl group and a 2-methoxyethoxymethyl group; for example a tetrahydropyranyl group; aralkyl groups such as, for example, a benzyl group, a p-methoxybenzyl group, a 2,4-dimethoxybenzyl group, an o-nitrobenzyl group, a p-nitrobenzyl group and a trityl group; acyl groups such as, for example, a formyl group and an acetyl group; lower alkoxycaronyl groups such as, for example, a t-butoxycarbonyl group, a 2-iodoethoxycarbonyl group and a 2,2,2-trichloroethoxycarbonyl group; alkenyloxycarbonyl groups such as, for example, a 2-propenyloxycarbonyl group, a 2-chloro-2-propenyloxycarbonyl group, a 3-methoxycarbonyl-2-propenyloxycarbonyl group, a 2-methyl-2-propenyloxycarbonyl group, a 2-butenyloxycarbonyl group and a cinnamyloxycarbonyl group; aralkyloxycarbonyl groups such as, for example, a benzyloxycarbonyl group, a p-methoxybenzyloxycarbonyl group, an o-nitrobenzyloxycarbonyl group and a p-nitrobenzyloxycarbonyl group; etc., and particularly preferred among them are a 2-propenyloxycarbonyl group, a p-nitrobenzyloxycabonyl group, a t-butyldimethylsilyl group, etc.

The amino-protecting group includes aralkylidene groups such as, for example, a benzylidene group, a p-chlorobenzylidene group, a p-nitrobenzylidene group, a salicylidene group, an α-naphthylidene group and a β-naphthylidene group; aralkyl groups such as, for example, a benzyl group, a p-methoxybenzyl group, a 3,4-dimethoxybenzyl group, an o-nitrobenzyl group, a p-nitrobenzyl group, a bezhydryl group, a bis(p-methoxyphenyl)methyl group and a trityl group; lower alkanoyl groups such as, for example, a formyl group, an acetyl group, a propionyl group, a butyryl group, an oxalyl group, a succinyl group and a pivaloyl group; halo-substituted lower alkanoyl groups such as, for example, a chloroacetyl group, a dichloroacetyl group, a trichloroacetyl group and a trifluoroacetyl group; arylalkanoyl groups such as, for example, a phenylacetyl group and a phenoxyacetyl group; lower alkoxycarbonyl groups such as, for example, a methoxycarbonyl group, an ethoxycarbonyl group, a propoxycarbonyl group and a t-butoxycarbonyl group; halo-substituted lower alkoxycarbonyl groups such as, for example, a 2-iodoethoxycarbonyl group and a 2,2,2-trichloroethoxycarbonyl group; alkenyloxycarbonyl groups such as, for example, a 2-propenyloxycarbonyl group, a 2-chloro-2-propenyloxycarbonyl group, a 3-methoxycarbonyl-2-propenyloxycarbonyl group, a 2-methyl-2-propenyloxycarbonyl group, a 2-butenyloxycarbonyl group and a cinnamyloxycarbonyl group; aralkyloxycarbonyl groups such as, for example, a benzyloxycarbonyl group, an o-nitrobenzyloxycarbonyl group, a p-nitrobenzyloxycarbonyl group and a phenethyloxycarbonyl group; lower alkylsilyl groups such as, for example, a trimethylsilyl group and a t-butyldimethylsilyl group; etc., and particularly preferred among them are a 2-propenyloxycarbonyl group, a t-butoxycarbonyl group, a p-nitrobenzyloxycarbonyl group, etc.

$R^1$ either represents a hydrogen atom or a lower alkyl group, or can form a heterocyclic group by binding to $R^3$. The heterocyclic group or polycyclic group is a saturated or unsaturated 6 to 14-membered monocyclic ring or condensed ring composed of 2 or 3 rings, wherein nitrogen atom(s) may be made quaternary, and can have the same or different 1 to 3 later-described substituents designated $R^3$.

$R^2$ represents a hydrogen atom, an ester residue, an alkali metal or negative charge, and when $R^2$ is negative charge, it forms an ion pair with the ammonio group on the hydrocarbonic group or the heterocyclic group.

$R^3$ and $R^4$ are the same or different, and each represent a hydrogen atom or a hydrocarbonic group optionally containing hetero atom(s) selected from the group consisting of oxygen atom(s), sulfur atom(s) and nitrogen atom(s), or they are combined together with the nitrogen atom to which they bound to form a heterocyclic group.

The hydrocarbonic group is not particularly limited so long as it is a hydrocarbonic group capable of binding to the divalent group SC(=S)N, the partial structure of the 2-position substituent of the carbapenem skeleton which is the characteristic of the invention, but it can optionally contain 1 or plural heterocyclic groups, and the each of the heterocyclic groups can contain 1 to 3 substituents designated $R^3$. Specifically, there can be mentioned hydrocarbonic groups represented by the formula:

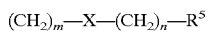

$(CH_2)_m-X-(CH_2)_n-R^5$ wherein $R^5$ represents a hydrogen atom, or a lower alkyl group, cyclo-lower alkyl group, lower alkenyl group, lower alkynyl group, aryl group, aromatic heterocyclic group, aliphatic heterocyclic group or polycyclic group each optionally having substituent(s), x represents a single bond, an oxygen atom, a sulfur atom, a sulfinyl group, a sulfonyl group, $NR^6$, $SO_2NR^6$, $N(R^6)SO_2NR^7$, $N(R^6)SO_2$, $CH(OR^6)$, $CONR^6$, $N(R^6)CO$, $N(R^6)CONR^7$, $N(R^6)COO$, $N(R^6)CSO$, $N(R^6)COS$, $C(R^6)=CR^7$, C≡C, CO, CS, OC(O), $OC(O)NR^6$, $OC(S)NR^6$, SC(O), $SC(O)NR^6$ or C(O)O (wherein $R^6$ and $R^7$ each represent a hydrogen atom or an optionally substituted lower alkyl group), and m and n are the same or different and each represent an integer of 0 to 10. Preferred among them are hydrocarbonic groups wherein $R^5$ is a lower alkyl group, cyclo-lower alkyl group, lower alkenyl group, aryl group, aromatic heterocyclic group or aliphatic heterocyclic group each optionally having substituent(s), x represents a single bond, an oxygen atom, a sulfur atom, a sulfinyl group, a sulfonyl group, $NR^6$, $SO_2NR^6$, $N(R^6)SO_2NR^7$, $N(R^6)SO_2$, $CH(OR^6)$, $CONR^6$, $N(R^6)CO$, $N(R^6)CONR^7$ or $N(R^6)COO$ (wherein $R^6$ and $R^7$ each represent a hydrogen atom or an optionally substituted lower alkyl group), and m and n each are 0 to 4, and particularly preferred among them are hydrocarbonic groups wherein $R^5$ is a lower alkyl group or lower alkenyl group each optionally having substituent(s), X represents a single bond, an oxygen atom, a sulfur atom, $NR^6$, $CONR^6$ or $N(R^6)CO$ (wherein $R^6$ and $R^7$ each represent a hydrogen atom or an optionally substituted lower alkyl group), and m and n each are 0 to 2.

$R^6$ and $R^7$ are the same or different and each represent a hydrogen atom or an optionally substituted lower alkyl group, and the substituent includes a hydroxyl group, a methoxy group, an amino group, a nitro group, a cyano group, a carbamoyl group, a carbamoyloxy group, a formyl group, a hydrazylcarbonyloxy group, a sulfamoyl group, a trifluoromethyl group, a carboxyl group, a sulfo group, etc. Among them, as preferred examples of $R^6$ and $R^7$, there can be mentioned a hydrogen atom, a methyl group, an ethyl group, a propyl group, etc., and as preferred examples of their substituents, there can be mentioned a hydroxyl group, an amino group, a carbamoyl group, etc.

The substituent(s) of the hydrocarbonic group can be located at any position(s) of the hydrocarbonic group so long as it(they) can be substituted. Specific examples of the substituent(s) include, for example, lower alkyl groups such as a methyl group, a hydroxyl group, a cyano group, hydroxy-lower alkyl groups such as a hydroxymethyl group, a carboxyl group, lower alkoxycarbonyl groups such as a methoxycarbonyl group, a carbamoyl group, N-lower alkylcarbamoyl groups such as an N-methylcarbamoyl group, N,N-dilower alkylcarbamoyl groups such as an N,N-dimethylcarbamoyl group, a carbamoyloxy group, N-lower alkylcarbamoyloxy groups such as an N-methylcarbamoyloxy group, N,N-dilower alkylcarbamoyloxy groups such as an N,N-dimethylcarbamoyloxy group, an amino group, N-lower alkylamino groups such as an N-methylamino group, N,N-dilower alkylamino groups such as an N,N-dimethylamino group, N,N,N-triloweralkylammonio groups such as an N,N,N-trimethylammonio group, amino-lower alkyl groups such as an aminomethyl group, N-lower alkylamino lower alkyl groups such as an N-methylaminomethyl group, N,N-dilower alkylamino-lower alkyl groups such as an N,N-dimethylaminomethyl group, N,N,N-triloweralkylammonio-lower alkyl groups such as an N,N,N-trimethylammoniomethyl group, lower alkanoylamino groups such as an acetylamino group, aroylamino groups such as a benzoylamino group, lower alkanoylamidino-lower alkyl groups such as an acetoamidinomethyl group, lower alkylsulfonylamino groups such as a methanesulfonylamino group, N,N-dilower alkyl-N-hydroxy-lower alkylammonio-lower alkyl groups such as an N,N-dimethyl-N-hydroxypropylammoniomethyl group, N,N-dilower alkyl-N-dilower alkylamino-lower alkylammonio-lower alkyl groups such as an N,N-dimethyl-N-dimethylaminoethylammoniomethyl group, a hydroxyimino group, lower alkoxyimino groups such as a methoxyimino group, groups:

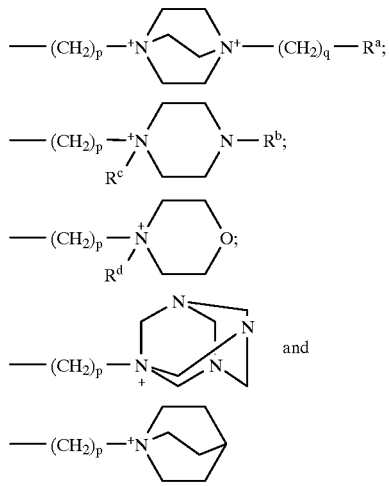

wherein $R^a$ represents a hydroxyl group or a carbamoyl group, $R^b$ represents a lower alkyl group, a formyl group or a lower alkanoyl group, $R^c$ and $R^d$ are the same or different and each represent a lower alkyl group, and p and q are the same or different and each represent 0 to 4, etc., and preferred among them are, for example, a hydroxyl group, a cyano group, hydroxy-lower alkyl groups such as a hydroxymethyl group, a carboxyl group, lower alkoxycarbonyl groups such as a methoxycarbonyl group, a carbamoyl group, N-lower alkylcarbamoyl groups such as an N-methylcarbamoyl group, N,N-dilower alkylcarbamoyl groups such as an N,N-dimethylcarbamoyl group, a carbamoyloxy group, an amino group, N-lower alkylamino groups such as an N-methylamino group, N,N-dilower alkylamino groups such as an N,N-dimethylamino group, N,N,N-triloweralkylammonio groups such as an N,N,N-trimethylammonio group, amino-lower alkyl groups such as an aminomethyl group, lower alkanoylamidino-lower alkyl groups such as an acetoamidinomethyl group, a group:

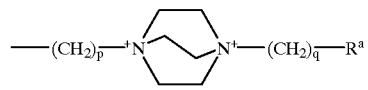

wherein $R^a$ represents a hydroxyl group or a carbamoyl group, and p and q are the same or different and each represent 0 to 4, etc., and particularly preferred are, for example, a hydroxyl group, a cyano group, hydroxy-lower alkyl groups such as a hydroxymethyl group, a carbamoyl group, an amino group, N-lower alkylamino groups such as an N-methylamino group, amino-lower alkyl groups such as an aminomethyl group, a group:

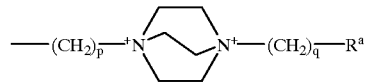

wherein $R^a$ represents a hydroxyl group or a carbamoyl group, and p and q are the same or different and each represent 0 to 4, etc.

When $R^5$ is polycyclic group, specific examples thereof include, for example, substituents such as

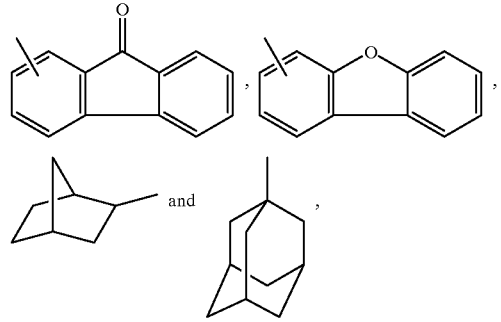

and preferred among them are substituents such as

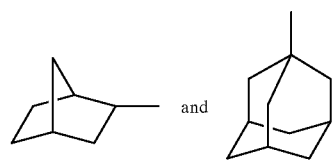

$R^3$ and $R^4$ can combine together with the nitrogen atom to which they are bound to form a heterocyclic group.

The heterocyclic group means a saturated or unsaturated 3 to 14-membered monocyclic ring or a saturated or unsaturated 3 to 14-membered condensed ring or assembled ring composed of 2 or 3 rings, wherein nitrogen atom(s) may be quaternqry. The heterocyclic group is not particularly limited so long as it is a heterocyclic group capable of being formed together with S—C(=S)N, a partial structure of the 2-position substituent of the carbapenem skeleton which is the characteristic of the invention, and can further have 1 to 3 substituents designated $R^3$.

Specific examples of monocyclic aliphatic heterocyclic groups among the heterocyclic groups include heterocyclic groups such as, for example,

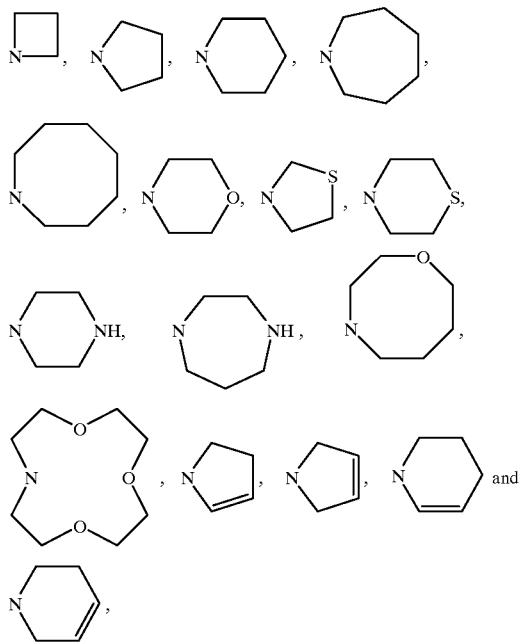

and preferred among them are heterocyclic groups such as, for example,

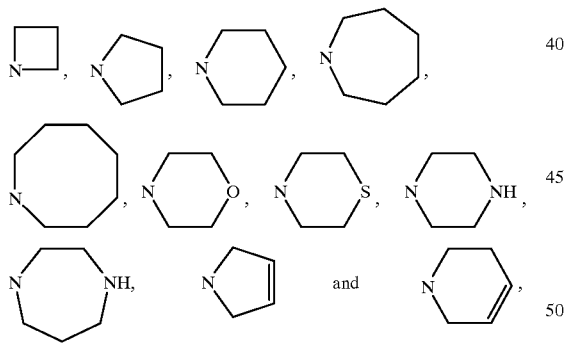

and particularly preferred among them are heterocyclic groups such as, for example,

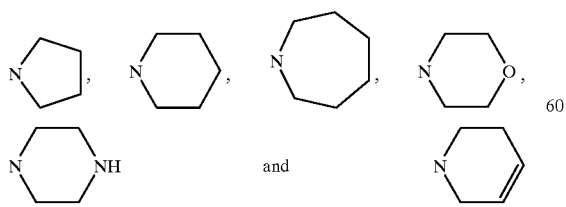

The substituent(s) of such a monocyclic saturated aliphatic heterocyclic group can bind to any of the positions of the heterocyclic group so long as it is a position capable of being substituted. Specific examples of the substituents include, for example, lower alkyl groups such as a methyl group, a hydroxyl group, a lower alkoxy group, hydroxy-lower alkyl groups such as a hydroxymethyl group, a carboxyl group, a carbamoyl group, N-lower alkylcarbamoyl groups such as an N-methylcarbamoyl group, N,N-dilower alkylcarbamoyl groups such as an N,N-dimethylcarbamoyl group, an amino group, N-lower alkylamino groups such as an N-methylamino group, N,N-dilower alkylamino groups such as an N,N-dimethylamino group, N,N,N-trilower alkylammonio groups such as an N,N,N-trimethylammonio group, amino-lower alkyl groups such as an aminomethyl group, N-lower alkylamino-lower alkyl groups such as an N-methylaminomethyl group, N,N-dilower alkylamino lower alkyl groups such as an N,N-dimethylaminomethyl group, N,N,N-trilower alkylammonio-lower alkyl groups such as an N,N,N-trimethylammoniomethyl group, lower alkanoylamino groups such as an acetylamino group, aroylamino groups such as a benzoylamino group, lower alkylsulfonylamino groups such as a methanesulfonylamino group, lower alkylthio-lower alkyl groups such as a methylthiomethyl group, lower alkylsulfonyl-lower alkyl groups such as a methanesulfonylmethyl group, lower alkylsulfinyl-lower alkyl groups such as a methylsulfinylmethyl group, a hydroxyimino group, lower alkoxyimino groups such as a methoxyimino group, an oxo group, a formyl group, lower alkanoyl groups such as an acetyl group, carbamoyl-lower alkylcarbonyl groups such as a carbamoylethylcarbonyl group, amino-lower alkylcarbonyl groups such as an aminomethylcarbonyl group, carboxy-lower alkylcarbonyl groups such as a carboxyethylcarbonyl group, N-lower alkylamino-lower alkylcarbonyl groups such as an N-methylaminomethylcarbonyl group, N,N-dilower alkylamino-lower alkylcarbonyl groups such as an N,N-dimethylaminomethylcarbonyl group, N,N,N-triloweralkylammonio-lower alkylcarbonyl groups such as an N,N,N-trimethylammoniomethylcarbonyl group, hydroxy-lower alkylcarbonyl groups such as a hydroxymethylcarbonyl group, groups:

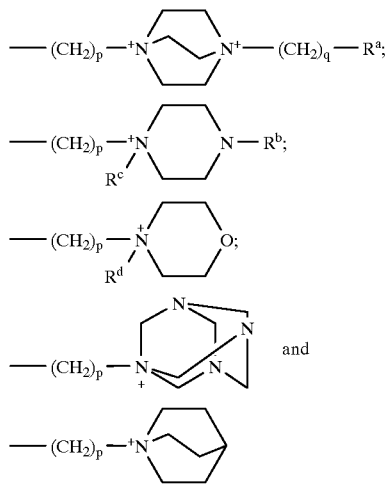

wherein $R^a$ represents a hydroxyl group or a carbamoyl group, $R^b$ represents a lower alkyl group, a formyl group or a lower alkanoyl group, $R^c$ and $R^d$ are the same or different and each represent a lower alkyl group, and p and q are the same or different and each represent 0 to 4, etc., and preferred among them are lower alkyl groups such as a methyl group, a hydroxyl group, lower alkoxy groups, hydroxy-lower alkyl groups such as a hydroxymethyl group, a carboxyl group, a carbamoyl group, an amino group, N-lower alkylamino lower alkyl groups such as an N-methylaminomethyl group, N,N-dilower alkylamino-lower alkyl groups such as an N,N-dimethylaminomethyl group, N,N,N-triloweralkylammonio-lower alkyl groups such as an N,N,N-trimethylammoniomethyl group, lower alkanoylamino groups such as an acetylamino group, lower alkylsulfonylaminogroups such as a methanesulfonylamino group, a hydroxyimino group, lower alkoxyimino groups such as a methoxyimino group, an oxo group, lower alkanoyl groups such as an acetyl group, amino-lower alkylcarbonyl groups such as an aminomethylcarbonyl group, carboxy-lower alkycarbonyl groups such as a carboxyethylcarbonyl group, N-lower alkylamino-lower alkylcarbonyl groups such as an N-methylaminomethylcarbonyl group, N,N-dilower alkylamino-lower alkylcarbonyl groups such as an N,N-dimethylaminomethylcarbonyl group, N,N,N-trilower alkylammonio-lower alkylcarbonyl groups such as an N,N,N-trimethylammoniomethylcarbonyl group, hydroxy-lower alkylcarbonyl groups such as a hydroxymethylcarbonyl group, a group:

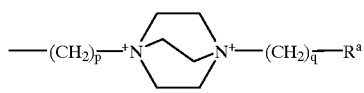

wherein $R^a$ represents a hydroxyl group or a carbamoyl group, and p and q are the same or different and each represent 0 to 4, etc., and particularly preferred are, for example, lower alkyl groups such as a methyl group, a hydroxyl group, a hydroxyimino group, lower alkoxyimino groups such as a methoxyimino group, amino-lower alkylcarbonyl groups such as an aminomethylcarbonyl group, N-lower alkylamino-lower alkylcarbonyl groups such as an N-methylaminomethylcarbonyl group, N,N-dilower alkylamino-lower alkylcarbonyl groups such as an N,N-dimethylaminomethylcarbonyl group, a group:

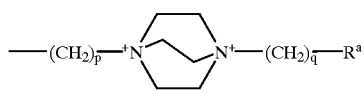

wherein $R^a$ represents a hydroxyl group or a carbamoyl group, and p and q are the same or different and each represent 0 to 4, etc.

The monocyclic unsaturated aliphatic heterocyclic group can be monosubstituted or disubstituted with the same or different substituent(s) at any position(s) so long as the position(s) can be substituted. Specific examples of the substituent(s) include, for example, a hydrogen atom, halogen atoms such as a chlorine atom and a bromine atom, lower alkoxy groups such as a methoxy group, lower alkyl groups such as a methyl group, a carbamoyl group, carbamoyl-lower alkyl groups such as a carbamoylmethyl group, amino-lower alkyl groups such as an aminomethyl group, N-lower alkylamino-lower alkyl groups such as an N-methylaminomethyl group, N,N-dilower alkylamino-lower alkyl groups such as an N,N-dimethylaminomethyl group, N,N,N-trilower alkylammonio-lower alkyl groups such as an N,N,N-trimethylammoniomethyl group, pyridinio-lower alkyl groups such as a pyridiniomethyl group, hydroxy-lower alkyl groups such as a hydroxymethyl group, groups:

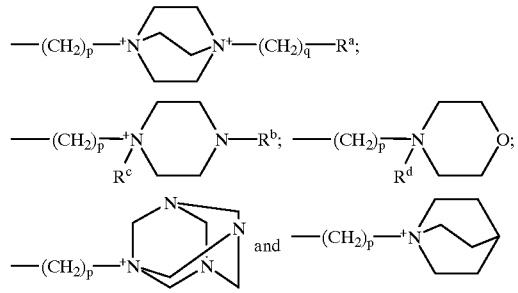

wherein $R^a$ represents a hydroxyl group or a carbamoyl group, $R^b$ represents a lower alkyl group, a formyl group or a lower alkanoyl group, $R^c$ and $R^d$ are the same or different and each represent a lower alkyl group, and p and q are the same or different and each represent 0 to 4, etc., and preferred among them are halogen atoms such as a chlorine atom and a bromine atom, carbamoyl-lower alkyl groups such as a carbamoylmethyl group, amino-lower alkyl groups such as an aminomethyl group, N,N,N-trilower alkylammonio-lower alkyl groups such as an N,N,N-trimethylammoniomethyl group, hydroxy-lower alkyl groups such as a hydroxymethyl group, a group:

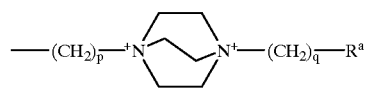

wherein $R^a$ represents a hydroxyl group or a carbamoyl group, and p and q are the same or different and each represent 0 to 4, etc., and particularly preferred are, for example, amino-lower alkyl groups such as an aminomethyl group, hydroxy-lower alkyl groups such as a hydroxymethyl group, a group:

wherein $R^a$ represents a hydroxyl group or a carbamoyl group, and p and q are the same or different and each represent 0 to 4, etc.

The condensed ring composed of 2 or 3 rings include heterocyclic groups such as, for example,

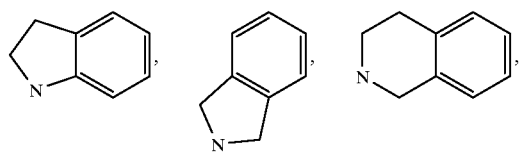

-continued

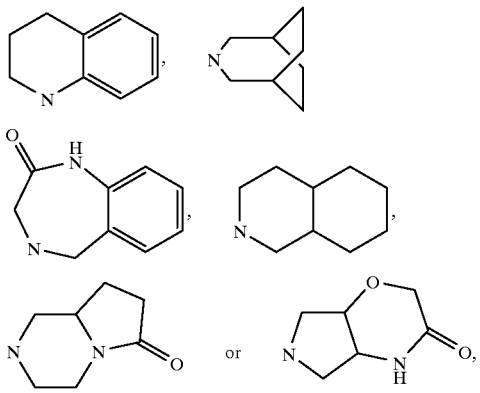

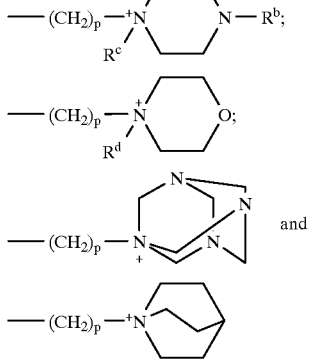

and preferred among them are heterocyclic groups such as, for example,

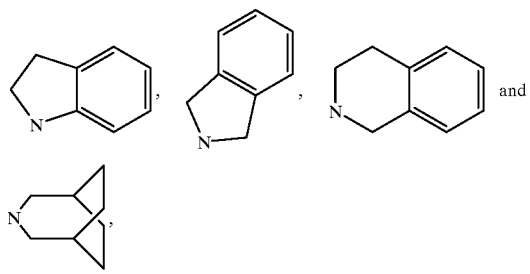

and particularly preferred are heterocyclic groups such as, for example,

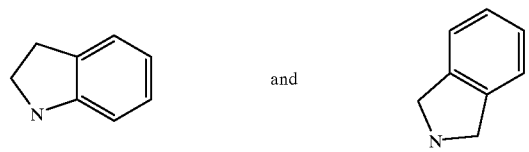

The condensed ring composed of 2 or 3 rings can be monosubstituted or disubstituted with the same or different substituents at any position(s) so long as the position(s) can be substituted. Specific examples of the substituents include, for example, a hydrogen atom, halogen atoms such as a chlorine atom and a bromine atom, lower alkoxy groups such as a methoxy group, lower alkyl groups such as a methyl group, a carbamoyl group, carbamoyl-lower alkyl groups such as a carbamoylmethyl group, amino-lower alkyl groups such as an aminomethyl group, N-lower alkylamino-lower alkyl groups such as an N-methylaminomethyl group, N,N-dilower alkylamino-lower alkyl groups such as an N,N-dimethylaminomethyl group, N,N,N-trilower alkylammonio-lower alkyl groups such as an N,N,N-trimethylammoniomethyl group, pyridinio-lower alkyl groups such as a pyridiniomethyl group, hydroxy-lower alkyl groups such as a hydroxymethyl group, groups:

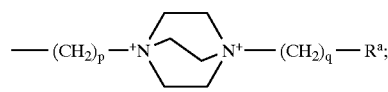

-continued

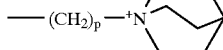

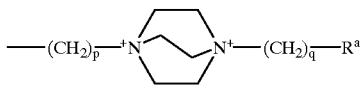

wherein $R^a$ represents a hydroxyl group or a carbamoyl group, $R^b$ represents a lower alkyl group, a formyl group or a lower alkanoyl group, $R^c$ and $R^d$ are the same or different and each represent a lower alkyl group, and p and q are the same or different and each represent 0 to 4, etc., and preferred among them are halogen atoms such as a chlorine atom and a bromine atom, lower alkyl groups such as a methyl group, carbamoyl-lower alkyl groups such as a carbamoylmethyl group, N-lower alkylamino-lower alkyl groups such as an N-methylaminomethyl group, a group:

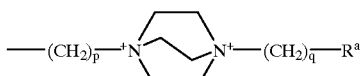

wherein $R^a$ represents a hydroxyl group or a carbamoyl group, and p and q are the same or different and each represent 0 to 4, etc., and particularly preferred are lower alkyl groups such as a methyl group, a group:

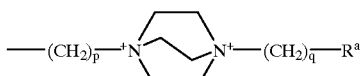

wherein $R^a$ represents a hydroxyl group or a carbamoyl group, and p and q are the same or different and each represent 0 to 4, etc.

The assembled ring composed of 2 or 3 rings means a heterocyclic group having 2 or 3 rings formed when the heterocyclic group formed when $R^3$ and $R^4$ are combined together with the nitrogen atom to which they bound is combined with another substituent having 1 or 2 cyclic structures. Specific examples of the assembled ring include, for example,

3

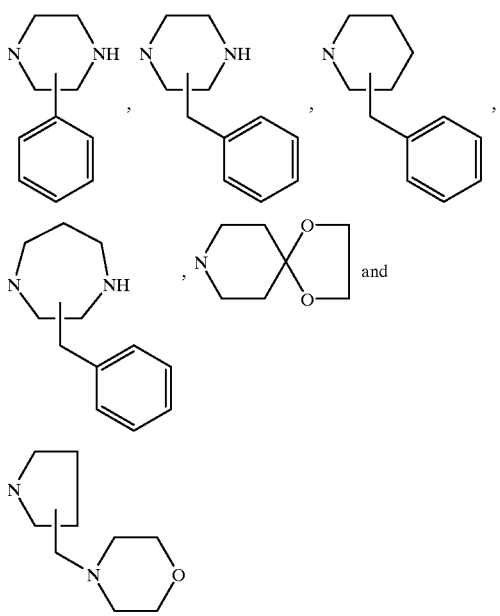

etc., and preferred among them are

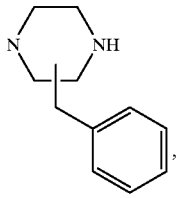

etc.

The assembled ring composed of 2 or 3 rings can be substituted at any position(s) of the heterocyclic group so long as the position(s) can be substituted. Specific examples of the substituent(s) include, for example, lower alkyl groups such as a methyl group, a hydroxyl group, hydroxy-lower alkyl groups such as a hydroxymethyl group, a carbamoyl group, N-lower alkylcarbamoyl groups such as an N-methylcarbamoyl group, N,N-dilower alkylcarbamoyl groups such as an N,N-dimethylcarbamoyl group, an amino group, N-lower alkylamino groups such as an N-methylamino group, N,N-dilower alkylamino groups such as an N,N-dimethylamino group, N,N,N-trilower alkylammonio groups such as an N,N,N-trimethylammonio group, amino-lower alkyl groups such as an aminomethyl group, N-lower alkylamino-lower alkyl groups such as an N-methylaminomethyl group, lower alkanoylamino groups such as an acetylamino group, aroylamino groups such as a benzoylamino group, lower alkylsulfonylamino groups such as a methanesulfonylamino group, etc., and preferred among them are a carbamoyl group, an amino group, N-lower alkylamino-lower alkyl groups, etc.

$R^5$ represents a hydrogen atom, or a lower alkyl group, cyclo-lower alkyl group, lower alkenyl group, lower alkynyl group, aryl group, aromatic heterocyclic group, aliphatic heterocyclic group or a polycyclic group each optionally having substituent(s), and preferred examples of $R^5$ include lower alkyl groups, cyclo-lower alkyl groups, lower alkenyl groups, aryl groups, aromatic heterocyclic groups, aliphatic heterocyclic groups, etc. each optionally having substituent (s), and particularly preferred among them are lower alkyl groups and lower alkenyl groups, each optionally having substituent(s).

As the substituents, the aforesaid substituents of the hydrocarbonic group can be exemplified, but it is also possible to use substituents such as, for example, halogen atoms (a fluorine atom, a chlorine atom, a bromine atom, an iodine atom, etc.), a trifluoromethyl group, an azido group, a nitro group, $SR^6$, $COR^6$, $N(R^6)CHO$, $COOR^6$, $SO_2N(R^6)R^7$, $CSN(R^6)R^7$, $SC(S)N(R^6)R^7$, cyclo-lower alkyl groups, optionally substituted lower alkenyl groups, optionally substituted lower alkynyl groups and groups:

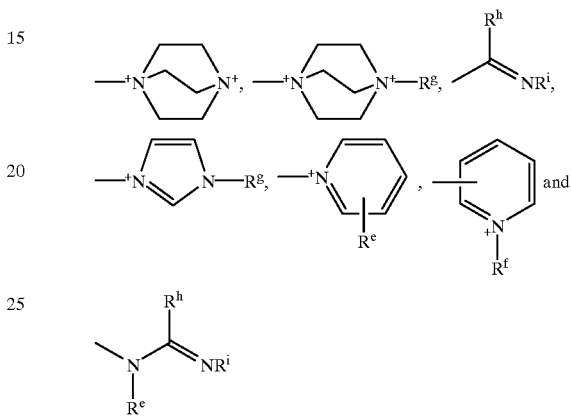

wherein $R^e$, $R^f$, $R^g$ and $R^h$ are the same or different, and each represent a hydrogen atom, or a lower alkyl group, cyclo-lower alkyl group, lower alkenyl group, lower alkynyl group, aryl group, aromatic heterocyclic group or aliphatic heterocyclic group each optionally having substituent(s), $R^i$ represents a hydrogen atom, or a lower alkyl group or cyclo-lower alkyl group each optionally having substituent(s).

Preferred examples of the substituents include, for example, a hydroxyl group, a cyano group, hydroxy-lower alkyl groups such as a hydroxymethyl group, a carboxyl group, lower alkoxycarbonyl groups such as a methoxycarbonyl group, a carbamoyl group, N-lower alkylcarbamoyl groups such as an N-methylcarbamoyl group, N,N-dilower alkylcarbamoyl groups such as an N,N-dimethylcarbamoyl group, a carbamoyloxy group, an amino group, N-lower alkylamino groups such as an N-methylamino group, N,N-dilower alkylamino groups such as an N,N-dimethylamino group, N,N,N-trilower alkylammonio groups such as an N,N,N-trimethylammonio group, amino-lower alkyl groups such as an aminomethyl group, lower alkanoylamidino-lower alkyl groups such as an acetamidinomethyl group, a group:

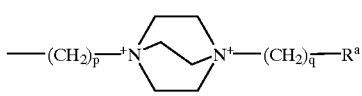

wherein $R^a$ represents a hydroxyl group or a carbamoyl group, and p and q are the same or different and each represent 0 to 4, etc., and particularly preferred are, for example, a hydroxyl group, a cyano group, hydroxy-lower alkyl groups such as a hydroxymethyl group, a carbamoyl group, an amino group, N-lower alkylamino groups such as an N-methylamino group, amino-lower alkyl groups such as an aminomethyl group, a group:

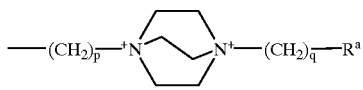

wherein $R^a$ represents a hydroxyl group or a carbamoyl group, and p and q are the same or different and each represent 0 to 4, etc., but in addition to them, there can also be mentioned $SO_2N(R^6)R^7$, optionally substituted lower alkyl groups, groups:

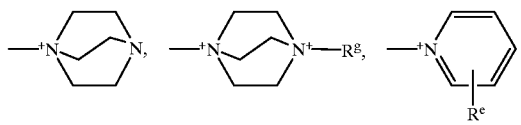

and

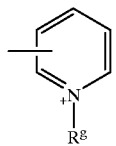

wherein $R^e$, $R^f$ and $R^g$ are as defined above, etc.

The substituent(s) in the optionally substituted lower alkyl group, the optionally substituted lower alkenyl group and the optionally substituted lower alkynyl group in $R^5$ include(s) a hydroxyl group, a methoxy group, an amino group, a nitro group, a cyano group, a carbamoyl group, a carbamoyloxy group, a formyl group, a hydrazylcarbonyloxy group, a sulfamoyl group, a trifluoromethyl group, a carboxyl group, a sulfo group, etc. Preferred among them are a hydroxyl group, an amino group, a carbamoyl group, etc.

$R^6$ and $R^7$ are the same or different, and each represent a hydrogen atom or an optionally substituted lower alkyl group. The substituent(s) include(s) a hydroxyl group, a methoxy group, an amino group, a nitro group, a cyano group, a carbamoyl group, a carbamoyloxy group, a formyl group, a hydrazylcarbonyloxy group, a sulfamoyl group, a trifluoromethyl group, a carboxyl group, a sulfo group, etc. Among them, preferred examples of $R^6$ and $R^7$ include a hydrogen atom, a methyl group, an ethyl group, a propyl group, etc., and preferred examples of their substituents include a hydroxyl group, an amino group, a carbamoyl group, etc.

$R^8$ represents a hydrogen atom or a hydroxyl-protecting group.

m and n are the same or different and each represent an integer of 0 to 4, and preferred among them are 0 to 2.

Herein, the compound of the general formula [I] is described specifically.

The compounds of the invention are compounds represented by the general formula:

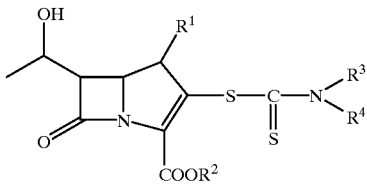

[I]

wherein $R^1$ either represents a hydrogen atom or a lower alkyl group or is bound to $R^3$ to form a heterocyclic group, $R^2$ represents a hydrogen atom, an ester residue, an alkali metal or negative charge, and $R^3$ and $R^4$ are the same or different, and each represent a hydrogen atom or a hydrocarbonic group optionally containing hetero atom(s) selected from the group consisting of oxygen atom(s), sulfur atom(s) and nitrogen atom(s), or they are combined together with the nitrogen atom to which they bound to form a heterocyclic group, and a preferred group of compounds among them are compounds represented by the general formula:

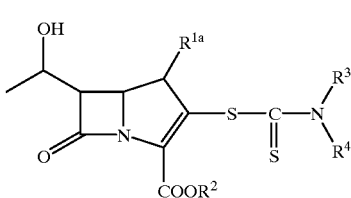

[I-a]

wherein $R^{1a}$ represents a hydrogen atom or a lower alkyl group, $R^2$ represents a hydrogen atom, an ester residue, an alkali metal or negative charge, and $R^3$ and $R^4$ are the same or different, and each represent a hydrogen atom or a hydrocarbonic group optionally containing hetero atom(s) selected from the group consisting of oxygen atom(s), sulfur atom(s) and nitrogen atom(s), or they are combined together with the nitrogen atom to which they bound to form a heterocyclic group.

In the compound of the general formula [I-a], $R^3$ and $R^4$ are the same or different, and each represent a hydrogen atom or a hydrocarbonic group optionally containing hetero atom(s) selected from the group consisting of oxygen atom (s), sulfur atom(s) and nitrogen atom(s), or they are combined together with the nitrogen atom to which they bound to form a heterocyclic group.

When $R^3$ and $R^4$ each represent the hydrocarbonic group, the hydrocarbonic group is represented by the formula

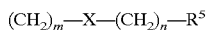

wherein $R^5$ represents a hydrogen atom, or a lower alkyl group, cyclo-lower alkyl group, lower alkenyl group, lower alkynyl group, aryl group, aromatic heterocyclic group, aliphatic heterocyclic group or polycyclic group each optionally having substituent(s), X represents a single bond, an oxygen atom, a sulfur atom , a sulfinyl group, a sulfonyl group, $NR^6$, $SO_2NR^6$, $N(R^6)SO_2NR^7$, $N(R^6)SO_2$, $CH(OR^6)$, $CONR^6$, $N(R^6)CO$, $N(R^6)CONR^7$, $N(R^6)COO$, $N(R^6)CSO$, $N(R^6)COS$, $C(R^6)=CR^7$, $C\equiv C$, $CO$, $CS$, $OC(O)$, $OC(O)NR^6$, $OC(S)NR^6$, $SC(O)$, $SC(O)NR^6$ or $C(O)O$ (wherein $R^6$ and $R^7$ each represent a hydrogen atom or an optionally substituted lower alkyl group), and m and n are the same or different and each represent an integer of 0 to 10.

Preferred are compounds having such a hydrocarbonic group that $R^5$ represents a lower alkyl group, cyclo-lower alkyl group, lower alkenyl group, aryl group, aromatic heterocyclic group or aliphatic heterocyclic group each optionally having substituent(s), X represents a single bond, an oxygen atom, a sulfur atom, a sulfinyl group, a sulfonyl group, $NR^6$, $SO_2NR^6$, $N(R^6)SO_2NR^7$, $N(R^6)SO_2$, $CH(OR^6)$, $CONR^6$, $N(R^6)CO$, $N(R^6)CONR^7$ or $N(R^6)COO$ (wherein $R^6$ and $R^7$ each represent a hydrogen atom or an optionally substituted lower alkyl group), and m and n each are 0 to 4, and particularly preferred are compounds having such a hydrocarbonic group that $R^5$ represents a lower alkyl group or lower alkenyl group optionally having substituent(s), X represents a single bond, an oxygen atom, a sulfur atom, $NR^6$, $CONR^6$ or $N(R^6)CO$ (wherein $R^6$ and $R^7$ each represent a hydrogen atom or an optionally substituted lower alkyl group), and m and n each are 0 to 2.

The substituent(s) of the hydrocarbonic group can be located at any position(s) of the hydrocarbonic group so long as it(they) can be substituted. Specific examples of the substituent(s) include, for example, lower alkyl groups such as a methyl group, a hydroxyl group, a cyano group, hydroxy-lower alkyl groups such as a hydroxymethyl group, a carboxyl group, lower alkoxycarbonyl groups such as a methoxycarbonyl group, a carbamoyl group, N-lower alkylcarbamoyl groups such as an N-methylcarbamoyl group, N,N-dilower alkylcarbamoyl groups such as an N,N-dimethylcarbamoyl group, a carbamoyloxy group, N-lower alkylcarbamoyloxy groups such as an N-methylcarbamoyloxy group, N,N-dilower alkylcarbamoyloxy groups such as an N,N-dimethylcarbamoyloxy group, an amino group, N-lower alkylamino groups such as an N-methylamino group, N,N-dilower alkylamino groups such as an N,N-dimethylamino group, N,N,N-trilower alkylammonio groups such as an N,N,N-trimethylammonio group, amino-lower alkyl groups such as an aminomethyl group, N-lower alkylamino-lower alkyl groups such as an N-methylaminomethyl group, N,N-dilower alkylamino-lower alkyl groups such as an N,N-dimethylaminomethyl group, N,N,N-trilower alkylammonio-lower alkyl groups such as an N,N,N-trimethylammoniomethyl group, lower alkanoylamino groups such as an acetylamino group, aroylamino groups such as a benzoylamino group, lower alkanoylamidino-lower alkyl groups such as an acetamidinomethyl group, lower alkylsulfonylamino groups such as a methanesulfonylamino group, N,N-dilower alkyl-N-hydroxy-lower alkylammonio-lower alkyl groups such as an N,N-dimethyl-N-hydroxypropylammoniomethyl group, N,N-dilower alkyl-N-dilower alkylamino-lower alkylammonio-lower alkyl groups such as an N,N-dimethyl-N-dimethylaminoethylammoniomethyl group, a hydroxyimino group, lower alkoxyimino groups such as a methoxyimino group, groups:

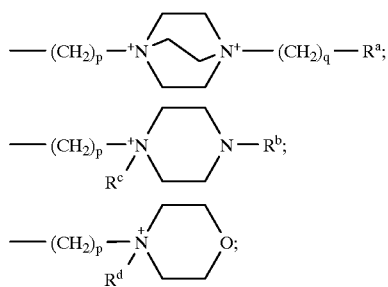

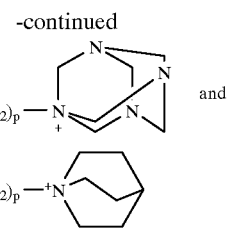

wherein $R^a$ represents a hydroxyl group or a carbamoyl group, $R^b$ represents a lower alkyl group, a formyl group or a lower alkanoyl group, $R^c$ and $R^d$ are the same or different and each represent a lower alkyl group, and p and q are the same or different and each represent 0 to 4, etc. Preferred compounds are compounds each having substituent(s), among them, for example, a hydroxyl group, a cyano group, hydroxy-lower alkyl groups such as a hydroxymethyl group, a carboxyl group, lower alkoxycarbonyl groups such as a methoxycarbonyl group, a carbamoyl group, N-lower alkylcarbamoyl groups such as an N-methylcarbamoyl group, N,N-dilower alkylcarbamoyl groups such as an N,N-dimethylcarbamoyl group, a carbamoyloxy group, an amino group, N-lower alkylamino groups such as an N-methylamino group, N,N-dilower alkylamino groups such as an N,N-dimethylamino group, N,N,N-trilower alkylammonio groups such as an N,N,N-trimethylammonio group, amino-lower alkyl groups such as an aminomethyl group, lower alkanoylamidino-lower alkyl groups such as an acetoamidinomethyl group, a group:

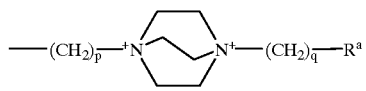

wherein $R^a$ represents a hydroxyl group or a carbamoyl group, and p and q are the same or different and each represent 0 to 4, etc., and particularly preferred are compounds each having substituent(s), for example, a hydroxyl group, a cyano group, hydroxy-lower alkyl groups such as a hydroxymethyl group, a carbamoyl group, an amino group, N-lower alkylamino groups such as an N-methylamino group, aminolower alkyl groups such as an aminomethyl group, a group:

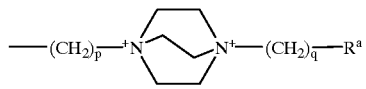

wherein $R^a$ represents a hydroxyl group or a carbamoyl group, and p and q are the same or different and each represent 0 to 4, etc.

In addition to these compounds, compounds each having, as substituent(s) of $R^5$, substituent(s), for example, halogen atoms such as a fluorine atom, a chlorine atom, a bromine atom and an iodine atom, a trifluoromethyl group, an azido group, a nitro group, $SR^6$, $COR^6$, $N(R^6)CHO$, $COOR^6$, $SO_2N(R^6)R^7$, $CSN(R^6)R^7$, $SC(S)N(R^6)R^7$, cyclo-lower alkyl groups, optionally substituted lower alkenyl groups, optionally substituted lower alkynyl groups, groups:

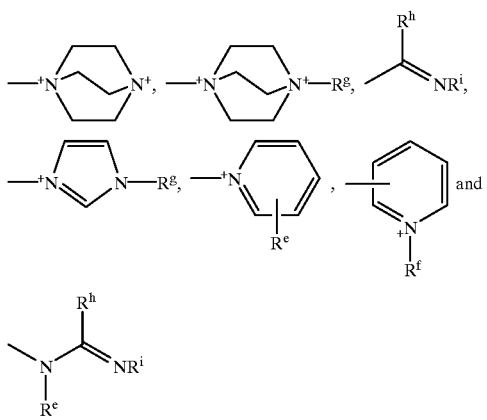

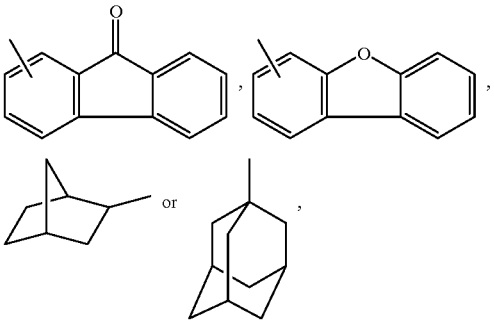

wherein $R^e$, $R^f$, $R^g$ and $R^h$ are the same or different, and each represent a hydrogen atom, or a lower alkyl group, cyclo-lower alkyl group, lower alkenyl group, lower alkynyl group, aryl group, aromatic heterocyclic group or aliphatic heterocyclic group each optionally having substituent(s), $R^i$ represents a hydrogen atom, or a lower alkyl group or cyclo-lower alkyl group each optionally having substituent(s)

can also be mentioned as the compounds of the invention.

Further, preferred examples thereof include compounds having substituent(s), for example, $SO_2N(R^6)R^7$ optionally substituted lower alkyl groups, groups:

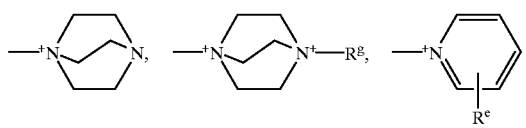

and

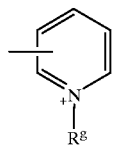

wherein $R^e$, $R^f$ and $R^g$ are as defined above, etc.

The substituent(s) in the optionally substituted lower alkyl group, the optionally substituted lower alkenyl group and the optionally substituted lower alkynyl group in $R^5$ include(s) a hydroxyl group, a methoxy group, an amino group, a nitro group, a cyano group, a carbamoyl group, a carbamoyloxy group, a formyl group, a hydrazylcarbonyloxy group, a sulfamoyl group, a trifluoromethyl group, a carboxyl group, a sulfo group, etc. Preferred among them are a hydroxyl group, an amino group, a carbamoyl group, etc.

$R^6$ and $R^7$ are the same or different, and each represent a hydrogen atom or an optionally substituted lower alkyl group. The substituent(s) include(s) a hydroxyl group, a methoxy group, an amino group, a nito group, a cyano group, a carbamoyl group, a carbamoyloxy group, a formyl group, a hydrazylcarbonyloxy group, a sulfamoyl group, a trifluoromethyl group, a carboxyl group, a sulfo group, etc. Among them, preferred examples of $R^6$ and $R^7$ include a hydrogen atom, a methyl group, an ethyl group, a propyl group, etc., and preferred examples of their substituents include a hydroxyl group, an amino group, a carbamoyl group, etc.

As specific examples in the case where $R^5$ is a polycyclic group, there can, for example, be mentioned compounds each having a substituent such as, for example, and preferred among them are compounds each having a substituent such as

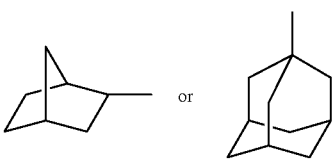

Further, when $R^3$ and $R^4$ are combined together with the nitrogen atom to which they bind to form a heterocyclic group or a polycyclic group, the heterocyclic group means a saturated or unsaturated 3 to 14-membered monocyclic ring or a saturated or unsaturated 3 to 14-membered condensed ring or assembled ring composed of 2 or 3 rings, wherein nitrogen atom(s) may be made quaternary. The heterocyclic group is not particularly limited so long as it is a heterocyclic group capable of being formed together with S—C(=S)N, a partial structure of the 2-position substituent of the carbapenem skeleton which is the characteristic of the invention, and can further have 1 to 3 substituents designated $R^3$.

Specifically, when the heterocyclic group is a saturated or unsaturated 3 to 14-membered monocyclic ring wherein nitrogen atom(s) may be made quaternary, there can be mentioned compounds each having a heterocyclic group such as, for example,

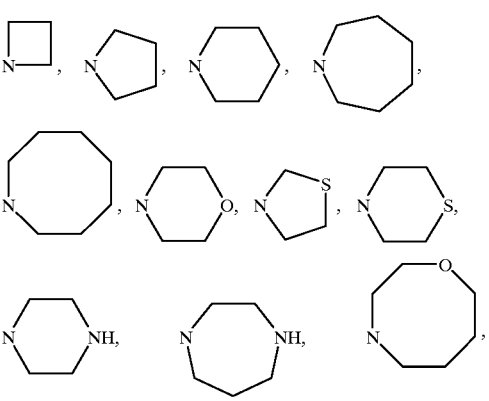

-continued

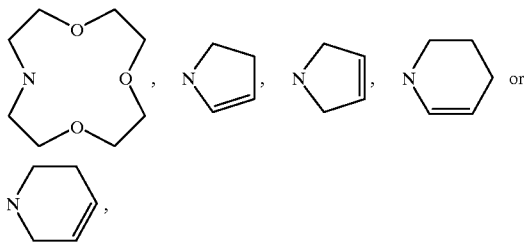

and preferred among them are compounds each having a heterocyclic group such as, for example,

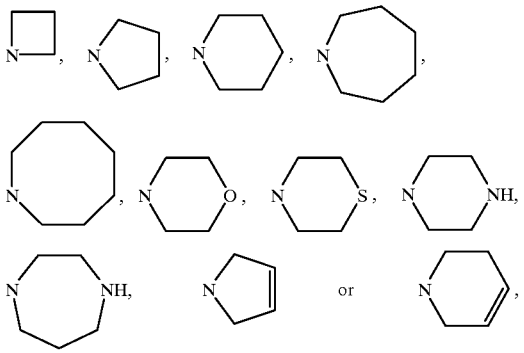

and particularly preferred among them are compounds each having a heterocyclic group such as, for example,

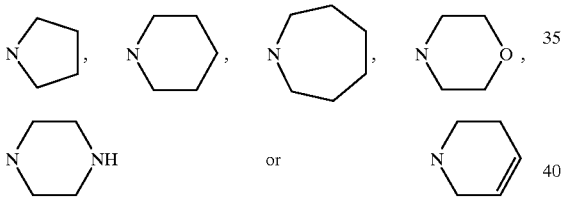

The substituent(s) of such a monocyclic saturated aliphatic heterocyclic group can bind to any of the positions of the heterocyclic group so long as it is a position capable of being substituted. Specific examples of the substituent(s) include, for example, lower alkyl groups such as a methyl group, a hydroxyl group, lower alkoxy groups, hydroxy-lower alkyl groups such as a hydroxymethyl group, a carboxyl group, a carbamoyl group, N-lower alkylcarbamoyl groups such as an N-methylcarbamoyl group, N,N-dilower alkylcarbamoyl groups such as an N,N-dimethylcarbamoyl group, an amino group, N-lower alkylamino groups such as an N-methylamino group, N,N-dilower alkylamino groups such as an N,N-dimethylamino group, N,N,N-trilower alkylammonio groups such as an N,N,N-trimethylammonio group, amino-lower alkyl groups such as an aminomethyl group, N-lower alkylamino lower alkyl groups such as an N-methylaminomethyl group, N,N-dilower alkylamino-lower alkyl groups such as an N,N-dimethylaminomethyl group, N,N,N-trilower alkylammonio-lower alkyl groups such as an N,N,N-trimethylammoniomethyl group, lower alkanoylamino groups such as an acetylamino group, aroylamino groups such as a benzoylamino group, lower alkylsulfonylamino groups such as a methanesulfonylamino group, lower alkylthio-lower alkyl groups such as a methylthiomethyl group, lower alkylsulfonyl-lower alkyl groups such as a methanesulfonylmethyl group, lower alkylsulfiny-lower alkyl groups such as a methylsulfinylmethyl group, a hydroxyimino group, lower alkoxyimino groups such as a methoxyimino group, an oxo group, a formyl group, lower alkanoyl groups such as an acetyl group, carbamoyl-lower alkylcarbonyl groups such as a carbamoylethylcarbonyl group, amino-lower alkylcarbonyl groups such as an aminomethylcarbonyl group, carboxy-lower alkycarbonyl groups such as a carboxyethylcarbonyl group, N-lower alkylamino-lower alkylcarbonyl groups such as an N-methylaminomethylcarbonyl group, N,N-dilower alkylamino-lower alkylcarbonyl groups such as an N,N-dimethylaminomethylcarbonyl group, N,N,N-trilower alkylammonio-lower alkylcarbonyl groups such as an N,N,N-trimethylammoniomethylcarbonyl group, hydroxy-lower alkylcarbonyl groups such as a hydroxymethylcarbonyl group, groups:

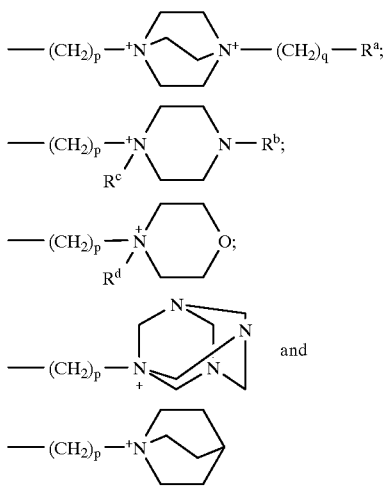

wherein $R^a$ represents a hydroxyl group or a carbamoyl group, $R^b$ represents a lower alkyl group, a formyl group or a lower alkanoyl group, $R^c$ and $R^d$ are the same or different and each represent a lower alkyl group, and p and q are the same or different and each represent 0 to 4, etc., and preferred among them are lower alkyl groups such as a methyl group, a hydroxyl group, lower alkoxy groups, hydroxy-lower alkyl groups such as a hydroxymethyl group, a carboxyl group, a carbamoyl group, an amino group, N-lower alkylamino lower alkyl groups such as an N-methylaminomethyl group, N,N-dilower alkylamino lower alkyl groups such as an N,N-dimethylaminomethyl group, N,N,N-trilower alkylammonio-lower alkyl groups such as an N,N,N-trimethylammoniomethyl group, lower alkanoylamino groups such as an acetylamino group, lower alkylsulfonylamino groups such as a methanesulfonylamino group, a hydroxyimino group, lower alkoxyimino groups such as a methoxyimino group, an oxo group, lower alkanoyl groups such as an acetyl group, amino-lower alkylcarbonyl groups such as an aminomethylcarbonyl group, carboxy-lower alkylcarbonyl groups such as a carboxyethylcarbonyl group, N-lower alkylamino-lower alkylcarbonyl groups such as an N-methylaminomethylcarbonyl group, N,N-dilower alkylamino-lower alkylcarbonyl groups such as an N,N-dimethylaminomethylcarbonyl group, N,N,N-triloweralkylammonio-lower alkylcarbonyl groups such as an N,N,N-trimethylammoniomethylcarbonyl group, hydroxy-lower alkylcarbonyl groups such as a hydroxymethylcarbonyl group, a group:

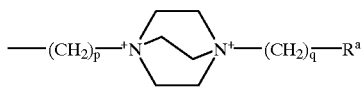

wherein $R^a$ represents a hydroxyl group or a carbamoyl group, and p and q are the same or different and each represent 0 to 4, etc., and particularly preferred are, for example, lower alkyl groups such as a methyl group, a hydroxyl group, a hydroxyimino group, lower alkoxyimino groups such as a methoxyimino group, amino-lower alkylcarbonyl groups such as an aminomethylcarbonyl group, N-lower alkylamino-lower alkylcarbonyl groups such as an N-methylaminomethylcarbonyl group, N,N-dilower alkylamino-lower alkylcarbonyl groups such as an N,N-dimethylaminomethylcarbonyl group, a group:

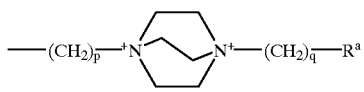

wherein $R^a$ represents a hydroxyl group or a carbamoyl group, and p and q are the same or different and each represent 0 to 4, etc.

The monocyclic unsaturated aliphatic heterocyclic group can be monosubstituted or disubstituted with the same or different substituent(s) at any position(s) so long as the position(s) can be substituted. Specific examples of the substituent(s) include, for example, a hydrogen atom, halogen atoms such as a chlorine atom and a bromine atom, lower alkoxy groups such as a methoxy group, lower alkyl groups such as a methyl group, a carbamoyl group, carbamoyl-lower alkyl groups such as a carbamoylmethyl group, amino-lower alkyl groups such as an aminomethyl group, N-lower alkylamino-lower alkyl groups such as an N-methylaminomethyl group, N,N-dilower alkylamino-lower alkyl groups such as an N,N-dimethylaminomethyl group, N,N,N-trilower alkylammonio-lower alkyl groups such as an N,N,N-trimethylammoniomethyl group, pyridinio-lower alkyl groups such as a pyridiniomethyl group, hydroxy-lower alkyl groups such as a hydroxymethyl group, groups

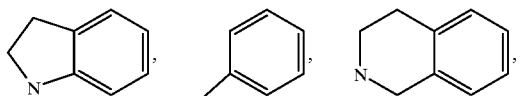

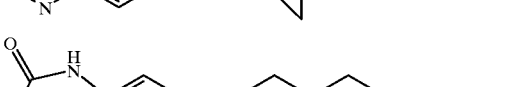

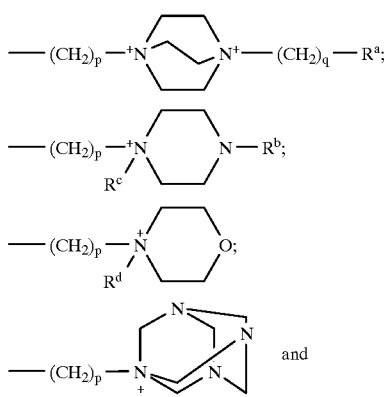

and

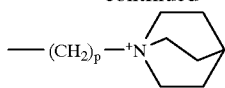

wherein $R^a$ represents a hydroxyl group or a carbamoyl group, $R^b$ represents a lower alkyl group, a formyl group or a lower alkanoyl group, $R^c$ and $R^d$ are the same or different and each represent a lower alkyl group, and p and q are the same or different and each represent 0 to 4, etc., and preferred among them are, for example, halogen atoms such as a chlorine atom and a bromine atom, carbamoyl-lower alkyl groups such as a carbamoylmethyl group, amino-lower alkyl groups such as an aminomethyl group, N,N,N-triloweralkylammonio-lower alkyl groups such as an N,N,N-trimethylammoniomethyl group, hydroxy-lower alkyl groups such as a hydroxymethyl group, a group:

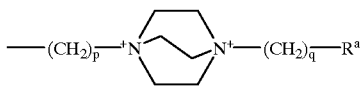

wherein $R^a$ represents a hydroxyl group or a carbamoyl group, and p and q are the same or different and each represent 0 to 4, etc., and particularly preferred are, for example, amino-lower alkyl groups such as an aminomethyl group, hydroxy-lower alkyl groups such as a hydroxymethyl group, a group:

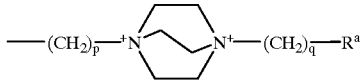

wherein $R^a$ represents a hydroxyl group or a carbamoyl group, and p and q are the same or different and each represent 0 to 4, etc.

Further, when the heterocyclic group is a saturated or unsaturated 3 to 14-membered condensed ring or assembled ring composed of 2 or 3 rings, wherein nitrogen atom(s) may be made quaternary, there can be mentioned compounds each having a heterocyclic group such as, for example,

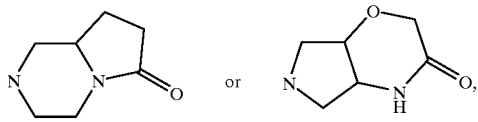

and among them, there can be mentioned compounds each having a heterocyclic group such as, for example,

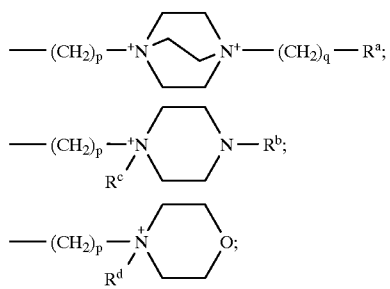

and particularly preferred are compounds each having a heterocyclic group such as, for example,

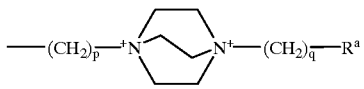

The condensed ring composed of 2 or 3 rings can be monosubstituted or disubstituted with the same or different substituent(s) at any position(s) so long as the position(s) can be substituted. Specific examples of the substituent(s) include, for example, a hydrogen atom, halogen atoms such as a chlorine atom and a bromine atom, lower alkoxy groups such as a methoxy group, lower alkyl groups such as a methyl group, a carbamoyl group, carbamoyl-lower alkyl groups such as a carbamoylmethyl group, amino-lower alkyl groups such as an aminomethyl group, N-lower alkylamino-lower alkyl groups such as an N-methylaminomethyl group, N,N-dilower alkylamino-lower alkyl groups such as an N,N-dimethylaminomethyl group, N,N,N-triloweralkylammonio-lower alkyl groups such as an N,N,N-trimethylammoniomethyl group, pyridinio-lower alkyl groups such as a pyridiniomethyl group, hydroxy-lower alkyl groups such as a hydroxymethyl group, groups:

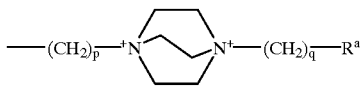

wherein $R^a$ represents a hydroxyl group or a carbamoyl group, $R^b$ represents a lower alkyl group, a formyl group or a lower alkanoyl group, $R^c$ and $R^d$ are the same or different and each represent a lower alkyl group, and p and q are the same or different and each represent 0 to 4, etc., and preferred among them are halogen atoms such as a chlorine atom and a bromine atom, lower alkyl groups such as a methyl group, carbamoyl-lower alkyl groups such as a carbamoylmethyl group, N-lower alkylamino-lower alkyl groups such as an N-methylaminomethyl group, a group:

$$—(CH_2)_p—^+N\underset{\underset{}{\diagdown}}{\diagup}N^+—(CH_2)_q—R^a$$

wherein $R^a$ represents a hydroxyl group or a carbamoyl group, and p and q are the same or different and each represent 0 to 4, etc., and particularly preferred are lower alkyl groups such as a methyl group, a group:

$$—(CH_2)_p—^+N\underset{\underset{}{\diagdown}}{\diagup}N^+—(CH_2)_q—R^a$$

wherein $R^a$ represents a hydroxyl group or a carbamoyl group, and p and q are the same or different and each represent 0 to 4, etc.

When the heterocyclic group is a saturated or unsaturated 3 to 14-membered assembled ring, wherein nitrogen atom(s) may be made quaternary, there can be mentioned compounds each having an assembled ring such as, for example,

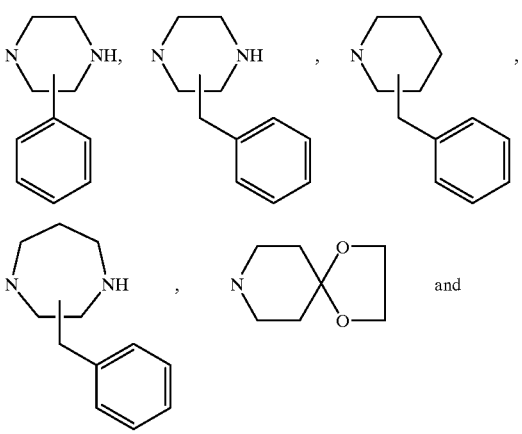

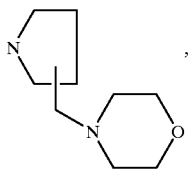, and preferred among them are compounds each having an assembled ring such as, for example,

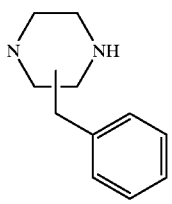

The assembled ring composed of 2 or 3 rings can be substituted at any position(s) of the heterocyclic group so long as the position(s) can be substituted. Specific examples of the substituent(s) include, for example, lower alkyl groups such as a methyl group, a hydroxyl group, hydroxy-lower alkyl groups such as a hydroxymethyl group, a carbamoyl group, N-lower alkylcarbamoyl groups such as an N-methylcarbamoyl group, N,N-dilower alkylcarbamoyl groups such as an N,N-dimethylcarbamoyl group, an amino group, N-lower alkylamino groups such as an N-methylamino group, N,N-dilower alkylamino groups such as an N,N-dimethylamino group, N,N,N-trilower alkylammonio groups such as an N,N,N-trimethylammonio group, amino-lower alkyl groups such as an aminomethyl group, N-lower alkylamino-lower alkyl groups such as an N-methylaminomethyl group, lower alkanoylamino groups such as an acetylamino group, aroylamino groups such as a benzoylamino group, lower alkylsulfonylamino groups such as a methanesulfonylamino group, etc., and preferred among them are a carbamoyl group, an amino group, N-lower alkylamino-lower alkyl groups, etc.

Pharmaceutically acceptable salts of the compounds of the general formula [I] mean pharmaceutically acceptable conventional ones, and there can be mentioned salts at the carboxyl group at the 3-position of the carbapenem skeleton or at the basic or acidic residue(s) on the side chain at the 2-position thereof.

As basic addition salts at the carboxyl group or the acidic residue(s), there can be mentioned, besides alkali metal salts such as, for example, a sodium salt and a potassium salt wherein the aforesaid $R^2$ is an alkali metal; alkaline earth metal salts such as, for example, a calcium salt and a magnesium salt; for example, an ammonium salt; aliphatic amine salts such as, for example, a trimethylamine salt, a triethylamine salt, a dicyclohexylamine salt, an ethanolamine salt, a diethanolamine salt, a triethanolamine salt and a procaine salt; aralkylamine salts such as, for example, an N,N'-dibenzylethylenediamine salt; heterocyclic aromatic amine salts such as, for example, a pyridine salt, a picoline salt, a quinoline salt and an isoquinoline salt; quaternary ammonium salts such as, for example, a tetramethylammonium salt, a tetraethylammonium salt, a benzyltrimethylammonium salt, a benzyltriethylammonium salt, a benzyltributylammonium salt, a methyltrioctylammonium salt and a tetrabutylammonium salt; basic amino acid salts such as, for example, an arginine salt and a lysine salt; etc.

As acid addition salts at the the base(s) on the side chain at the 2-position, there can be mentioned inorganic salts such as, for example, a hydrochloride, a sulfate, a nitrate, a phosphate, a carbonate, a hydrogencarbonate and a perchlorate; organic acid salts such as, for example, an acetate, a propionate, a lactate, a maleate, a fumarate, a tartrate, a malate, a citrate and an ascorbate; sulfonates such as, for example, a methanesulfonate, an isethionate, a benzenesulfonate and a p-toluenesulfonate; acidic amino acid salts such as, for example, an aspartate and a glutamate; etc.

When $R^2$ of the compound represented by the general formula [I] is negative charge, the compound has quaternary ammonium group(s), and these quaternary ammonium group(s) are neutralized with the negative charge of $R^2$ or with the negative charge of $R^2$ and another counter anion selected from the group consisting of an inorganic anion and an organic anion. As these inorganic anions and organic anions, there can be used the inorganic anions and organic anions of the above acid addition salts. Namely, those inorganic anions include, for example, a chloride ion, a bromide ion, an iodide ion, a sulfate ion, a nitrate ion, a phosphate ion, a carbonate ion, a hydrogen carbonate ion, a perchlorate ion, etc., and those organic anions include, for example, an acetate ion, a propionate ion, a lactate ion, a maleate ion, a fumarate ion, a tartrate ion, a malate ion, a citrate ion, an ascorbate ion, a methanesulfonate ion, an isethionate ion, a benzenesulfonate ion, a p-toluenesulfonate ion, an aspartate ion, a glutamate ion, etc.

Pharmaceutically acceptable nontoxic esters of the compounds of the general formula [I] mean pharmaceutically acceptable conventional ones at the carboxyl group at the 3-position of carbapenem skeleton, and include esters with the aforesaid ester residues as $R^2$.

Now, description is made on the process for producing the compounds of the invention.

A compound represented by the general formula

[II]

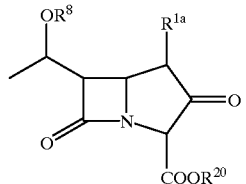

wherein $R^{1a}$ represents a hydrogen atom or a lower alkyl group, $R^8$ represents a hydrogen atom or a hydroxyl-protecting group, and $R^{20}$ represents a hydrogen atom or a carboxyl-protecting group, is reacted with an activating reagent in an inert organic solvent in the presence of a base to give a reactive derivative [II'] represented by the general formula

[II']

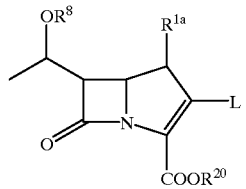

wherein L represents a leaving group, $R^{1a}$, $R^8$ and $R^{20}$ are as defined above,.

The inert solvent used in the above reaction includes, for example, diethyl ether, tetrahydrofuran, dioxane, benzene, toluene, chlorobenzene, methylene chloride, chloroform, carbon tetrachloride, dichloroethane, trichloroethylene, acetone, ethyl acetate, acetonitrile, N,N-dimethylformamide, hexamethylphosphoric acid triamide, and mixtures of these solvents, and particularly preferred are acetonitrile, benzene, etc.

The base used in the reaction includes tertiary aliphatic amines such as, for example, trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undec-7-ene (DBU) and 1,5-diazabicyclo[4.3.0]non-5-ene (DBN); and aromatic amines such as, for example, pyridine, 4-dimethylaminopyridine, picoline, lutidine, quinoline and isoquinoline, and particularly preferred are N,N-diisopropylethylamine, triethylamine, etc.

The activating reagent used in the reaction includes acid anhydrides such as, for example, trifluoroacetic anhydride, methanesulfonic anhydride, trifluoromethanesulfonic anhydride and p-toluenesulfonic anhydride; and acid chlorides such as, for example, methanesulfonyl chloride, p-toluenesulfonyl chloride and diphenyl chlorophosphate, and particularly preferred is diphenyl chlorophosphate.

The group L in the general formula [II'] means a leaving group, and include, for example, a trifluoroacetoxy group, a methanesulfonyloxy group, a trifluoromethanesulfonyloxy group, a p-toluenesulfonyloxy group, a diphenoxyphosphoryloxy group, etc., and particularly preferred is a diphenoxyphosphoryloxy group.

For the reaction, 1 to 3 moles, preferably 1 to 1.5 moles of such a base, and 1 to 1.2 moles of such an activating reagent are used per mole of a compound of the general formula [II].

The reaction is carried out in a temperature range of −40 to 50° C., preferably −20 to 20° C., and is usually completed quantitatively in 0.5 to 3 hours.

After completion of the reaction, the reaction mixture is treated according to a conventional manner to give a reactive derivative [II'] of the general formula [II] quantitatively.

Reaction between a reactive derivative [II'] and a compound represented by the general formula

[III]

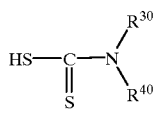

wherein $R^{30}$ and $R^{40}$ are the same or different, and each represent a hydrogen atom, an amino-protecting group or a hydrocarbonic group optionally containing hetero atom(s) selected from the group consisting of oxygen atom(s), sulfur atom(s) and nitrogen atom(s), or they are combined together with the nitrogen atom to which they bound to form a heterocyclic group (in this connection, the functional group(s) of the hydrocarbonic group or heterocyclic group can optionally be protected properly), or a salt is carried out using an inert organic solvent and a base as each mentioned above to give a compound represented by the general formula

[IV-a]

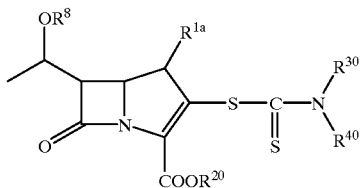

wherein $R^{1a}$, $R^8$, $R^{20}$, $R^{30}$ and $R^{40}$ are as defined above.

The reaction is carried out, in a temperature range of −40 to 60° C., preferably 0 to 30° C., using 1 to 5 moles, preferably 1.5 to 2 moles of a salt such as lithium chloride and 1 to 3 moles, preferably 1.2 to 1.5 moles of a compound of the general formula [III] per mole of a reactive derivative [II'], and is usually completed in 3 to 30 hours.

Further, it is also possible to produce a compound of the general formula [IV] from a compound of the general formula [II] only through one stage. Namely, without isolating the reactive derivative [II'] derived from the compound of the general formula [II], the compound of the general formula [III] can be subjected, in the same reaction system, to the same reaction as mentioned above to give a compound of the general formula [IV] efficiently.

After completion of the reaction, the reaction mixture is treated in a usual manner to give a crude product of the compound represented by the general formula [IV], and the crude product can be subjected to deblocking reaction without being purified. The crude product [IV] is preferably purified by subjecting it to crystallization or column chromatography using silica gel or the like.

A compound of the general formula [I] can be produced by subjecting a compound of the general formula [IV] thus obtained, if necessary, to an appropriate combination of reactions for removal of protective groups of a hydroxyl group, an amino group and a carboxyl group, and converting the resultant compound to a pharmaceutically acceptable salt or nontoxic ester.

Removal of the protective groups is carried out in different manners depending on their kinds, but according to conventional manners, for example, solvolysis, chemical reduction or hydrogenation.

When the protective group(s) of the hydroxyl group and/or amino group in the general formula [IV] is/are aralkyloxycarbonyl group(s) such as, for example, benzyloxycarbonyl group(s) or p-nitrobenzyloxycarbonyl group (s), and the protective group of the carboxyl group is an aralkyl group such as, for example, a benzyl group, a p-nitrobenzyl group or a benzhydryl group, the protective groups can be removed by catalytic hydrogenation using a platinum catalyst such as, for example, platinum oxide, platinum wire or platinum black; or a palladium catalyst such as, for example, a palladium black, palladium oxide, palladium-carbon or palladium hydroxide-carbon.

As solvents used for the catalytic hydrogenation reaction, there can, for example, be mentioned methanol, ethanol, tetrahydrofuran, dioxane, acetic acid, etc., and mixed solvents of such solvent(s) with water or a buffer such as a phosphate buffer.

The catalytic hydrogenation reaction is carried out in a hydrogen gas stream of 1 to 4 atms. in a temperature range of 0 to 50° C., and completed in 0.5 to 24 hours, preferably 5 to 15 hours.

When the protective group(s) of the hydroxyl group and/or amino group in the general formula [IV] is/are, for example, allyloxycarbonyl group(s), and the protective group of the carboxyl group is, for example, an allyl group, the protective groups can be removed by reacting the compound with an organic solvent-soluble palladium complex catalyst in an inert organic solvent containing an allyl group-capturing agent [see, the process of W. McCombie et al., J. Org. Chem., vol. 47, p. 587–590 (1982) and the process of F. Guibé et al., ibid., vol. 52, p. 4984–4993 (1987)].

As solvents used in the reaction, there can, for example, be mentioned water, acetone, diethyl ether, tetrahydrofuran, dioxane, ethyl acetate, acetonitrile, methylene chloride, chloroform, etc., and mixed solvents thereof.

As preferred palladium compound complexes used in the reaction, there can, for example, be mentioned palladium-carbon, palladium hydroxide-carbon, palladium(II) chloride, palladium(II) acetate, tetrakis(triphenylphosphine) palladium(0), tetrakis(triphenoxyphosphine) palladium(0), tetrakis(triethoxyphosphine) palladium(0), bis[ethylenebis (diphenylphosphine)] palladium(0), tetrakis[tri(2-furyl) phosphine] palladium(0), bis(triphenylphosphine) palladium(II) chloride, bis(triphenylphosphine) palladium (II) acetate, etc.

As allyl group-capturing agents, there can, for example, be mentioned dimedone, formic acid, acetic acid, ammonium formate, sodium formate, sodium 2-ethylhexanoate, potassium 2-ethylhexanoate, pyrrolidine, piperidine, tributyltin hydride, etc.

The reaction is carried out, in a temperature range of −10 to 50° C., preferably in a temperature range of 0 to 30° C., using 0.01 to 0.5 mole of a catalyst and 1 to 6 moles of a nucleophilic agent per mole of a compound of the general formula [IV], and completed usually in 0.5 to 3 hours.

When, in the above general formula [IV], the protective group(s) of the hydroxyl group and/or amino group is/are o-nitrobenzyloxycarbonyl group(s), and the protective group of the carboxyl group is an o-nitrobenzyl group, the protective groups can be removed by photoreaction (see the process of Amit et al., J. Org. Chem., vol. 39, p.192–196 (1974)).

After completion of the reaction(s) for removal of the protective group(s), the reaction mixture can be subjected to usual treatment method(s), for example, column chromatography using silica gel or an adsorption resin or the like, or to an operation such as freeze-drying or crystallization to isolate a compound of the general formula [I].

When the protective group of the carboxyl group at the 3-position of a compound of the general formula [IV] is a lower alkanoyloxyalkyl group such as, for example, an acetoxymethyl group or a pivaloyloxymethyl group; or, for example, a methoxymethyl group, an indanyl group, a phthalidyl group or the like, such an ester is physiologically hydrolyzed in vivo, and therefore, can be, directly, administered to human beings or animals without removing the protective group(s).

A compound of the general formula [I] can be converted to a pharmaceutically acceptable salt or ester by a conventional method.

A starting material represented by the general formula [II] can, for example, be produced according to the process of Salzmann et al. (see J. Am. Chem. Soc., vol. 102, p.6161–6163 (1981)) when $R^2$ is a hydrogen atom, or according to the process of Shih et al. (see Heterocycles, vol. 21, p. 29–40 (1984)) when $R^2$ is a methyl group, or a similar process thereto.

A dithiocarbamic acid, a starting material, represented by the general formula [III] can, generally, be synthesized by making carbon disulfide acting on an amine. Particularly, when the amine is an aromatic amine, it can be converted to a dithiocarbamic acid, for example, according to the process of J. Garin et al. (Synthesis, p. 961, 1981).

As solvents used in the reaction, there can be mentioned ethers such as ,for example, diethyl ether, diisopropyl ether, dioxane and tetrahydrofuran, alcohols such as, for example, methanol, ethanol and propanol, inert organic solvents such as, for example, benzene, toluene, chlorobenzene, methylene chloride, chloroform, carbon tetrachloride, dichloroethane, trichloroethylene, acetone, ethyl acetate, acetonitrile, N,N-dimethylformamide, dimethyl sulfoxide and hexamethylphosphoric triamide, water, and their mixed solvents, and preferred among them are tetrahydrofuran, diisopropyl ether, etc.

As bases used in the reaction, there can be mentioned tertiary aliphatic amines such as ,for example, trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undec-7-ene (DBU) and 1,5-azabicyclo[4.3.0]non-5-ene (DBN); aromatic amines such as ,for example, pyridine, 4-dimethylaminopyridine, picoline, lutidine, quinoline and isoquinoline; alkali metals such as ,for example, metallic potassium, metallic sodium and metallic lithium; alkali metal hydrides such as, for example, sodium hydride and potassium hydride; alkali metal alkylates such as, for example, butyllithium; alkali metal alkoxides such as ,for example, potassium t-butylate, sodium ethylate and sodium methylate; alkali metal hydroxides such as, for example, potassium hydroxide and sodium hydroxide; alkali metal carbonates such as, for example, potassium carbonate; etc. Particularly preferred are triethylamine, N,N-diisopropylethylamine, etc.

The reaction is carried out, in a temperature range of −40 to 50° C., preferably 0 to 20° C., using 1 to 5 moles, preferably 3 moles of the base, 1 to 3 moles, preferably 1.5 moles of carbon disulfide per mole of the primary amine or secondary amine, and quantitatively completed usually in 0.5 to 5 hours.

After completion of the reaction, the crystals deposited are taken by filtration and dried to give a desired dithiocarbamic acid.

As salts of compounds of the general formula [III], there can be mentioned salts with alkali metals such as, for example, lithium, sodium and potassium; salts with tertiary amines such as, for example, triethylamine, diisopropylethylamine, N-methylmorpholine, N-methylpyrrolidine and N-methylpiperidine; salts with aromatic amines such as, for example, pyridine, 4-dimethylaminopyridine, picoline and lutidine; etc., and preferred among them are lithium salts, sodium salts, triethylamine salts, diisopropylethylamine salts, etc.

The compounds of the invention exhibit strong antibacterial activities against various Gram-positive bacteria and Gram-negative bacteria.

In order to specifically demonstrate the usefulness of the compounds of the invention, in vitro antibacterial activities against bacteria were assayed according to the following agar plate dilution method (standard method by Japan Chemotherapy Society, Chemotherapy, vol. 29, p.76–79 (1981)). One platinum loopful (inoculum: $10^6$ CFU/ml) of each test microorganism cultured overnight in Mueller Hinton broth was inoculated into Mueller Hinton agars (MH agar). These media contained an antimicrobial agent in various concentrations. Each test microorganism was cultured at 37° C. for 16 hours, and then the minimum inhibitory concentration (MIC: µg/ml) was assayed. Accordingly, the minimum inhibitory concentrations of compounds of the invention were assayed. The results are shown in Table 1.

TABLE 1

Minimum inhibitory Concentration (MIC: µg/ml)

| Test microorganism | Example I-26 | Example I-41 | Example I-63 | Example I-72 | Example III-2 | Example IV-5 |
|---|---|---|---|---|---|---|
| S. aureus MB4970 | 0.012 | <0.006 | 0025 | 0.025 | ≦0.006 | ≦0.006 |
| S. aureus JS1 | 0.2 | 0.1 | 0.2 | 0.1 | 0.1 | 0.1 |
| S. aureus BB5939* | 0.78 | 0.39 | 1.56 | 1.56 | 0.39 | 0.39 |
| P. mirabilis MB4955 | 0.05 | 0.1 | 0.1 | 0.05 | 0.20 | 0.05 |

*β-lactamase-producing bacterium

The minimum inhibitory concentrations (MIC: µg/ml) of compounds of the invention were assayed according to the above agar plate dilution method using the media supplemented with 2% sodium chloride as test media and using the culture conditions of 35° C. and 48 hours. The results are shown in Table 2.

TABLE 2

Minimum inhibitory Concentration (MIC : µg/ml)

| Test microorganism | Example1 - 51 |
|---|---|
| S. aureus MB5393 | 0.39 |
| S. aureus CSa929 | 0.39 |

The compounds of the invention have wide antibacterial spectra and excellent antibacterial activities against Gram-positive bacteria and Gram-negative bacteria, and are useful as antibacterial agents for treatment and prophylaxis of human infectious diseases caused by these pathogenic bacteria. Typical pathogens sensitive to the antibacterial agents of the invention include, for example, species of the genus Staphylococcus, genus Enteroococcus, genus Escherichia, genus Enterobactor, genus Klebsiella, genus Serratia, genus Proteus, genus Pseudomonas, etc.

Further, the compounds of the invention are compounds remarkably improved in the central nervous symptoms and renal toxicity, compared with imipenem.

A compound of the invention can be used in the form of pharmaceutical preparations suitable for parenteral administration, oral administration or external administration, by mixing it with carriers of solid or liquid excipients known in this field. The main administration route is local administration or parenteral administration (intravenous or intramuscular injection) by injection. The pharmaceutical preparations include, for example, liquid preparations such as injections, syrups and emulsions, solid preparations such as tablets, capsules and granules, and external preparations such as ointments and suppositories. These preparations may, if necessary, contain additives usually used such as bases, auxiliaries, stabilizers, wetting agents, emulsifiers, absorption accelerators and surfactants.

The additives include, for example, distilled water for injection, Ringer's solution, glucose, sucrose syrups, gelatin, edible oils, cacao butter, ethylene glycol, sucrose, corn starch, magnesium stearate, talc, etc.

The dose is varied depending on the symptoms of patients, weight, age, the distinction of sex, dosage form, the number of times of dosage, etc., but usually, a preferred daily dose is in a range of about 5 to 50 mg/kg as the effective ingredient for an adult, about 5 to 25 mg/kg as the effective ingredient for a child, and is preferably administered once a day or a few times a day in a few divided portions.

A compound of the invention can, if necessary, be administered in combination with a DHP-I inhibitor such as cilastatin [sodium (Z)-7-(L-amino-2-carboxyethylthio)-2-(2,2-dimethylcyclopropanecarboxamido)-2-heptenoate (Japanese Published Unexamined Patent Application No. 81518/1981; European Patent No. 28,778; J. Med. Chem., vol. 30, p.1074 (1987)).

EXAMPLES AND REFERENCE EXAMPLES

The invention is further specifically described below by examples and reference examples, but the invention should not be limited at all thereby.

In thin layer chromatography in examples and reference examples, Silicagel 60F$_{245}$ (Merck) was used as the plate, and a UV detector was used as a detecting device. Wakogel™ C-300 (Wako Junyaku) was used as silica gel for columns, and LC-SORB™ SP-B-ODS (Chemco) or YMC-GEL™ ODS-AQ 120-S50 (Yamamura Chemical Laboratories) was used as silica gel for reverse phase columns. JASCO 800 series (Nippon Bunko) was used as a high performance liquid chromatograph. When an NMR spectrum was measured using dimethyl sulfoxide-d$_6$ solution or chloroform-d solution, tetramethylsilane (TMS) was used as the internal standard, and when an NMR spectrum was measured using deuterium oxide solution, 2,2-dimethyl-2-silapentane-5-sulfonate (DSS) was used as the internal standard, and the measurement was carried out using an XL-200 (200 MHz; Varian)-type spectrometer, and all δ values were shown by ppm.

The meanings of the abbreviations used for the NMR measurement are set forth below.

s: singlet
d: doublet
dd: double doublet
quint: quintet
m: multiplet
br: broad
J: coupling constant
Hz: hertz
CDCl$_3$: chloroform-d
D$_2$O: deuterium oxide The meanings of the abbreviations used in the reaction formulae, etc. are set forth below.

Ac: acetyl group
Et: ethyl group
n-Bu: n-butyl group
Bz: benzyl group n-Pr: n-propyl group
i-Pr: isopropyl group
Me: methyl group
Ph: phenyl group
PNB: p-nitrobenzyl group
POM: pivaloyloxymethyl group
Py: pyridyl group
TEA: triethylamine Reference Example 1

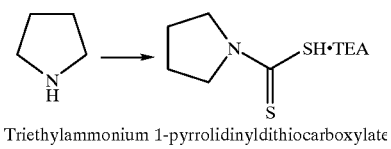

Triethylammonium 1-pyrrolidinyldithiocarboxylate

Triethylamine (25 ml, 180 mmol) and carbon disulfide (5.4 ml, 89.9 mmol) were added to a tetrahydrofuran (200 ml) solution of pyrrolidine (5 ml, 59.9 mmol) under ice cooling, and the reaction solution was stirred for 2 hours. The crystals deposited were taken by filtration, washed with diisopropyl ether and dried to give white needle crystals of the captioned compound (13.5 g, yield: 91%).

IR(KBr)cm$^{-1}$: 1375,1165,1001,943

$^1$H-NMR(D$_2$O) δ: 1.26(9H,t,J=7.0 Hz),1.97(4H,m),3.18 (6H,q, J=7.0 Hz),3.75(4H,m)

Example I-1

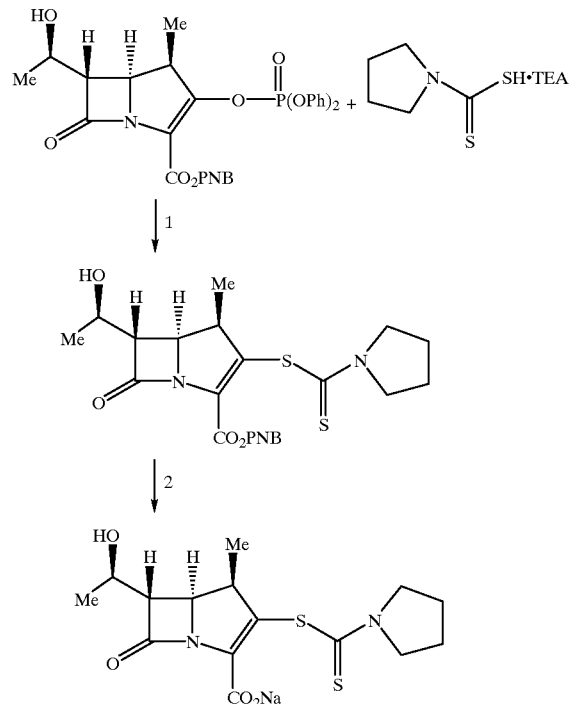

Sodium (1R,5S,6S)-6-[(R)-1-hydroxyethyl]-2-(1-pyrrolidinyl)thiocarbonylthio]-1-methyl-1-carbapen-2-em-3-carboxylate (Step 1)
Triethylammonium 1-pyrrolidinyldithiocarboxylate (1.0 g, 4.03 mmol) and lithium chloride (171 mg, 4.03 mmol) were added to a tetrahydrofuran solution (50 ml) of p-nitrobenzyl (1R,5S,6S)-2-diphenoxyphosphoryloxy-6-[(R)-1-hydroxyethyl]-1-methyl-1-carbapen-2-em-3-carboxylate (2.0 g, 3.36 mmol) at room temperature. The mixture was stirred at that temperature overnight in a nitrogen stream, and poured in a mixed liquid of ethyl acetate and water. The organic layer was washed with saturated saline, dried over anhydrous sodium sulfate and concentrated under reduced pressure. The resultant residue was subjected to silica gel column chromatography (Wakogel™ C-300, n-heptane-ethyl acetate 1:1→2:3) to give p-nitrobenzyl (1R,5S,6S)-6-[(R)-1 -hydroxyethyl]-2-[(1-pyrrolidinyl)thiocarbonylthio]-1-methyl-1-carbapen-2-em-3-carboxylate (1.21 g, yield: 74%).

IR(KBr)cm$^{-1}$: 1772,1522,1437,1346

$^1$H-NMR(CDCl$_3$) δ: 1.16(3H,d,J=7.5 Hz),1.36(3H,d,J=6.3 Hz), 1.9–2.2(4H,m),3.37(1H,dd,J=6.3,3.0 Hz),3.73(2H, m), 3.87(2H,t,J=6.9 Hz),4.09(1H,m),4.29(1H,m),4.45(1H, dd,J=9.9,3.0 Hz),5.25(1H,d,J=14 Hz),5.48(1H,d,J=14H z),7.64(2H,d,J=9.0 Hz),8.22(2H,d,J=9.0 Hz)

(Step 2)
An aqueous sodium hydrogencarbonate (51 mg, 0.61 mmol) solution (30 ml) and 10% palladium-carbon catalyst (300 mg) were added to a solution of the compound obtained in Step 1 (300 mg, 0.61 mmol) in tetrahydrofuran (30 ml) and ethanol (5 ml), and the reaction mixture was vigorously stirred overnight in a hydrogen stream. The catalyst was removed from the the reaction mixture, and the filtrate was concentrated under reduced pressure. The insoluble matter was filtered out, and the filtrate was subjected to reverse phase column chromatography (YMC•GEL™ ODS-AQ-120-S50, 14 ml; aqueous 20% methanol solution), and the fractions containing the desired compound were concentrated and freeze-dried to give the captioned compound (117 mg, yield: 51%).

IR(KBr)cm$^{-1}$: 1749,1608,1437,1389

$^1$H-NMR(D$_2$O) δ: 1.11(3H,d,J=7 Hz),1.28(3H,d,J=6 Hz), 1.9–2.2(4H,m),3.53(1H,dd,J=6,3 Hz),3.6–3.9(5H,m),4.25 (1H, m),4.36(1H,dd,J=10,3 Hz)

Compounds from Example I-2 to Example I-132 were produced by the same reaction as above.

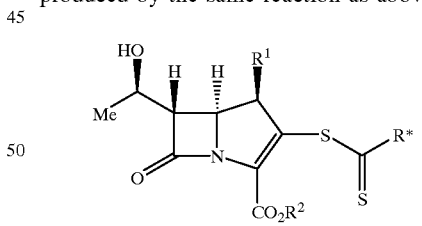

Example I-2

R$^1$ = Me; R$^2$ = Na; R* = [pyrrolidinyl]

IR(KBr)cm$^{-1}$: 1751,1601,1489,1394,1286

$^1$H-NMR(D$_2$O) δ: 1.10(3H,d,J=7.3 Hz),1.27(3H,d,J=6.6 Hz),2.37 (2H,m),3.53(1H,dd,J=6.0,3.0 Hz),3.72(1H,m), 4.2–4.4 (6H,m)

Example I-3

R¹ = Me; R² = Na; R* = 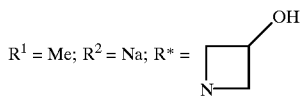

IR(KBr)cm⁻¹: 3400,1755,1604,1489,1390,1138
¹H-NMR(D₂O) δ: 1.10(3H,d,J=7.4 Hz),1.25(3H,d,J=6.3 Hz),3.52 (1H,dd,J=2.9,5.7 Hz),3.70(1H,m),4.0–4.3(3H,m), 4.34(1H,m),4.4–4.8(3H,m)

Example I-4

R¹ = Me; R² = Na; R* = 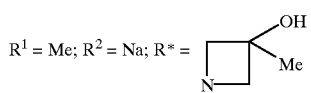

IR(KBr)cm⁻¹: 3400,1757,1600,1489,1446,1388
¹H-NMR(D₂O) δ: 1.10(3H,d,J=7.2 Hz),1.26(3H,d,J=6.3 Hz),1.53 (3H,s),3.53(1H,dd,J=2.9,6.0 Hz),3.70(1H,m), 4.0–4.4(6H,m)

Example I-5

R¹ = Me; R² = Na; R* = 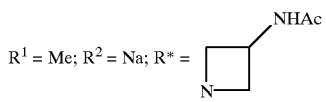

IR(KBr)cm⁻¹: 3400,1757,1653,1608,1558,1489,1452, 1387, 1279,1145
¹H-NMR(D₂O) δ: 1.09(3H,d,J=6.9 Hz),1.25(3H,d,J=6.9 Hz),2.00 (3H,s),3.52(1H,dd,J=3.1,5.9 Hz),3.70(1H,m), 4.1–4.3 (3H,m),4.34(1H,dd,J=2.8,10.0 Hz),4.5–4.7(3H,m)

Example I-6

R¹ = Me; R² = Na; R* = 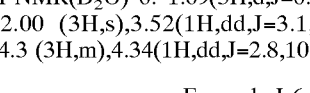

IR(KBr)cm⁻¹: 1749,1604,1434,1386
¹H-NMR(D₂O) δ: 1.12(3H,d,J=7 Hz),1.29(3H,d,J=6 Hz), 1.65(2H, m),2.02(2H,m),3.54(1H,dd,J=3,6 Hz),3.65–3.90 (3H,m), 4.06(1H,m),4.26(1H,m),4.37(1H,dd,J=3,10 Hz)

Example I-7

R¹ = Me; R² = Na; R* = 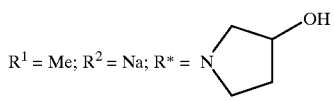

IR(KBr)cm⁻¹: 3401,1751,1643,1616
¹H-NMR(D₂O) δ: {1.02(d,J=7.3 Hz),1.11(d,J=7.3 Hz)} (3H),1.27(3H,d,J=6.3 Hz),1.94–2.18(3H,m),{2.35–2.45(m), 2.49–2.69(m)}(1H),{2.92(s),2.97(s)}(3H),{3.14(s),3.18(s)} (3H), 3.49–3.54(1H,m),3.68–4.05(3H,m),4.25(1H,dq,J=6.1, 5.6 Hz),4.32–4.36(1H,m),5.30–5.34(1H,m)

Example I-8

R¹ = Me; R² = Na; R* = 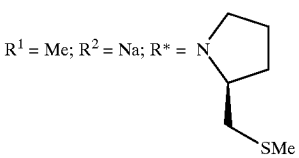

IR(KBr)cm⁻¹: 3426,1764,1753,1419,1396
¹H-NMR(D₂O) δ: {1.10(d,J=7.3 Hz),1.14(d,J=7.3 Hz)} (3H),1.27 (3H,d,J=6.3 Hz),2.04–2.18(4H,m),{2.17(s),2.20 (s)}(3H), {2.66(dd,J=9.9,13.2 Hz),2.76(dd,J=9.9,13.2 Hz)} (1H), {3.04(dd,J=3.3,14.1 Hz),3.16(dd,J=2.8,13.3 Hz)} (1H), 3.51–3.55(1H,m),3.69–3.77(1H,m),3.77–3.88(2H,m), 4.23–4.27(1H,m),4.35(1H,dd,J=3.0,9.8 Hz)

Example I 9

R¹ = Me; R² = Na; R* = 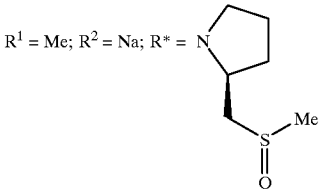

IR(KBr)cm⁻¹: 3425,1764,1753,1421,1394,1295,1128
¹H-NMR(D₂O) δ: 1.11(3H,d,J=7.3 Hz),1.28(3H,d,J=6.3 Hz),2.18–2.40(4H,m),3.20(3H,s),3.35–3.40(1H,m), 3.53–3.56(1H, m),3.69–3.84(3H,m),4.06–4.11(1H,m), 4.25–4.29(1H,m), 4.36–4.41(1H,m),5.06–5.10(1H,m)

Example I-10

R¹ = Me; R² = Na; R* = 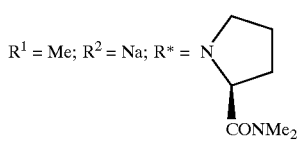

IR(KBr)cm⁻¹: 3394,1764,1753,1421,1394,1020
¹H-NMR(D₂O) δ: 1.06–1.15(3H,m),1.27(3H,d,J=6.4 Hz), 2.05–2.30(4H,m),{2.74(s),2.77(s),2.78(s),2.79(s)}(3H), {3.03–3.11(m),3.19–3.27(m)}(1H),{3.37–3.43(m), 3.48–3.69(m)}(1H),3.71–3.80(1H,m),3.81–3.89(2H,m), 4.25(1H,dq,J=6.3,6.1 Hz),4.36(1H,dd,J=2.6,9.9 Hz), {4.80–4.92(m),5.06–5.11(m)}(3H)

Example I-11

R¹ = H; R² = Na; R* =

IR(KBr)cm⁻¹: 1764,1600,1430
¹H-NMR(D₂O) δ: 1.25(3H,d,J=6.5 Hz),1.95–2.10(4H,m), 2.99(1H,dd,J=17,9.5 Hz),3.45–3.52(2H,m),3.65–3.85 (4H, m),4.15–4.35(2H,m)

Example I-12

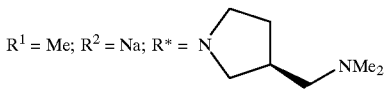

IR(KBr)cm$^{-1}$: 3407,1751,1602,1436,1384

$^1$H-NMR(D$_2$O) δ: 1.06(3H,d,J=7.4 Hz), 1.24(3H,d,J=6.4 Hz), {1.75–1.95(m),2.19–2.39(m)}(3H),2.85(6H,s),3.23 (2H,br d,J=6.9 Hz),3.45–3.55(2H,m),3.65–3.80(2H,m), 4.00–4.18(2H,m),4.18–4.27(1H,m),4.22–4.38(1H,m)

Example I-13

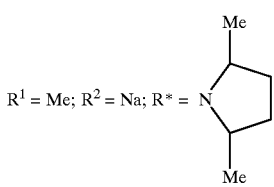

IR(KBr)cm$^{-1}$: 1760,1600

$^1$H-NMR(D$_2$O) δ: 0.82–2.20(16H,m),2.89–4.63(6H,m)

Example I-14

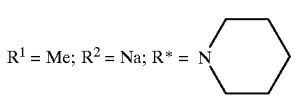

IR(KBr)cm$^{-1}$: 1749,1603,1227

$^1$H-NMR(D$_2$O) δ: 1.11(3H,d,J=7.3 Hz),1.28(3H,d,J=6.5 Hz),1.71 (6H,br),3.52(1H,dd,J=3.0,5.9 Hz),3.69(1H,m), 3.9–4.3 (5H,m),4.36(1H,dd,J=3.0,9.8 Hz)

Example I-15

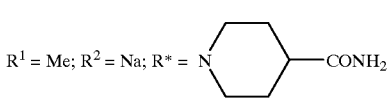

IR(KBr)cm$^{-1}$: 1756,1662,1594,1394

$^1$H-NMR(D$_2$O) δ: 1.12(3H,d,J=7 Hz),1.29(3H,d,J=6.5 Hz),1.76 (2H,m),2.00(2H,m),2.74(1H,m),3.30(1H,m), 3.40–3.55 (2H,m),3.70(1H,m),4.26(1H,m),4.37(1H,dd,J= 2.5,9.5 Hz), 5.30(1H,m)

Example I-16

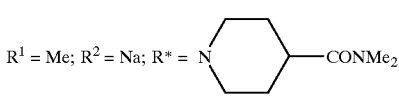

IR(KBr)cm$^{-1}$: 1749,1616,1386

$^1$H-NMR(D$_2$O) δ: 1.12(3H,d,J=7 Hz),1.29(3H,d,J=6.5 Hz),1.72 (2H,m),1.91(2H,m),2.93(3H,s),3.16(3H,s),3.70 (1H,m), 4.27(1H,m),4.36(1H,m),5.31(1H,m)

Example I-17

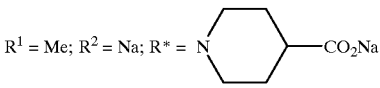

IR(KBr)cm$^{-1}$: 1745,1567,1402

$^1$H-NMR(D$_2$O) δ: 1.10(3H,m),1.26(3H,m),1.69(2H,m), 2.00(2H, m),3.69(1H,m),4.25(1H,m),4.35(1H,dd,J=9.5,3 Hz),

Example I-18

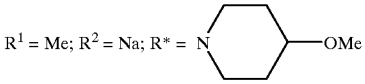

IR(KBr)cm$^{-1}$: 1757,1610,1429,1390

$^1$H-NMR(D$_2$O) δ: 1.19(3H,d,J=7.5 Hz),1.26(3H,d,J=6.5 Hz),1.65 (2H,m),2.02(2H,m),3.37(3H,s),3.51(1H,dd,J=6,3 Hz), 3.60–4.00(5H,m),4.24(2H,m),4.34(1H,dd,J=9.5,3 Hz)

Example I-19

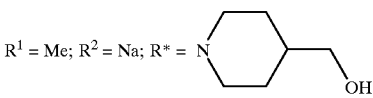

IR(KBr)cm$^{-1}$: 1742,1602,1390,1251

$^1$H-NMR(D$_2$O) δ: 1.09(3H,d,J=7 Hz),1.15–1.40(5H,m), 1.87(3H, m),3.20(1H,m),3.30–3.55(3H,m),3.65(1H,m),4.23 (1H,m), 4.31(1H,m),5.25(1H,m)

Example I-20

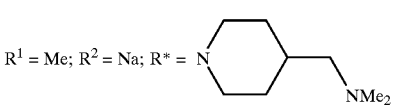

IR(KBr)cm$^{-1}$: 1760,1602,1481,1430,1376

$^1$H-NMR(D$_2$O) δ: 1.08(3H,d,J=7 Hz),1.25(3H,d,J=6.5 Hz),1.40 (2H,m),1.88(2H,m),2.29(1H,m),2.87(6H,s),3.05 (2H,d, J=7 Hz),3.20(1H,m),3.35–3.55(2H,m),3.65(1H,m), 4.23 (1H,m),4.34(1H,dd,J=9.5,3 Hz),5.30(1H,m)

Example I-21

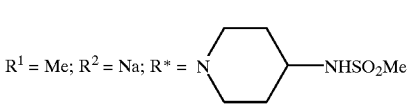

IR(KBr)cm$^{-1}$: 1742,1604,1444,1388,1315

$^1$H-NMR(D$_2$O) δ: 1.08(3H,d,J=7 Hz),1.25(3H,d,J=6.5 Hz),1.65 (2H,m),2.10(2H,m),3.09(3H,s),3.40–3.80(4H,m), 4.23 (1H,m),4.34(1H,dd,J=9.5,3 Hz),4.55(1H,m),5.05(1H, m)

Example I-22

R¹ = Me;    R² = Na;    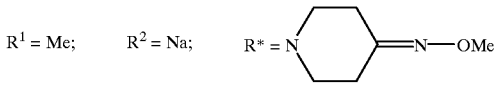

IR(KBr)cm⁻¹: 3405,1759,1678,1554,1408,1207,1081, 723

¹H-NMR(D₂O) δ: 1.08(3H,d,J=7.44 Hz),1.25(3H,d,J=6.37 Hz), 2.58–2.80(4H,m),3.50–3.70(2H,m),3.81(3H,s), 4.05–4.37 (7H,m)

Example I-23

R¹ = Me;    R² = Na;    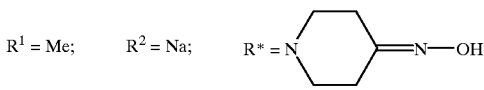

IR(KBr)cm⁻¹: 3741,3411,1745,1687,1552,1406

¹H-NMR(D₂O) δ: 1.08(3H,d,J=7.3 Hz),1.25(3H,d,J=6.3 Hz),2.58 2.82(4H,m),3.50–3.70(2H,m),4.05–4.37(6H,m)

Example I-24

R¹ = Me;    R² = Na;    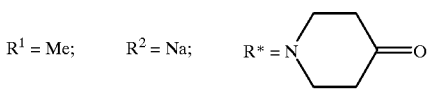

IR(KBr)cm⁻¹: 3489,3413,1745,1608,1552,1398,1227

¹H-NMR(D₂O) δ: 1.07(3H,d,J=7.51 Hz),1.24(3H,d,J=6.26 Hz), 1.83–1.92(2H,m),2.66–2.71(2H,m),3.48–3.70 (2H,m), 3.98–4.48(6H,m)

Example I-25

R¹ = Me;    R² = Na;    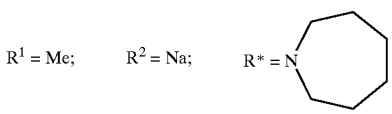

IR(KBr)cm⁻¹: 1760,1602

¹H-NMR(D₂O) δ: 1.10(3H,d,J=7 Hz),1.26(3H,d,J=6 Hz), 1.55 (4H,m),1.83(4H,m),3.51(1H,dd,J=2.5,6 Hz),3.73(1H, m), 3.90–4.15(4H,m),4.24(1H,m),4.35(1H,dd,J=2.5,10 Hz)

Example I-26

R¹ = Me;    R² = Na;    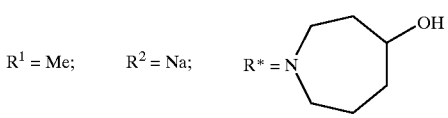

IR(KBr)cm⁻¹: 1745,1691,1612,1390

¹H-NMR(D₂O) δ: 1.08(3H,d,J=7 Hz),1.25(3H,d,J=6.5 Hz),1.55–2.30(6H,m),3.51(1H,m),3.71(1H,m),3.80–4.15 (4H,m), 4.23(1H,m),4.34(1H,dd,J=9.5,3 Hz)

Example I-27

R¹ = Me;    R² = Na;    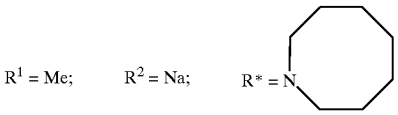

IR(KBr)cm⁻¹: 1760,1602,1380

¹H-NMR(D₂O) δ: 1.10(3H,d,J=7 Hz),1.26(3H,d,J=6 Hz), 1.53(6H, m),1.90(4H,m),3.51(1H,d,J=3,5 Hz),3.74(1H,m), 3.85–4.20(4H,m),4.24(1H,m),4.34(1H,dd,J=3,10 Hz)

Example I-28

R¹ = Me;    R² = Na;    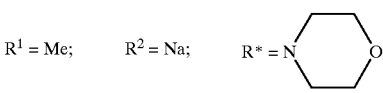

IR(KBr)cm⁻¹: 1749,1603,1387,1269,1232

¹H-NMR(D₂O) δ: 1.10(3H,d,J=7.3 Hz),1.28(3H,d,J=6.5 Hz),3.54 (1H,dd,J=3.0,5.9 Hz),3.68(1H,dq,J=7.2,9.6 Hz), 3.83 (4H,t,J=4.7 Hz),4.0–4.4(6H,m)

Example I-29

R¹ = H;    R² = Na;    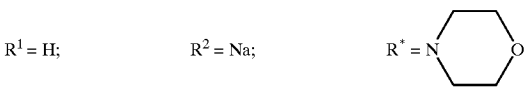

IR(KBr)cm⁻¹: 1799,1600,1419

¹H-NMR(D₂O) δ: 1.29(3H,d,J=6 Hz),3.04(1H,dd,J=16.5,8 Hz), 3.43(1H,dd,J=16.5,10 Hz),3.54(1H,m),3.84(4H, m),4.09 (2H,m),4.20–4.40(4H,m)

Example I-30

R¹ = Me;    R² = POM;    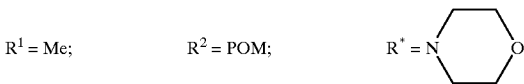

IR(KBr)cm⁻¹: 2972,1782,1751,1269,1115

¹H-NMR(CDCl₃) δ: 1.15(3H,d,J=7.6 Hz),1.21(9H,s),1.35 (3H,d, J=6.3 Hz),3.34(1H,dd,J=6.5,3.0 Hz),3.80(4H,t,J=5.0 Hz), 3.9–4.4(6H,m),4.43(1H,dd,J=10,3.0 Hz),5.82(1H,d,J=5.5 Hz),5.96(1H,d,J=5.5 Hz)

Example I-31

R¹ = Me;    R² = Na;    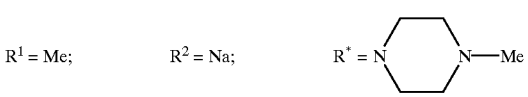

IR(KBr)cm⁻¹: 1757,1604,1389,1288

¹H-NMR(D₂O) δ: 1.12(3H,d,J=7.3 Hz),1.29(3H,d,J=6.4 Hz),2.32 (3H,s),2.64(4H,br),3.55(1H,dd,J=5.9,3.0 Hz),3.69 (1H,m),3.9–4.5(6H,m)

Example I-32

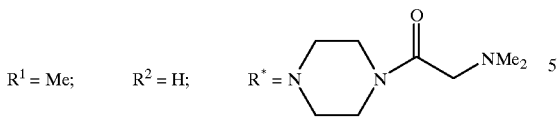

R¹ = Me; R² = H;

IR(KBr)cm⁻¹: 1760,1652,1602,1419,1375,1220
¹H-NMR(D₂O) δ: 1.10(3H,d,J=7.3 Hz),1.27(3H,d,J=6.2 Hz),2.94 (6H,s),3.50–3.56(1H,m),3.59–3.71(3H,m), 3.73–3.80(2H,m),4.10–4.49(6H,m),4.27(2H,s)

Example I-33

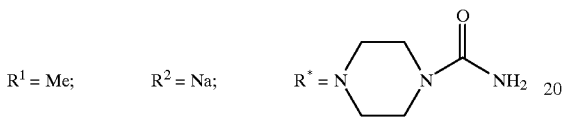

R¹ = Me; R² = Na;

IR(KBr)cm⁻¹: 1749,1646,1596,1419,1386
¹H-NMR(D₂O) δ: 1.09(3H,d,J=7.3 Hz),1.26(3H,d,J=6.3 Hz),3.57–3.74(6H,m),4.04–4.43(6H,m)

Example I-34

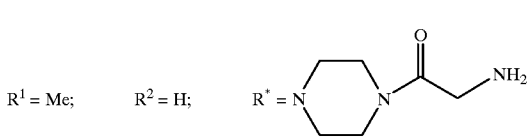

R¹ = Me; R² = H;

IR(KBr)cm⁻¹: 1758,1658,1604,1423,1382,1222
¹H-NMR(D₂O) δ: 1.09(3H,d,J=7.2 Hz),1.26(3H,d,J=6.2 Hz),3.50–3.59(1H,m),3.61–3.70(3H,m),3.70–3.78(2H,m), 4.05(2H, m),4.10–4.48(6H,m)

Example I-35

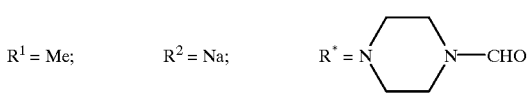

R¹ = Me; R² = Na;

IR(KBr)cm⁻¹: 1755,1659,1605,1394
¹H-NMR(D₂O) δ: 1.09(3H,d,J=7.3 Hz),1.27(3H,d,J=6.3 Hz),3.53 (1H,dd,J=6.0,3.0 Hz),3.65(5H,m),4.0–4.4(6H,m), 8.08 (1H,s)

Example I-36

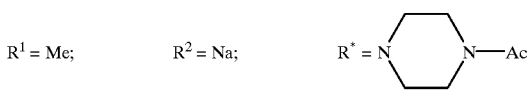

R¹ = Me; R² = Na;

IR(KBr)cm⁻¹: 1755,1618,1421
¹H-NMR(D₂O) δ: 1.19(3H,d,J=7.5 Hz),1.27(3H,d,J=6.6 Hz),2.14 (3H,s),3.53(1H,dd,J=6,3 Hz),3.6–3.9(5H,m), 4.0–4.4(6H, m)

Example I-37

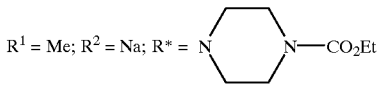

R¹ = Me; R² = Na; R* =

IR(KBr)cm⁻¹: 1757,1697,1608,1421,1220
¹H-NMR(D₂O) δ: 1.09(3H,d,J=7.3 Hz),1.23(6H,m),3.52 (1H,dd, J=5.9,3.0 Hz),3.64(5H,m),4.0–4.3(7H,m),4.36(1H, dd, J=9.6,3.0 Hz)

Example I-38

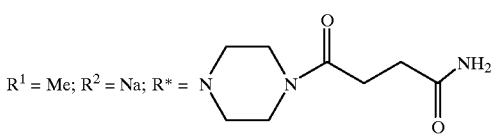

R¹ = Me; R² = Na; R* =

IR(KBr)cm⁻¹: 3403,2969,1754,1623,1564,1421,1081, 607
¹H-NMR(D₂O) δ: 1.08(3H,d,J=7.3 Hz),1.25(3H,d,J=6.4 Hz),2.52–2.75(4H,m),3.50–3.53(1H,m),3.64–4.37(11H,m)

Example I-39

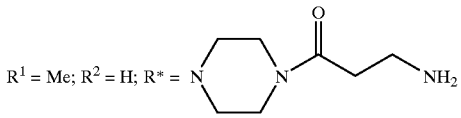

R¹ = Me; R² = H; R* =

IR(KBr)cm⁻¹: 3415,2967,1760,1629,1421,1382,1147, 1085
¹H-NMR(D₂O) δ: 1.08(3H,d,J=7.3 Hz),1.25(3H,d,J=6.3 Hz),2.84–3.28(4H,m),3.50–3.53(1H,m),3.63–4.37(11H,m)

Example I-40

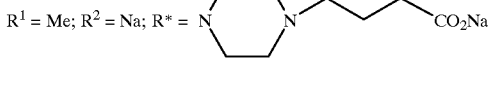

R¹ = Me; R² = Na; R* =

IR(KBr)cm⁻¹: 1749,1679,1650,1558
¹H-NMR(D₂O) δ: 1.08(3H,d,J=7.4 Hz),1.25(3H,d,J=6.3 Hz),2.38–2.48(2H,m),2.6–2.7(2H,m),3.52(1H,m),3.6–3.88 (5H,m), 3.92–4.38(6H,m)

Example I-41

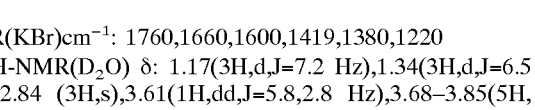

R¹ = Me; R² = H; R* =

IR(KBr)cm⁻¹: 1760,1660,1600,1419,1380,1220
¹H-NMR(D₂O) δ: 1.17(3H,d,J=7.2 Hz),1.34(3H,d,J=6.5 Hz),2.84 (3H,s),3.61(1H,dd,J=5.8,2.8 Hz),3.68–3.85(5H, m),4.21 (2H,s),4.20–4.42(4H,m),4.33(1H,quint,J=6.1 Hz), 4.44 (1H,dd,J=9.8,2.8 Hz),4.66–4.72(2H,m),5.73–5.81(1H, m)

Example I-42

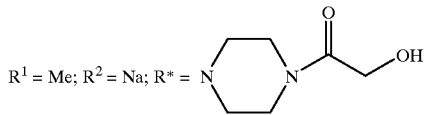

IR(KBr)cm$^{-1}$: 3424,1755,1650,1423,1392,1282,1223
$^1$H-NMR(D$_2$O) δ: 1.08(3H,d,J=7.5 Hz),1.25(3H,d,J=6.3 Hz),3.49–3.74(6H,m),4.03–4.37(8H,m)

Example I-43

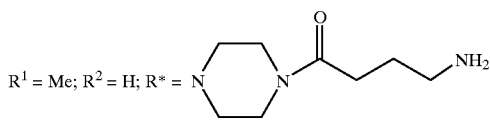

IR(KBr)cm$^{-1}$: 3164,1751,1690,1550,1417
$^1$H-NMR(D$_2$O) δ: 1.13(3H,d,J=6.3 Hz),1.30(3H,d,J=6.4 Hz),1.98 (2H,tt,J=7.5,8.1 Hz),2.62(2H,t,J=8.1 Hz),3.06(2H,t,J=7.5 Hz),3.55–3.58(1H,m),3.73–3.81(5H,m),4.26–4.42 (6H,m)

Example I-44

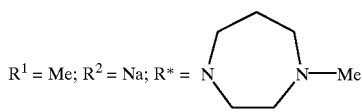

IR(KBr)cm$^{-1}$: 1749,1608,1387,1277
$^1$H-NMR(D$_2$O) δ: 1.10(3H,d,J=7.4 Hz),1.27(3H,d,J=6.3 Hz),2.20 (2H,m),2.66((3H,m),2.8–3.4(4H,m),3.54(1H,dd, J=3.0, 6.0 Hz),3.68(1H,m),4.0–4.4(6H,m)

Example I-45

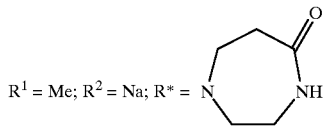

IR(KBr)cm$^{-1}$: 1756,1647,1612,1388
$^1$H-NMR(D$_2$O) δ: 1.08(3H,d,J=7.5 Hz),1.26(3H,d,J=6 Hz),2.90 (2H,m),3.45–3.75(4H,m),4.10–4.45(6H,m)

Example I-46

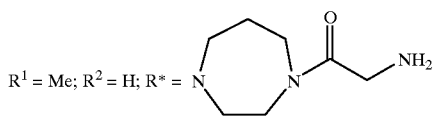

IR(KBr)cm$^{-1}$: 1770,1749,1650,1558
$^1$H-NMR(D$_2$O) δ: 1.07(3H,d,J=7.3 Hz),1.25(3H,d,J=6.5 Hz),1.66–2.18(2H,m),3.2–3.75(5H,m),3.75–4.15(6H,m), 4.15–4.46 (3H,m)

Example I-47

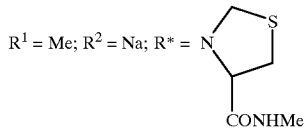

IR(KBr)cm$^{-1}$: 3408,1757,1660,1612,1566,1390
$^1$H-NMR(D$_2$O) δ: 1.03–1.20(3H,m),1.28(3H,d,J=6.5 Hz), 2.69–2.83(3H,m),3.18–3.80(4H,m),4.19–4.31(1H,m), 4.33–4.41(1H,m),{4.7–5.22(m),5.35–5.41(m)}(3H)

Example I-48

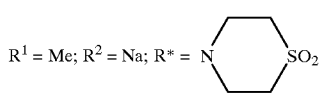

IR(KBr)cm$^{-1}$: 3390,1749,1608,1396,1284,1126
$^1$H-NMR(D$_2$O) δ: 1.10–1.37(6H,m),3.34–3.75(6H,m), 3.95–4.45(6H,m)

Example I-49

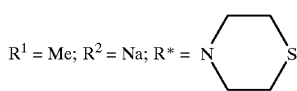

IR(KBr)cm$^{-1}$: 3421,1753,1608,1414,1392,1282
$^1$H-NMR(D$_2$O) δ: 1.16(3H,d,J=7.3 Hz),1.34(3H,d,J=6.3 Hz),2.80–2.95(4H,m),3.57–3.64(1H,m),3.67–3.83(1H,m), 4.25–4.75(6H,m)

Example I-50

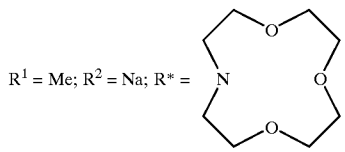

IR(KBr)cm$^{-1}$: 1756,1608,1388,1120
$^1$H-NMR(D$_2$O) δ: 1.06(3H,d,J=6.3 Hz),1.24(3H,d,J=5.9 Hz),3.49 (1H,s),3.67(9H,br s),3.91–4.00(4H,m),4.10–4.26 (5H,m), 4.26–4.36(1H,m)

Example I-51

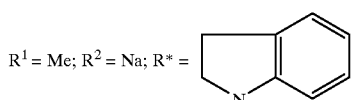

IR(KBr)cm$^{-1}$: 1749,1603,1387
$^1$H-NMR(D$_2$O) δ: 1.12(3H,d,J=7.3 Hz),1.26(3H,d,J=6.3 Hz),3.21 (2H,m),3.51(1H,br),4.22(1H,br),4.3–4.7(2H,m), 7.23 (2H,m),7.37(1H,m)

Example I-52

R¹ = Me; R² = Na; R* = 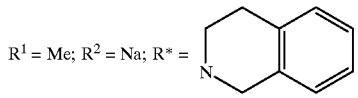

IR(KBr)cm⁻¹: 3396,1745,1548
¹H-NMR(D₂O) δ: 0.79–0.99(3H,m),1.00–1.08(3H,m), 2.73–2.85(2H,m),3.23–3.33(1H,m),3.32–3.51(1H,m), 3.75–4.18(4H,m),4.64–5.08(1H,m),4.98–5.05(1H,m), 6.99–7.14(1H,m)

Example I-53

R¹ = Me; R² = Na; R* = 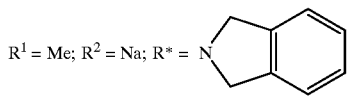

IR(KBr)cm⁻¹: 1751,1597,1419,1387
¹H-NMR(D₂O) δ: 1.12(3H,d,J=7.3 Hz),1.28(3H,d,J=6.3 Hz),3.54 (1H,dd,J=5.9,3.0 Hz),3.77(1H,m),4.26(1H,m),4.37 (1H, dd,J=10,3.0 Hz),4.98(4H,m),7.34(4H,s)

Example I-54

R¹ = Me; R² = Na; R* = 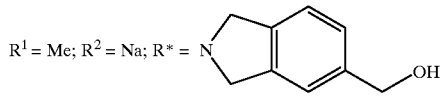

IR(KBr)cm⁻¹: 3419,1757,1601,1566,1423,1394
¹H-NMR(D₂O) δ: 1.18(3H,d,J=7.3 Hz),1.32(3H,d,J=6.6 Hz),3.60 (1H,m),3.87(1H,m),4.33(1H,m),4.41(1H,m),4.65 (2H,d,J=6.2 Hz),4.88–5.12(4H,m),7.36(3H,s)

Example I-55

R¹ = Me; R² = Na; R* = 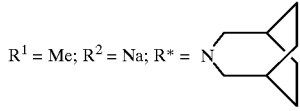

IR(KBr)cm⁻¹: 1749,1600,1394
¹H-NMR(D₂O) δ: 1.11(3H,d,J=7.3 Hz),1.27(3H,d,J=6.5 Hz),1.68 (8H,s),2.16(2H,br s),3.51(1H,dd,J=6.0,2.9 Hz), 3.71(1H, m),4.02(1H,dd,J=14,3.5 Hz),4.1–4.4(4H,m),4.55 (1H,dd,J=13.5,5.3 Hz)

Example I-56

R¹ = Me; R² = Na; R* = 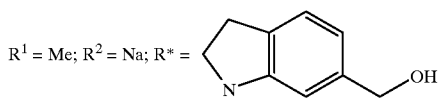

IR(KBr)cm⁻¹: 1747,1691,1610,1272
¹H-NMR(D₂O) δ: 1.10(3H,d,J=7 Hz),1.24(3H,br d,J=6.5 Hz), 3.13(2H,m),3.49(1H,m),4.21(1H,m),4.30–4.60(5H,m), 7.16 (1H,d,J=8 Hz),7.32(1H,d,J=8 Hz)

Example I-57

R¹ = Me; R² = Na; R* = 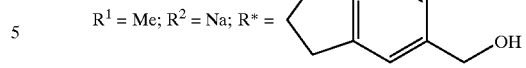

IR(KBr)cm⁻¹: 1755,1601,1389
¹H-NMR(D₂O) δ: 1.10(3H,d,J=7.3 Hz),1.25(3H,d,J=5.9 Hz),2.9–3.8(4H,m),4.0–4.5(4H,m),4.56(2H,s),7.15(1H,d,J= 8.9 Hz),7.29(1H,s),9.0(1H,br s)

Example I-58

R¹ = Me; R² = Na; R* = 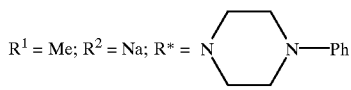

IR(KBr)cm⁻¹: 1792,1749,1601,1387,1228
¹H-NMR(D₂O) δ: 1.11(3H,d,J=7.5 Hz),1.28(3H,d,J=6.3 Hz),3.32 (4H,br),3.53(1H,dd,J=3,6 Hz),3.70(1H,m),4.0–4.6 (6H,m), 7.0–7.2(3H,m),7.40(2H,m)

Example I-59

R¹ = Me; R² = Na; R* = 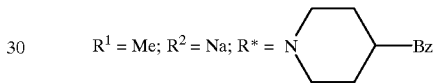

IR(KBr)cm⁻¹: 1749,1606,1554
¹H-NMR(D₂O) δ: 1.09(3H,d,J=3.9 Hz),1.28(3H,d,J=6.4 Hz),1.70–1.83(2H,m),1.90(1H,br s),2.61(2H,d,J=7.4 Hz), 3.12–3.23(1H,m),3.31–3.41(1H,m),3.12(1H,dd,J=2.6,2.9 Hz),3.62–3.74(1H,m),4.35(1H,dd,J=2.6,2.9 Hz),5.21(1H,br d,J=12.9 Hz),7.27–7.29(2H,m),7.34–7.39(3H,m)

Example I-60

R¹ = Me; R² = Na; R* = 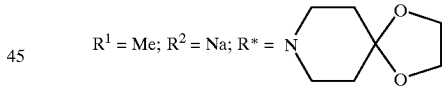

IR(KBr)cm⁻¹: 1757,1606,1427,1388
¹H-NMR(D₂O) δ: 1.11(3H,d,J=7.5 Hz),1.27(3H,d,J=6.5 Hz),1.90 (4H,m),3.53(1H,dd,J=6,3 Hz),3.68(1H,m), 4.05–4.40(10H, m)

Example I-61

R¹ = Me; R² = H; R* = 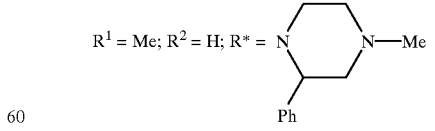

IR(KBr)cm⁻¹: 3400,1757,1605,1418,1387,1286
¹H-NMR(D₂O) δ: 1.12(3H,br d),1.26(3H,d,J=7 Hz),2.25 (3H, br s),2.35(1H,m),2.64(1H,m),2.72(1H,m),3.45(1H,m), 3.50(1H,m),3.70(3H,m),4.22(1H,m),4.34(1H,m),7.20(2H, m),7.3–7.5(3H,m)

Example I-62

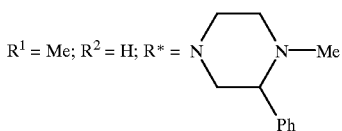

IR(KBr)cm$^{-1}$: 3400,1750,1608,1420,1390,1250
$^1$H-NMR(D$_2$O) δ: 1.06(3H,m),1.26(3H,m),2.02(3H,s), 2.50(2H, m),3.06(2H,m),3.2–3.8(5H,m),4.20(1H,m),4.35(1H,m), 7.40(5H,m)

Example I-63

R$^1$=Me; R$^2$=Na; R*=NMe$_2$
IR(KBr)cm$^{-1}$: 1749,1603,1387,1248,1147
$^1$H-NMR(D$_2$O) δ: 1.10(3H,d,J=7.3 Hz),1.28(3H,d,J=6.3 Hz),3.47 (3H,s),3.48(3H,s),3.53(1H,dd,J=3,6 Hz),3.71(1H,m),4.26 (1H,m),4.36(1H,dd,J=3,10 Hz)

Example I-64

R$^1$=Me; R$^2$=H; R*=NEt$_2$
IR(KBr)cm$^{-1}$: 1768,1606,1558,1413,1379,1267
$^1$H-NMR(D$_2$O) δ: 1.16(3H,d,J=7.3 Hz),1.26–1.43(9H,m), 3.56–3.61(1H,m),3.73–4.18(5H,m),4.26–4.38(1H,m), 4.39–4.45 (1H,m)

Example I-65

R$^1$=H; R$^2$=Na; R*=NMe$_2$
IR(KBr)cm$^{-1}$: 1801,1600,1373
$^1$H-NMR(D$_2$O) δ: 1.24(3H,d,J=6.5 Hz),2.97(1H,dd,J=15,9 Hz), 3.25–3.50(8H,m),4.15–4.35(2H,m)

Example I-66

R$^1$=Me; R$^2$=POM; R*=NMe$_2$
IR(KBr)cm$^{-1}$: 2972,1782,1751,1271,1115
$^1$H-NMR(CDCl$_3$) δ: 1.14(3H,d,J=7.5 Hz),1.21(9H,s),1.35 (3H,d, J=6.3 Hz),3.33(1H,dd,J=6.6,3.0 Hz),3.47(3H,s),3.50 (3H,s),4.00(1H,m),4.28(1H,m),4.41(1H,dd,J=10,3.0 Hz), 5.82 (1H,d,J=5.4 Hz),5.96(1H,d,J=5.4 Hz)

Example I-67

R$^1$=Me; R$^2$=Na; R*=N(i-Pr)$_2$
IR(KBr)cm$^{-1}$: 3373,2970,1763,1601,1387
$^1$H-NMR(D$_2$O) δ: 1.14(3H,d,J=7.7 Hz),1.31(3H,d,J=6.7 Hz),1.3–1.9(12H,m),3.54(1H,dd,J=5.9,2.6 Hz),3.71–3.86 (1H,m), 4.23–4.34(1H,m),4.38(1H,dd,J=9.0,2.6 Hz)

Example I-68

R$^1$=Me; R$^2$=Na; R*=N(n-Bu)$_2$
IR(KBr)cm$^{-1}$: 3419,2958,1751,1608,1387,1290
$^1$H-NMR(D$_2$O) δ: 0.88–1.00(6H,m),1.14(3H,d,J=7.3 Hz), 1.31 (3H,d,J=6.3 Hz),1.19–1.48(4H,m),1.63–1.86(4H,m), 3.47–3.56(1H,m),3.60–4.08(5H,m),4.20–4.42(2H,m)

Example I-69

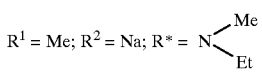

IR(KBr)cm$^{-1}$: 3425,1757,1603,1389,1282
$^1$H-NMR(D$_2$O) δ: 1.11(3H,d,J=6.9 Hz),1.21(3H,t,J=6.9 Hz),1.28 (3H,d,J=6.3 Hz),{3.43(s),3.45(s)}(3H),3.50–3.55 (1H, m),3.65–3.79(1H,m),3.80–4.12(2H,m),4.20–4.32(1H, m),4.33–4.40(1H,m)

Example I-70

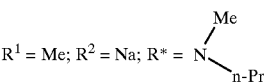

IR(KBr)cm$^{-1}$: 3407,1757,1604,1389,1267
$^1$H-NMR(D$_2$O) δ: {0.89(t,J=7.3 Hz),0.93(t,J=7.3 Hz)} (3H),1.10 (3H,d,J=7.3 Hz),1.28(3H,d,J=6.5 Hz),1.62–1.84 (2H,m), 3.44(3H,s),3.49–3.54(1H,m),3.66–3.79(1H,m), 3.80–4.06(2H,m),4.20–4.31(1H,m),4.32–4.39(1H,m)

Example I-71

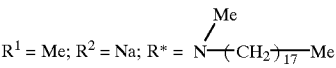

IR(KBr)cm$^{-1}$: 3419,2920,2851,1757,1608,1394
$^1$H-NMR(D$_2$O) δ: 0.86–0.97(3H,m),1.0–1.9(38H,m), 3.2–4.5(9H,m)

Example I-72

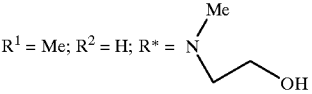

IR(KBr)cm$^{-1}$: 1749,1608,1506,1386,1279
$^1$H-NMR(D$_2$O) δ: 1.16(3H,dd,J=2.3,7.3 Hz),1.33(3H,d, J=6.3 Hz), 3.55(3H,d,J=2.3 Hz),3.01–3.11(1H,m),3.91–3.98 (2H,m),4.09–4.15(1H,m),4.20–4.37(2H,m),4.38–4.45(1H, m)

Example I-73

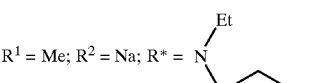

IR(KBr)cm$^{-1}$: 3374,1753,1604,1308
$^1$H-NMR(D$_2$O) δ: {1.07(d,J=5.9 Hz),1.09(d,J=5.9 Hz)} (3H), {1.22(t,J=7.2 Hz),1.31(t,J=7.2 Hz)}(3H),1.26(3H,d,J= 6.4 Hz),3.65–3.80(1H,m),3.51(1H,m),3.85–4.18(6H,m), 4.24(1H,dq,J=6.2,6.2 Hz),4.31–4.39(1H,m)

Example I-74

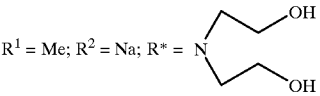

IR(KBr)cm$^{-1}$: 3386,1749,1608,1396,1072
$^1$H-NMR(D$_2$O) δ: 1.09(3H,d,J=7.3 Hz),1.27(3H,d,J=6.3 Hz), 3.47–3.54(1H,m),3.65–4.29(10H,m),4.31–4.38(1H,m)

Example I-75

$R^1$ = Me; $R^2$ = Na; $R^*$ = 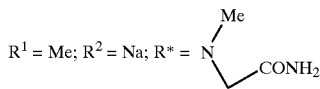

IR(KBr)cm$^{-1}$: 3391,1751,1680,1605,1390,1277
$^1$H-NMR(D$_2$O) δ: {1.12(d,J=7.4 Hz),1.16(d,J=7.4 Hz)}(3H),1.32 (3H,d,J=6.3 Hz),3.56(3H,s),3.52–3.60(1H,m),3.67–3.80 (1H,m),4.25–4.35(1H,m),4.41(1H,dd,J=9.7,3.0 Hz),4.46–4.48(2H,m)

Example I-76

$R^1$ = Me; $R^2$ = Na; $R^*$ = 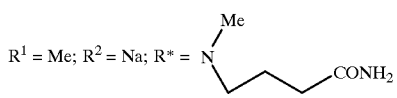

IR(KBr)cm$^{-1}$: 3390,1751,1674,1612,1392
$^1$H-NMR(D$_2$O) δ: 1.15(3H,d,J=7.3 Hz),1.33(3H,d,J=6.3 Hz),2.00–2.18(2H,m),2.32–2.48(2H,m),3.48(3H,s),3.58 (1H,dd,J=5.8,2.9 Hz),3.70–3.82(1H,m),3.84–4.20(2H,m),4.25–4.48 (2H,m)

Example I-77

$R^1$ = Me; $R^2$ = Na; $R^*$ = 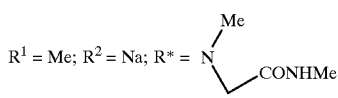

IR(KBr)cm$^{-1}$: 3417,1753,1657,1606,1564,1389,1279
$^1$H-NMR(D$_2$O) δ: {1.11(d,J=7.2 Hz),1.16(d,J=7.2 Hz)}(3H),1.32 (3H,d,J=6.3 Hz),{2.78(s),2.81(s),2.83(s)}(3H),3.56(3H, s),3.52–3.60(1H,m),3.68–3.79(1H,m),4.25–4.35 (1H,m),4.41(1H,dd,J=9.5,2.9 Hz),4.60–4.90(2H,m)

Example I-78

$R^1$ = Me; $R^2$ = Na; $R^*$ = 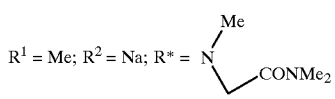

IR(KBr)cm$^{-1}$: 3419,1753,1647,1392,1279
$^1$H-NMR(D$_2$O) δ: {1.11(d,J=7.3 Hz),1.17(d,J=7.3 Hz)}(3H),1.32 (3H,d,J=6.3 Hz),{2.98(s),3.02(s)}(3H),{3.09(s),3.10 (s)}(3H),{3.51(s),3.53(s)}(3H),3.52–3.60(1H,m),3.70–3.82(1H,m),4.25–4.35(1H,m),4.40(1H,dd,J=9.8,2.9 Hz), 4.73(1H,d,J=16.5 Hz),5.10(1H,d,J=16.5 Hz)

Example I-79

$R^1$ = Me; $R^2$ = Na; $R^*$ = 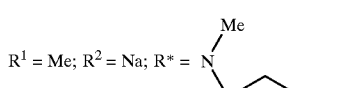

IR(KBr)cm$^{-1}$: 1770,1747,1679,1540
$^1$H-NMR(D$_2$O) δ: 1.07(3H,dd,J=3.3,17.3 Hz),1.25(3H,d,J=6.3 Hz),1.86–1.98(3H,m),3.3–3.76(7H,m),3.86–4.4(4H,m)

Example I-80

$R^1$ = Me; $R^2$ = Na; $R^*$ = 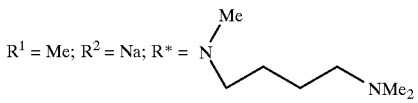

IR(KBr)cm$^{-1}$: 3423,1761,1605,1387
$^1$H-NMR(D$_2$O) δ: 1.16(3H,d,J=7.3 Hz),1.33(3H,d,J=6.6 Hz),1.70–1.94(4H,m),2.90(3H,s),2.92(3H,s),3.15–3.30(2H,m), 3.49(3H,s),3.55–3.62(1H,m),3.68–4.38(4H,m),4.42(1H,dd,J=9.5,2.3 Hz)

Example I-81

$R^1$ = Me; $R^2$ = Na; $R^*$ = 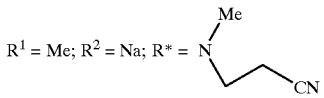

IR(KBr)cm$^{-1}$: 3429,1755,1612,1390,1275,1097
$^1$H-NMR(D$_2$O) δ: 1.08(3H,d,J=7.3 Hz),1.25(3H,d,J=6.3 Hz),2.93–2.99(2H,m),3.37–3.75(5H,m),4.18–4.39(4H,m)

Example I-82

$R^1$ = Me; $R^2$ = Na; $R^*$ = 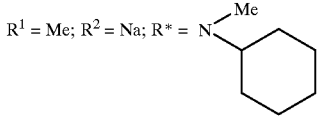

IR(KBr)cm$^{-1}$: 1756,1600,1394
$^1$H-NMR(D$_2$O) δ: 1.09(3H,m),1.26(3H,d,J=6.5 Hz), 1.30–1.90 (10H,m),{3.30(s),3.34(s)}(3H),3.51(1H,m),3.69 (1H,m), 4.24(1H,m),4.34(1H,m)

Example I-83

$R^1$ = Me; $R^2$ = Na; $R^*$ = 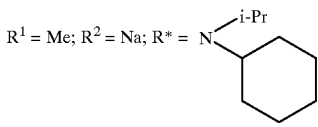

$^1$H-NMR(D$_2$O) δ: 0.7–1.9(16H,m),1.14(3H,d,J=7.3 Hz), 1.31 (3H,d,J=6.3 Hz),3.49–3.58(1H,m),3.65–3.90(1H,m), 4.21–4.44(2H,m)

Example I-84

$R^1$ = Me; $R^2$ = Na; $R^*$ = 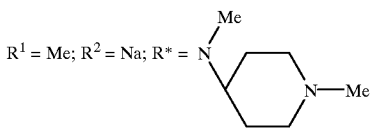

IR(KBr)cm$^{-1}$: 1761,1604,1465
$^1$H-NMR(D$_2$O) δ: 1.08(3H,d,J=7 Hz),1.26(3H,d,J=6.5 Hz),2.07 (4H,m),2.84(3H,s),3.15(2H,m),3.31(3H,br s),3.50–3.70 (4H,m),4.24(1H,m),4.36(1H,br d,J=10 Hz), 5.63(1H,m)

Example I-85

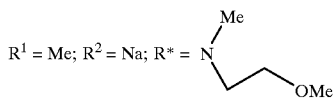

IR(KBr)cm$^{-1}$: 1749,1605,1387,1288,1109

$^1$H-NMR(D$_2$O)δ: 1.10(3H,d,J=7.3 Hz),1.27(3H,d,J=6.3 Hz),{3.67 (s),3.40(s)}(3H),3.47(3H,s),3.53(1H,dd,J=6.0,3.0 Hz), 3.70(1H,m),3.78(2H,q,J=4.9 Hz),4.11(1H,m),4.25(2H,m), 4.35(1H,d,J=9.6 Hz)

Example I-86

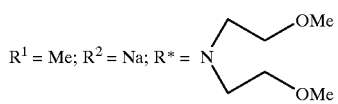

IR(KBr)cm$^{-1}$: 1770,1608,1402,1281,1115

$^1$H-NMR(D$_2$O) δ: 1.10(3H,d,J=7.3 Hz),1.28(3H,d,J=6.3 Hz),3.36 (3H,s),3.40(3H,s),3.53(1H,dd,J=6.0,3.0 Hz),3.81 (4H, m),4.0–4.3(5H,m),4.36(1H,dd,J=10,3.0 Hz)

Example I-87

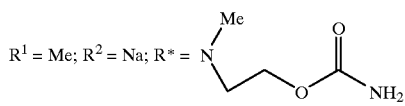

IR(KBr)cm$^{-1}$: 3398,1749,1608,1389,1333,1281,1086

$^1$H-NMR(D$_2$O) δ: 1.14(3H,d,J=7.3 Hz),1.31(3H,d,J=6.5 Hz), {3.51(s),3.52(s)}(3H),3.5–3.59(1H,m),3.66–3.82(1H,m),4.00–4.18(1H,m),4.21–4.53(5H,m)

Example I-88

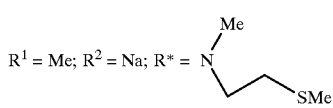

IR(KBr)cm$^{-1}$: 3394,1749,1608,1392

$^1$H-NMR(D$_2$O) δ: 1.14(3H,d,J=6.9 Hz),1.31(3H,d,J=6.3 Hz), {2.19(s),2.22(s)}(3H),2.84–3.00(2H,m),{3.50(s), 3.51(s)}(3H),3.56(1H,dd,J=6.0,2.9 Hz),3.70–3.83(1H,m),{3.84–3.91(m),4.11–4.43(m)}(4H)

Example I-89

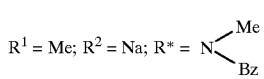

IR(KBr)cm$^{-1}$: 1749,1608,1387

$^1$H-NMR(D$_2$O) δ: {1.02(d,J=7.3 Hz),1.12(d,J=7.3 Hz)}(2H),1.27 (3H,d,J=6.3 Hz),{3.44(s),3.47(s)}(3H),3.52(1H,m),3.74 (1H,m),4.25(1H,m),4.35(1H,m),5.0–5.4(2H,m), 7.2–7.5 (5H,m)

Example I-90

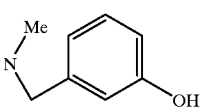

IR(KBr)cm$^{-1}$: 3409,1751,1596,1562,1392

$^1$H-NMR(D$_2$O) δ: {1.00(d,J=7.3 Hz),1.11(d,J=7.3 Hz)}(3H),1.27 (3H,d,J=6.2 Hz),{3.42(s),3.46(s)}(3H),3.48–3.55 (1H,m), 3.67–3.74(1H,m),4.22–4.27(1H,m),4.33–4.37(1H,m), 5.06–5.30(2H,m),6.78–6.86(3H,m),7.25–7.33(1H,m)

Example I-91

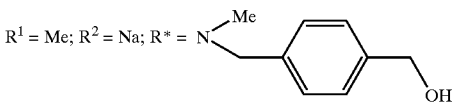

IR(KBr)cm$^{-1}$: 3421,1735,1602,1390

$^1$H-NMR(D$_2$O) δ: 0.99–1.13(3H,m),1.25–1.28(3H,m), 3.34–3.76(5H,m),4.22–4.35(2H,m),4.56–4.66(2H,m), 5.13–5.32(2H,m),7.28–7.43(4H,m)

Example I-92

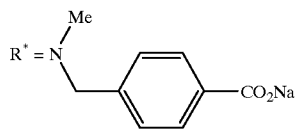

IR(KBr)cm$^{-1}$: 3425,1749,1597,1558,1390

$^1$H-NMR(D$_2$O) δ: 0.96–1.14(3H,m),1.25–1.28(3H,m), 3.45–3.76(5H,m),4.21–4.38(2H,m),5.05–5.51(2H,m), 7.28–7.35(2H,m),7.82–7.90(2H,m)

Example I-93

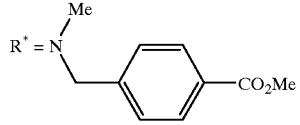

IR(KBr)cm$^{-1}$: 3413,1753,1722,1610,1564,1390,1282

$^1$H-NMR(D$_2$O) δ: 0.94–1.14(3H,m),1.23–1.30(3H,m), 3.46–3.75(5H,m),3.90(3H,s),4.21–4.38(2H,m),5.19–5.45 (2H,m),7.36–7.40(2H,m),7.96–8.05(2H,m)

Example I-94

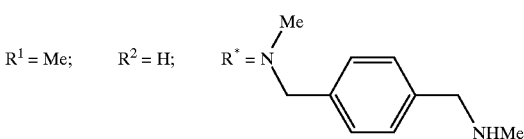

IR(KBr)cm$^{-1}$: 3434,1759,1691,1387,1092

$^1$H-NMR(D$_2$O) δ: 0.95–1.10(3H,m),1.23(3H,d,J=6.3 Hz), 2.66 (3H,s),3.31–3.73(5H,m),4.12–4.32(4H,m),5.10–5.35 (2H, m),7.29–7.42(4H,m)

Example I-95

R¹ = Me;   R² = Na;   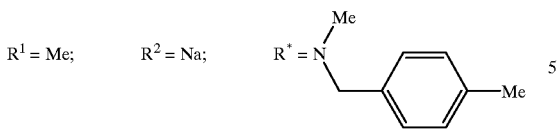

IR(KBr)cm⁻¹: 3426,1747,1691,1389,1092

¹H-NMR(D₂O) δ: 0.90–1.22(6H,m),2.15–2.21(3H,m), 3.27–4.29(7H,m),4.80–5.37(2H,m),7.00–7.18(4H,m)

Example I-96

R¹ = Me;   R² = Na;   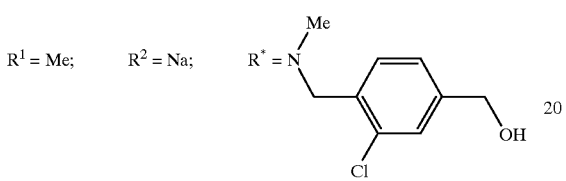

IR(KBr)cm⁻¹: 3392,1764,1753,1610,1390,1093

¹H-NMR(D₂O) δ: {0.94(d,J=6.9 Hz),1.11(d,J=7.3 Hz)} (3H),1.24 (3H,d,J=7.2 Hz),3.43(3H,s),3.50–3.53(1H,m), 3.69–3.74 (1H,m),4.19–4.27(1H,m),4.29–4.35(1H,m), 4.56–4.58(2H, m),5.14–5.38(2H,m),7.09–7.16(1H,m), 7.24–7.30(1H,m), 7.43–7.46(1H,m)

Example I-97

R¹=Me; R²=Na; R*=NBz₂
IR(KBr)cm⁻¹: 3423,1757,1605,1390,1219
¹H-NMR(D₂O) δ: 0.98(3H,d,J=7.1 Hz),1.26(3H,d,J=6.3 Hz),3.48 (1H,m),3.76(1H,m),4.26(1H,m),4.31(1H,m),5.02 (2H,br s),5.17(2H,m),7.10–7.47(10H,m)

Example I-98

R¹ = Me;   R² = Na;   

IR(nujor)cm⁻¹: 1754,1600

¹H-NMR(D₂O) δ: {0.98(d,J=7.2 Hz),1.11(d,J=7.2 Hz)} (3H),1.25 (3H,d,J=6.4 Hz),1.97(2H,m),3.49(1H,m),3.60 (2H,m),3.71 (1H,m),3.83(1H,m),4.04(1H,m),4.21(1H,m), 4.32(1H,M),5.14(2H,M),7.33(5H,M)

Example I-99

R¹ = Me;   R² = H;   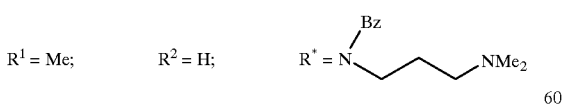

IR(nujor)cm⁻¹: 1754,1600

¹H-NMR(D₂O) δ: 1.29(3H,d,J=6.3 Hz),(1.85(s),1.93(s)1 (3H), 2.79(6H,S),2.10(2H,m),3.10(2H,m),3.37(1H,m),3.83 (1H, m),4.00(1H,m),4.26(2H,m),4.59(1H,br s),5.18(2H,m), 7.33(5H,m)

Example I-100

R¹ = Me;   R² = Na;   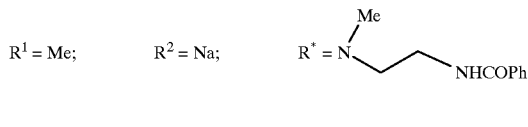

IR(KBr)cm⁻¹: 1749,1650,1540,1394

¹H-NMR(D₂O) δ: 0.58–0.72 (3H,m) 1.15–1.28 (3H,m) 3.04–3.6(6H,m),3.65–4.38(6H,m),7.42–7.63(3H,m), 7.65–7.8(2H,m)

Example I-101

R¹ = Me;   R² = Na;   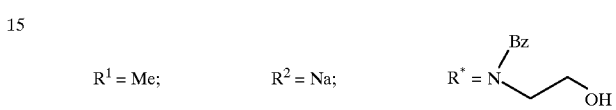

IR(KBr)cm⁻¹: 1751,1606,1396

¹H-NMR(D₂O) δ: 1.11(3H,d,,J=7.3 Hz),1.25(3H,d,J=6.3 Hz),3.46–3.52(1H,M),3.69–3.75(1H,m),3.84–3.97(3H,m), 4.07–4.11(1H,m),4.20–4.25(1H,m),4.31–4.34(1H,m), 5.20–5.26 (1H,m),5.41–5.46(1H,m),7.23–7.45(5H,m)

Example I-102

R¹ = Me;   R² = Na;   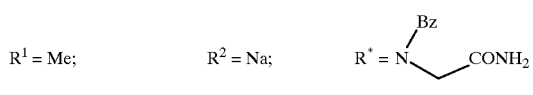

IR(KBr)cm⁻¹: 1764,1751,1681,1608,1392

¹H-NMR(D₂O) δ: 1.04(3H,d,J=7.3 Hz),1.25(3H,d,J=6.4 Hz),3.49–3.51(1H,m),3.64–3.73(1H,m),4.21–4.25(1H,m), 4.34(1H,d,J=9.6 Hz),4.53–4.64(2H,m),5.17(2H,s), 7.32–7.45(5H,m)

Example I-103

R¹ = Me;   R² = Na;   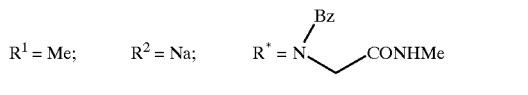

IR(KBr)cm⁻¹: 1767,1749,1678,1651,1618,1560,1550, 1392

¹H-NMR(D₂O) δ: 1.02(3H,d,J=7.0 Hz),1.24(3H,d,J=6.5 Hz), 2.63–2.67(5H,m),3.48–3.51(1H,m),3.66–3.72(1H,m), 4.31–4.35(1H,m),4.53–4.59(1H,m),5.09–5.16(2H,m), 7.30–7.42(5H,m)

Example I-104

R¹ = Me;   R² = Na;   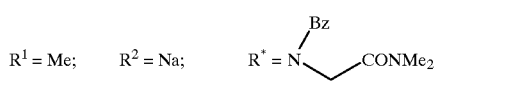

IR(KBr)cm⁻¹: 1751,1647,1394,1142

¹H-NMR(D₂O) δ: 1.06(3H,d,J=7.3 Hz),1.25(3H,d,J=6.3 Hz),2.89–2.95(6H,m),3.50(1H,dd,J=5.7,2.8 Hz),3.68–3.74 (1H,m), 4.21–4.25(1H,m),4.30–4.34(1H,m),4.65–4.75(2H, m),4.86–5.08(1H,m),5.20–5.28(1H,m),7.25–7.47(5H,m)

Example I-105

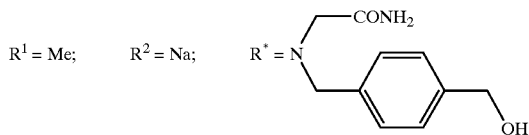

IR(KBr)cm$^{-1}$: 3394,1753,1682,1614,1392

$^1$H-NMR(D$_2$O) δ: 1.05–1.22(3H,m),1.32(3H,d,J=6.2 Hz), 3.53–3.62(1H,m),3.65–3.83(1H,m),4.24–4.44(2H,m), 4.60–4.70(4H,m),5.24(2H,s),7.31–7.51(4H,m)

Example I-106

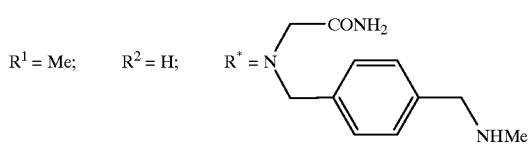

IR(KBr)cm$^{-1}$: 3398,1759,1678,1601,1385,1223

$^1$H-NMR(D$_2$O) δ: {1.07(d,J=7.3 Hz),1.12(d,J=7.3 Hz)}(3H),1.30 (3H,d,J=6.3 Hz),2.74(3H,s),3.51–3.60(1H,m), 3.65–3.80 (1H,m),4.18–4.40(4H,m),4.60–4.8(2H,m), 5.10–5.63(2H,m),7.36–7.57(4H,m)

Example I-107

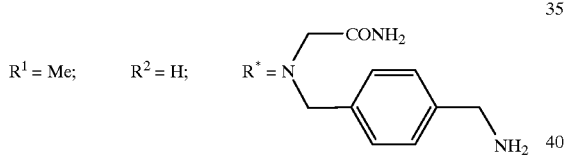

IR(KBr)cm$^{-1}$: 3409,1761,1682,1605,1387,1223,1092

$^1$H-NMR(D$_2$O) δ: {1.05(d,J=7.3 Hz),1.09(d,J=7.3 Hz)}(3H),1.27 (3H,d,J=6.3 Hz),3.48–3.56(1H,m),3.63–3.76(1H,m),4.18 (2H,s),4.1–4.48(2H,m),4.50–4.9(2H,m),{5.10(d,J=16.7 Hz),5.12(d,J=16.7 Hz),5.28(d,J=16.7 Hz),5.56(d,J=16.7 Hz)}(2H),7.31–7.50(4H,m)

Example I-108

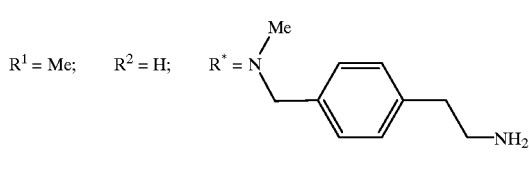

IR(KBr)cm$^{-1}$: 3377,2964,1757,1603,1387,1078

$^1$H-NMR(D$_2$O) δ: {1.07(d,J=7.6 Hz),1.10(d,J=7.6 Hz)}(3H),1.25 (3H,d,J=6.3 Hz),2.92–3.01(2H,m),3.19–3.28(2H,m),3.38– 3.54(1H,m),{3.43(s),3.47(s)}(3H),3.62–3.74(1H,m), 4.28–4.39(2H,m),5.07–5.38(2H,m),7.23–7.39(4H,m)

Example I-109

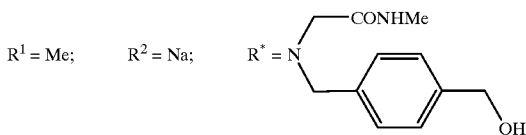

IR(KBr)cm$^{-1}$: 3413,1753,1674,1610,1564,1394

H-NMR(D$_2$O) δ: 1.01–1.14(3H,m),1.27(3H,d,J=6.0 Hz), 2.64–2.77(3H,m),3.50–3.56(1H,m),3.62–3.82(1H,m), 4.19–4.41(2H,m),4.53–4.75(4H,m),{5.12–5.23(m), 5.45–5.59(m)}(2H),7.29–7.48(4H,m)

Example I-110

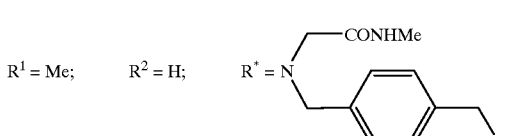

IR(KBr)cm$^{-1}$: 3413,1755,1657,1564,1388,1223

$^1$H-NMR(D$_2$O) δ: 0.9–1.17(3H,m),1.25(3H,d,J=6.3 Hz), 2.52–2.80(3H,m),3.48–3.77(2H,m),4.10–4.41(4H,m), 4.52–4.7(2H,m),{5.02–5.32(m),5.52–5.62(m)}(2H), 7.29–7.55(4H,m)

Example I-111

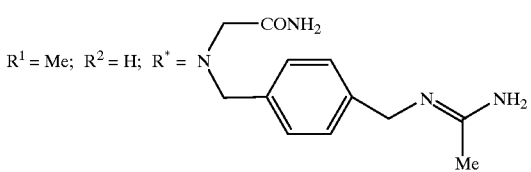

IR(KBr)cm$^{-1}$: 3412,1759,1682,1645,1599,1566,1392

$^1$H-NMR(D$_2$O) δ: 1.02–1.12(3H,m),1.27(3H,d,J=6.3 Hz), 2.26 (3H,s),3.49–3.57(1H,m),3.64–3.77(1H,m),4.20–4.40 (2H,m),4.48–4.52(2H,m),{4.53–5.35(m),5.54–5.63 (m)}(4H),7.31–7.43(4H,m)

Example I-112

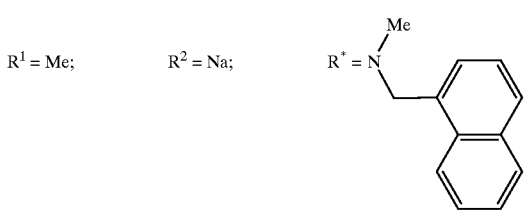

IR(KBr)cm$^{-1}$: 3406,1753,1603,1389

$^1$H-NMR(D$_2$O) δ: 0.64–0.92(3H,m),1.09–1.15(3H,m), 3.04–3.74(5H,m),4.11–4.25(2H,m),4.83–5.63(2H,m), 6.96–7.80(7H,m)

Example I-113

R¹ = Me;   R² = Na;   R* = 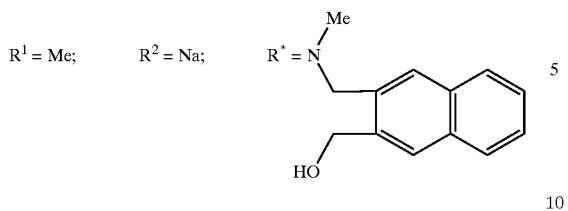

IR(nujor)cm⁻¹: 1754,1600

¹H-NMR(D₂O) δ: 0.81(1H,m),1.20(5H,m),3.30(2H,m),{3.49(s), 3.56(s)}(3H),4.24(3H,m),5.41(4H,m),7.51(3H,m), 7.89 (3H,m)

Example I-114

R¹ = Me;   R² = Na;   R* = 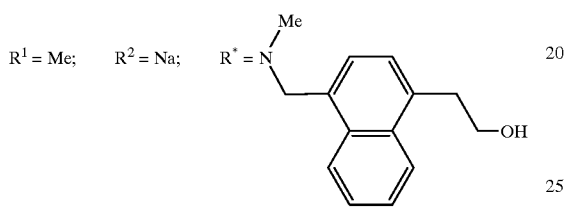

IR(nujor)cm⁻¹: 1754,1600

¹H-NMR(DMSO-d₆+D₂O) δ: 0.98(3H,m),1.11(3H,m), 3.19(3H,m), {3.28(s),3.42(s)}(3H),3.66(3H,m),4.04(2H,m), 5.58(2H, m),7.08(1H,m),7.35(1H,m),7.57(2H,m),7.98(1H, m),8.11 (1H,m)

Example I-115

R¹ = Me;   R² = Na;   R* = 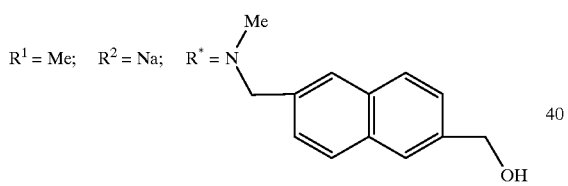

IR(nujor)cm⁻¹: 1751,1604

¹H-NMR(D₂O) δ: {0.71(d,J=7.3 Hz),0.89(d,J=7.0 Hz)}(3H),1.08 (3H,d,J=6.5 Hz),{3.25(s),3.30(s)}(3H),3.31(1H, m),3.52(1H,m),4.06(1H,m),4.12(1H,m),5.11(4H,m),7.23 (1H,d,J=9.0 Hz),7.35(1H,dd,J=7.9,7.9 Hz),7.51(1H,s),7.67 (3H,m)

Example I-116

R¹ = Me;   R² = H;   R* = 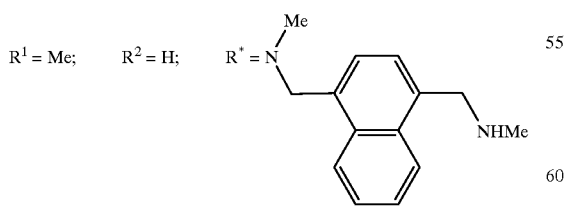

IR(KBr)cm⁻¹: 1760,1600

¹H-NMR(DMSO-d₆+D₂O) δ: 0.93(3H,m),1.11(3H,m), 2.62(3H,s), 3.09–4.13(4H,m),4.50(2H,m),5.64(2H,m),7.16 (1H,m), 7.61(3H,m),8.07(1H,m),8.19(1H,m)

Example I-117

R¹ = Me;   R² = H;   R* = 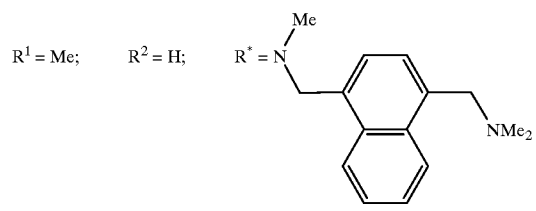

IR(KBr)cm⁻¹: 1754,1600

¹H-NMR(DMSO-d₆+D₂O) δ: {0.90(d,J=7.0 Hz),1.03(d, J=7.5 Hz)}(3H),1.12(3H,m),2.49(6H,s),{3.30(s),3.50(s)} (3H),3.16–4.18(4H,m),4.28(2H,m),5.67(2H,m),7.17(1H, m),7.58 (3H,m),8.02(1H,m),8.30(1H,m)

Example I-118

R¹ = Me;   R² = Na;   R* = 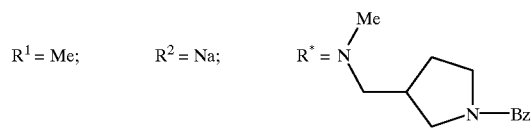

IR(KBr)cm⁻¹: 3407,1756,1694,1394

¹H-NMR(CD₃OD+D₂O) δ: 0.91–1.10(3H,m),1.21–1.32 (3H,m), 1.80–1.91(3H,m),3.20–3.42(8H,m),3.70(3H,br s),4.10–4.51(4H,m),7.45(5H,s)

Example I-119

R¹ = Me;   R² = H;   R* = 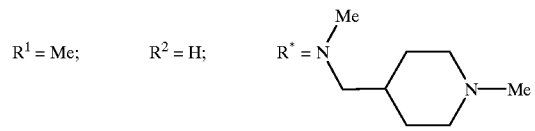

IR(KBr)cm⁻¹: 1760,1606,1388

¹H-NMR(D₂O) δ: 1.06(3H,d,J=6 Hz),1.24(3H,d,J=6 Hz), 1.57(2H, m),1.89(2H,m),2.25(1H,m),2.80(3H,m),2.92(2H, m),3.40–3.60(6H,m),4.23(1H,m),4.36(1H,dd,J=9.5,2.5 Hz)

Example I-120

R¹ = Me;   R² = H;   R* = 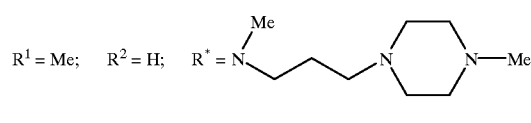

IR(KBr)cm⁻¹: 3405,1760,1604,1386

¹H-NMR(D₂O) δ: 1.08(3H,d,J=7.3 Hz),1.25(3H,d,J=6.4 Hz),1.97 (2H,br s),2.55–2.75(4H,m),{2.72(s),2.78(s)}(3H), 2.90–3.35(6H,m),3.42(3H,s),3.49–3.55(1H,m),3.52–3.72 (1H, m),3.76–4.22(2H,m),4.23(1H,quint,J=6.3 Hz),4.34 (1H,d, J=9.3 Hz)

Example I-121

R¹ = Me;  R² = H;  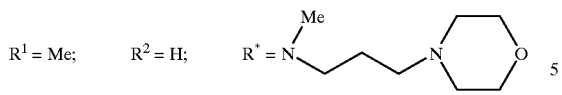

IR(KBr)cm⁻¹: 1754,1606,1390

¹H-NMR(D₂O) δ: 1.06(3H,d,J=7.1 Hz),1.24(3H,d,J=4.6 Hz),1.94–2.08(2H,m),2.60–2.95(6H,m),3.41(3H,s), 3.48–3.54(1H,m),3.60–4.14(7H,m),4.16–4.25(1H,m),4.33 (1H,br d,J=8.0 Hz)

Example I-122

R¹ = Me;  R² = H;  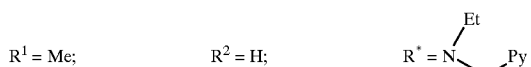

IR(KBr)cm⁻¹: 3403,1755,1603,1481,1389,1252

¹H-NMR(D₂O) δ: {0.97(d,J=7.2 Hz),1.20(d,J=7.2 Hz)} (3H),1.32 (3H,d,J=6.3 Hz),1.38(3H,t,J=7.0 Hz),3.55(1H,m), 3.72 (1H,m),3.82–4.20(2H,m),4.28(1H,m),4.38(1H,m), 5.20–5.50(2H,m),7.37–7.41(2H,m),8.50–8.60(2H,m)

Example I-123

R¹ = Me;  R² = Na;  

IR(KBr)cm⁻¹: 3425,1757,1605,1583,1389

¹H-NMR(D₂O) δ: 0.97–1.09(3H,m),1.20–1.30(3H,m), 3.35–3.55(6H,m),3.56–3.68(1H,m),4.10–4.40(4H,m), 7.36–7.44(2H,m),8.24–8.32(2H,M)

Example I-124

R¹ = Me;  R² = Na;  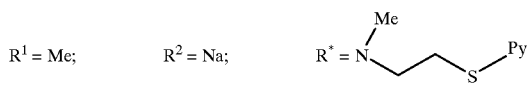

IR(KBr)cm⁻¹: 1747,1558,1394

¹H-NMR(D₂O) δ: 1.08(3H,d,J=7.0 Hz),1.27(3H,d,J=7.0 Hz),3.4–3.8(5H,m),4.18–4.42(2H,m),5.06–5.38(2H,m), 6.4–6.52(2H,m),7.48(1H,m)

Example I-125

R¹ = Me;  R² = Na;  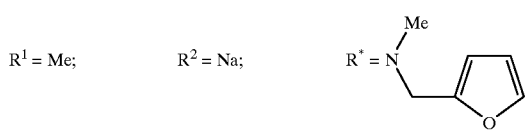

IR(KBr)cm⁻¹: 1747,1612,1392

¹H-NMR(D₂O) δ: 1.08(3H,d,J=7.3 Hz),1.27(3H,d,J=6.3 Hz),3.38–3.56(4H,m),3.72(1H,m),4.18–4.42(2H,m), 5.15–5.55(2H, m),7.02(1H,m),7.16(1H,m),7.41(1H,m)

Example I-126

R¹ = Me;  R² = Na;  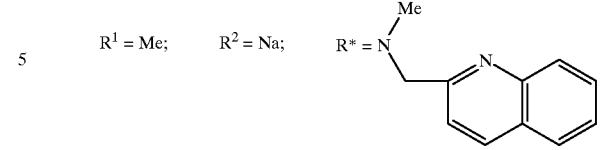

IR(KBr)cm⁻¹: 1745,1608,1386

¹H-NMR(DMSO-d₆) δ: 1.15(3H,d,J=6.3 Hz),1.28(3H,d, J=6.3 Hz),3.30–3.50(2H,m),3.60(3H,s),4.10–4.30(2H,m), 5.50(2H,m),7.40(1H,m),7.65(1H,m),7.75(1H,m),8.00(2H, m),8.35 (1H,m)

Example I-127

R¹ = Me;  R² = Na;  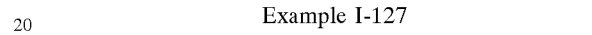

IR(KBr)cm⁻¹: 1767,1749,1699,1689,1650,1540,1390

¹H-NMR(D₂O) δ: 1.09(3H,d,J=7.3 Hz),1.24(3H,d,J=6.3 Hz),3.48–3.53(1H,m),3.57(3H,s),3.63–3.68(1H,m), 4.20–4.24(1H, m),4.32(1H,dd,J=10.1,2.4 Hz),5.31–5.48 (2H,m),8.50–8.59(3H,m)

Example I-128

R¹ = Me;  R² = Na;  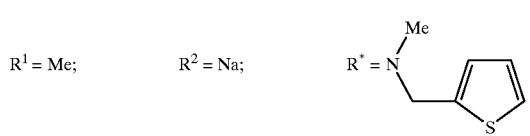

IR(KBr)cm⁻¹: 3380,1757,1608,1387,1261

¹H-NMR(D₂O) δ: 1.06(3H,br d,J=6 Hz),1.22(3H,d,J=6 Hz),3.3–3.8(2H,m),3.58(3H,s),4.25(2H,m),5.38(1H,m), 5.70(1H,d,J=16 Hz),7.48(2H,m),7.92(2H,m)

Example I-129

R¹ = Me;  R² = Na;  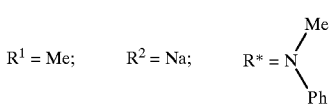

IR(KBr)cm⁻¹: 1749,1603,1363,1099

¹H-NMR(D₂O) δ: 1.01(3H,br),1.25(3H,d,J=6.4 Hz),3.46 (1H,br),3.61(1H,br),3.75(3H,s),4.22(2H,m),7.50(5H,m)

Example I-130

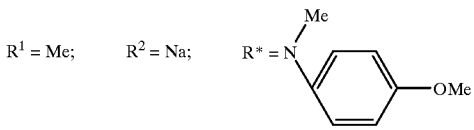

IR(KBr)cm$^{-1}$: 3415,2966,1753,1606,1508,1385,1250

$^1$H-NMR(D$_2$O) δ: 1.01(3H,d,J=6.9 Hz),1.27(3H,d,J=5.9 Hz),3.45–3.64(2H,m),3.72(3H,s),3.86(3H,s),4.21–4.30(2H,m), 7.07(2H,d,J=7.9 Hz),7.35(2H,d,J=8.2 Hz)

Example I-131

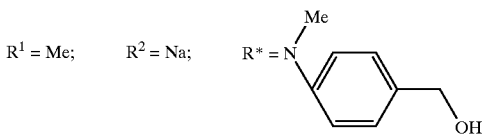

IR(KBr)cm$^{-1}$: 1745,1687,1514,1097

$^1$H-NMR(D$_2$O) δ: 0.97(3H,br d),1.23(3H,d,J=5.2 Hz), 3.42(1H, br s),3.56(1H,br s),3.71(3H,s),4.20(2H,m),4.64(2H,s),7.38(2H,m),7.46(2H,m)

Example I-132

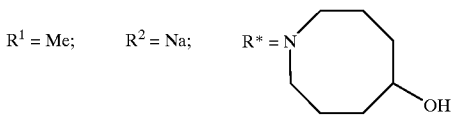

IR(KBr)cm$^{-1}$: 3334,1749,1598,1560,1392

$^1$H-NMR(D$_2$O) δ: 1.19(3H,d,J=7.5 Hz),1.36(3H,d,J=6.5 Hz),1.60–1.81(2H,m),1.81–2.24(6H,m),3.61(1H,dd,J=2.5, 5.6 Hz), 3.72–4.02(3H,m),4.02–4.40(4H,m),4.45(1H,dd,J=2.5,9.3 Hz)

Example II-1

(1R,5S,6S)-6-[(R)-1-hydroxyethyl]-2-[(4,4-dimethyl-1-piperazinio)thiocarbonylthio]-1-methyl-1-carbapen-2-em-3-carboxylate

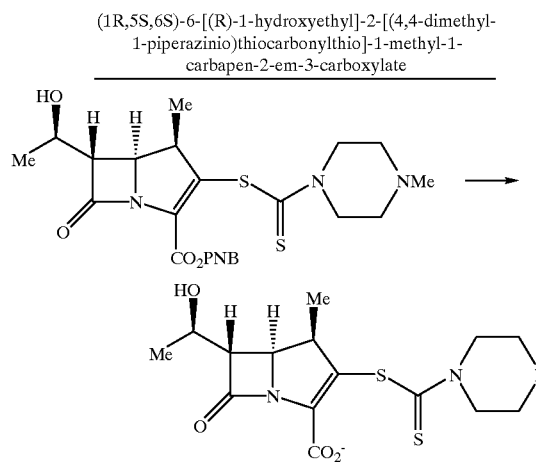

Methyl iodide (0.3 ml, 4.82 mmol) was added to a solution of the compound obtained in Step 1 of Example I-31 (500 mg, 0.96 mmol) in acetone (10 ml) and tetrahydrofuran (10 ml) under ice cooling, and the mixture was stirred at that temperature for 2 hours and then at room temperature for 2 hours. The solvents were distilled off under reduced pressure, the residue was dissolved in a mixed solvent of tetrahydrofuran (25 ml) and ethanol (5 ml), an aqueous solution (25 ml) of sodium hydrogencarbonate (80 mg, 0.95 mmol) and 10% palladium-carbon catalyst (500 mg) were added, and the reaction mixture was vigorously stirred overnight in a hydrogen stream. The catalyst was removed from the reaction mixture, and the filtrate was concentrated under reduced pressure. The insoluble matter was filtered out, the filtrate was subjected to reverse phase column chromatography (YMC™ GEL ODS-AQ-120-S50, 14 ml; aqueous 10% methanol solution), and the fractions containing the desired compound were concentrated and freeze-dried to give the captioned compound (48 mg, yield: 13%).

IR(KBr)cm$^{-1}$: 1749,1603,1387

$^1$H-NMR(D$_2$O) δ: 1.09(3H,d,J=7.3 Hz),1.27(3H,d,J=6.8 Hz),3.28 (6H,s),3.5–3.7(7H,m),4.25(1H,m),4.38(1H,dd,J=10,3 Hz), 4.50(3H,br s)

Compounds from Example II-2 to Example II-15 were produced by the same reaction as above.

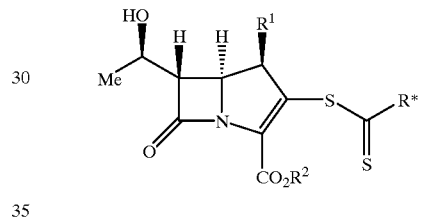

Example II-2

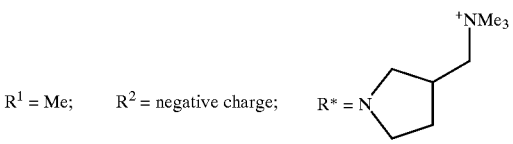

IR(KBr)cm$^{-1}$: 3423,1753,1604,1436,1384

$^1$H-NMR(D$_2$O) δ: 1.13(3H,d,J=7.0 HZ),1.30(3H,d,J=6.5 Hz),1.90–2.05(1H,m),2.32–2.51(1H,m),2.90–3.10(1H,m), 3.20(9H,s),3.52–3.62(4H,m),3.70–3.79(3H,m),4.10–4.21(1H,m),4.21–4.30(1H,m),4.33–4.44(1H,m)

Example II-3

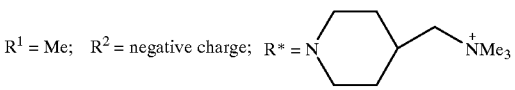

IR(KBr)cm$^{-1}$: 1757,1604,1483,1377

$^1$H-NMR(D$_2$O) δ: 1.07(3H,d,J=7 Hz),1.24(3H,d,J=6.5 Hz),1.53 (2H,m),2.00(2H,m),2.37(1H,m),3.13(9H,s),3.26 (3H,m),3.48(2H,m),3.50(1H,m),4.22(1H,m),4.32(1H,dd,J=10, 3 Hz),4.64(1H,m),5.22(1H,m)

Example II-4

R¹ = Me; R² = negative charge; R* = 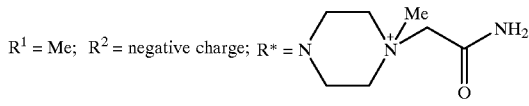

IR(KBr)cm⁻¹: 1751,1699,1419

¹H-NMR(D₂O) δ: 1.08(3H,d,J=7.3 Hz),1.27(3H,d,J=5.5 Hz),3.1–3.4(1H,m),3.43(3H,s),3.52–3.7(2H,m),3.78–4.08 (5H,m), 4.16–4.5(6H,m)

Example II-5

R¹ = Me;    R² = negative charge;

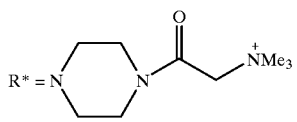

IR(KBr)cm⁻¹: 1758,1658,1604,1415,1380,1220

¹H-NMR(D₂O) δ: 1.08(3H,d,J=7.3 Hz),1.25(3H,d,J=6.3 Hz),3.31 (9H,s),3.51(1H,dd,J=5.9,3.1 Hz),3.61–3.70(3H, m),3.72–3.80(2H,m),4.07–4.30(5H,m),4.35(1H,dd,J=9.5, 2.6 Hz), 4.43(2H,s)

Example II-6

R¹ = Me;    R² = negative charge;    R* = 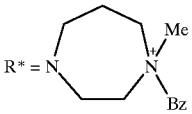

IR(KBr)cm⁻¹: 1761,1749,1603,1387

¹H-NMR(D₂O) δ: 1.10(3H,d,J=7.3 Hz),1.27(3H,d,J=6.4 Hz),2.39 (2H,br s),3.19(3H,s),3.21(3H,s),3.5–3.9(6H,m), 3.9–4.7(6H,m)

Example II-7

R¹ = Me;    R² = negative charge;

R* = 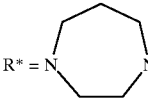

IR(KBr)cm⁻¹: 1749,1699,1558

¹H-NMR(D₂O) δ: 1.08(3H,d,J=7.3 Hz),1.25(3H,d,J=6.3 Hz), 2.28–2.52(2H,m),3.3–3.41(3H,m),3.5–4.29(11H,m), 4.3–4.38(3H,m)

Example II-8

R¹ = Me;    R² = negative charge;    R* = 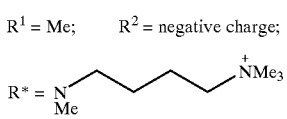

IR(KBr)cm⁻¹: 1766,1751,1456

¹H-NMR(D₂O) δ: 1.08(3H,d,J=7.3 Hz),1.26(3H,d,J=6.5 Hz),3.15 (3H,s),3.46–3.8(6H,m),4.08–4.42(4H,m), 7.45–7.62 (5H,m)

Example II-9

R¹ = Me;    R² = negative charge;    R* = 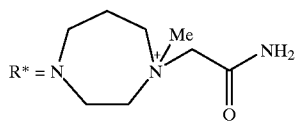

IR(KBr)cm⁻¹: 1770,1749,1519,1456

¹H-NMR(D₂O) δ: 0.95–1.15(3H,m),1.2–1.32(3H,m), 2.28–2.51(2H,m),3.0–3.16(3H,m),3.28–4.45(12H,m), 4.52–4.65(2H,m),7.52(5H,s)

Example II-10

R¹ = Me;    R² = negative charge;

R* = 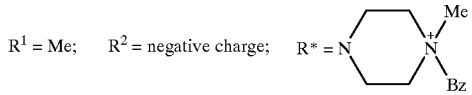

IR(KBr)cm⁻¹: 3421,1749,1605,1387

¹H-NMR(D₂O) δ: 1.15(3H,d,J=7.3 Hz),1.32(3H,d,J=6.3 Hz),1.74–2.00(4H,m),3.09–3.22(9H,m),3.30–3.62(6H,m), 3.68–4.4(4H,m),4.42(1H,dd,J=9.8,2.8 Hz)

Example II-11

R¹ = Me;    R² = negative charge;    R* =

IR(KBr)cm⁻¹: 1757,1604,1468,1377

¹H-NMR(D₂O) δ: 1.19(3H,d,J=7.5 Hz),1.26(3H,d,J=6.5 Hz),2.06 (2H,m),2.30(2H,m),3.18(6H,s),3.39(3H,br s),3.45–3.75 (6H,m),4.25(1H,m),4.36(1H,dd,J=9.5,3 Hz)

Example II-12

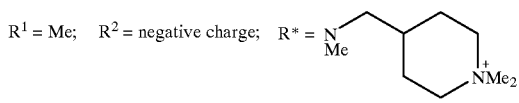

R¹ = Me;  R² = negative charge;  R* = [structure]

IR(KBr)cm⁻¹: 1749,1602,1386

¹H-NMR(D₂O) δ: 1.07(3H,d,J=7 Hz),1.25(3H,d,J=6.5 Hz),1.84 (4H,m),2.30(1H,m),3.00–3.15(6H,m),3.20–3.35 (2H,m), 3.40–3.55(5H,m),4.24(1H,m),4.34(1H,dd,J=9,3 Hz)

Example II-13

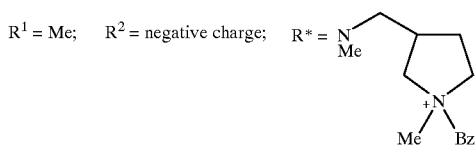

R¹ = Me;  R² = negative charge;  R* = [structure]

IR(KBr)cm⁻¹: 1753,1606,1390

¹H-NMR(D₂O) δ: 1.02(3H,br s),1.25(3H,br s),1.96–2.13 (2H,m ),2.31–2.40(1H,m),2.96(3H,s),3.08–3.22(2H,m),3.39 (3H,m),3.40–3.78(5H,m),3.98–4.08(1H,m),4.20–4.28 (1H, m),4.30–4.40(1H,m),4.42–4.58(2H,m),7.50(5H,s)

Example II-14

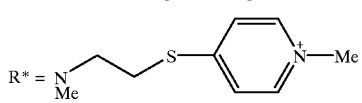

R¹ = Me;  R² = negative charge;
R* = [structure]

IR(KBr)cm⁻¹: 3425,1757,1635,1603,1497,1387,1113

¹H-NMR(D₂O) δ: {1.05(d,J=7.3 Hz),1.07(d,J=7.3 Hz)} (3H), {1.20(d,J=6.0 Hz),1.26(d,J=6.0 Hz)}(3H),{3.40(s),3.44(s)}(3H),3.48–3.79(4H,m),4.17(3H,s),4.12–4.53 (4H,m), 7.78–7.90(2H,m),8.33–8.42(2H,m)

Example II-15

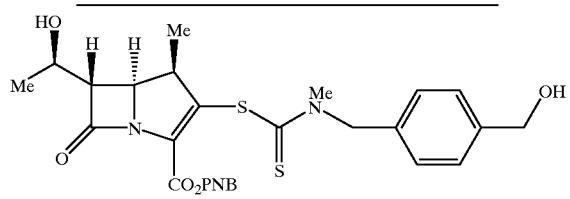

R¹ = Me;  R² = negative charge;  R* = [structure]

IR(KBr)cm⁻¹: 3419,1751,1641,1612,1470,1379,1267

¹H-NMR(D₂O) δ: 1.12–1.50(9H,m),4.00–4.50(9H,m), 5.31–5.76(2H,m),7.80–8.15(2H,m),8.65–8.98(2H,m)

Example III-1

(1R,5S,6S)-2-[[N-[4-(4-carbamoylmethyl-1,4-diazabicyclo[2.2.2]octanedium-1-ylmethyl)benzyl]-N-methylamino]thiocarbonylthio]-6-[(R)-1-hydroxyethyl]-1-methyl-1-carbapen-2-em-3-carboxylic acid monochloride salt

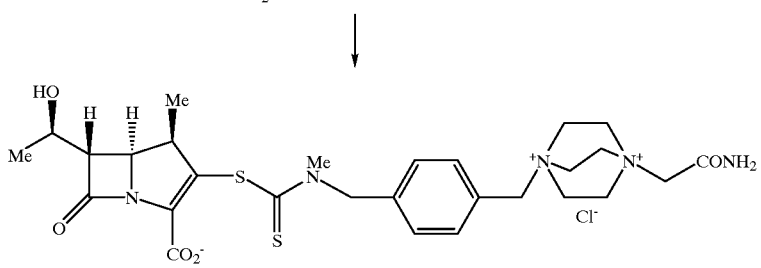

N,N-diisopropylamine (2.34 ml, 13.4 mmol) and 1-propanesulfonyl chloride (1.47 ml, 13.1 mmol) were added successively, in a nitrogen stream, to a tetrahydrofuran solution (40 ml) of the compound obtained in Step 1 of Example 95 (2.50 g, 4.37 mmol) under ice cooling, and the reaction solution was stirred at that temperature for one hour. The reaction solution was poured in a mixed solution of diluted hydrochloric acid and ethyl acetate, and the organic layer was washed with saturated saline, dried over anhydrous sodium sulfate and concentrated under reduced pressure. Sodium iodide (2.62 g, 17.5 mmol) was added to an acetone solution (40 ml) of the obtained residue under ice cooling. The reaction solution was stirred at that temperature for one hour. The reaction solution was poured in a mixed solution of aqueous 10% sodium thiosulfate solution and ethyl acetate (1:1; 100 ml), and the organic layer was washed with saturated saline, dried over anhydrous sodium sulfate and concentrated under reduced pressure. A 4-carbamoylmethyl-1,4-diazabicyclo[2.2.0]octane-trifluoromethanesulfonate salt (2.09 g, 6.55 mmol) was added to an acetonitrile solution (57 ml) of the obtained residue at room temperature. The reaction solution was stirred at that temperature for 12 hours, and concentrated under reduced pressure. 0.5 N sodium 3-morpholinopropanesulfonate buffer (113 ml, pH 7.0) and 10% palladium-carbon catalyst (4.24 g) were added to a tetrahydrofuran solution (113 ml) of the obtained residue, and the reaction solution was vigorously stirred, in a hydrogen stream, at room temperature for 5 hours. The catalyst was removed from the reaction mixture by filtration, and the filtrate was concentrated under reduced pressure to give an aqueous solution. The insoluble matter was removed by filtration, the filtrate was subjected to reverse phase column chromatography (YMC•GEL™ ODS-AQ-120-S50, 50 ml, saturated saline→methanol-water 3:7), and the fractions containing the desired substance were concentrated and freeze-dried to give the captioned compound (603.0 mg, yield: 22.1%).

IR(KBr)cm$^{-1}$: 3731,2970,1757,1693,1385,1209,1113

$^1$H-NMR(D$_2$O) δ: 0.98–1.10(3H,m),1.23(3H,d,J=6.5 Hz), 3.45–3.71(5H,m),3.99–4.36(18H,m),5.13–5.30(2H,m), 7.42–7.57 (4H,m)

Compounds from Example III-2 to Example III-23 were produced by the same reaction as above.

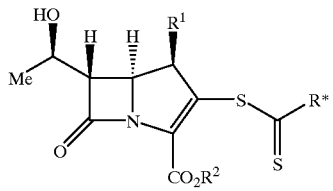

Example III-2

R$^1$ = Me; R$^2$ = negative charge;

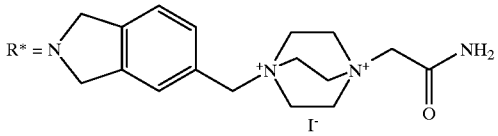

IR(KBr)cm$^{-1}$: 3419,1751,1695,1423,1028

$^1$H-NMR(D$_2$O) δ: {1.10(d,J=7.3 Hz),1.11(d,J=7.3 Hz)}(3H),1.31 (3H,d,J=6.4 Hz),3.59(1H,m),3.79(2H,m),4.05 (6H,m),4.27 (6H,m),4.40(3H,m),4.80–5.12(4H,m), 7.54–7.57(3H,m)

Example III-3

R$^1$ = Me; R$^2$ = negative charge;

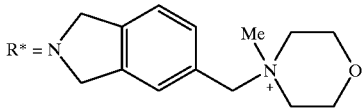

IR(KBr)cm$^{-1}$: 3425,1751,1645,1425

$^1$H-NMR(D$_2$O) δ: 1.13(3H,d,J=6.9 Hz),1.31(3H,d,J=6.5 Hz),3.15 (3H,s),3.44(2H,m),3.55–3.72(3H,m),4.11(4H,m), 4.29(1H,m),4.40(1H,m),4.67(3H,m),4.85–5.19(5H,m),7.54 (3H,m)

Example III-4

R$^1$ = Me; R$^2$ = negative charge;

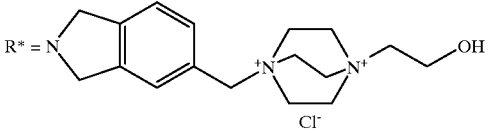

IR(KBr)cm$^{-1}$: 3415,1760,1599,1423,1386,1105

$^1$H-NMR(D$_2$O) δ: {1.08(d,J=7.3 Hz),1.09(d,J=7.3 Hz)}(3H),1.30 (3H,d,J=6.0 Hz),3.50(1H,m),3.77(3H,m), 3.93–4.20(12H,m)4.26(1H,m),4.37(1H,m),4.80–5.10(2H, m) 7.49–7.62 (3H,m)

Example III-5

R$^1$ = Me; R$^2$ = negative charge;

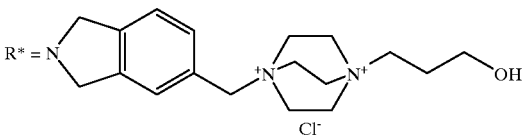

IR(KBr)cm$^{-1}$: 3421,1753,1604,1423,1388,1107

$^1$H-NMR(D$_2$O) δ: {1.10(d,J=7.3 Hz),1.11(d,J=7.3 Hz)}(3H),1.31 (3H,d,J=6.2 Hz),2.07(2H,m),3.58(1H,m),3.70 (4H,m),3.79 (1H,m),4.03(12H,br s),4.28(1H,m),4.38(1H, m),4.80–5.12 (4H,m),7.54–7.58(3H,m)

Example III-6

R$^1$ = Me; R$^2$ = negative charge;

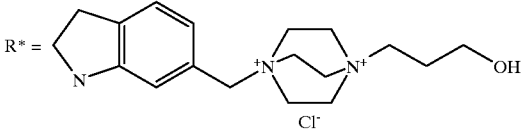

IR(KBr)cm$^{-1}$: 1758,1604,1392,1268

$^1$H-NMR(D$_2$O) δ: 1.09(3H,d,J=7.0 Hz),1.22(3H,d,J=6.5 Hz),2.01 (2H,m),3.05–3.30(2H,m),3.50–3.70(6H,m),3.95 (12H,br s),4.21(2H,m),4.54(1H,m),7.33(1H,d,J=8.0 Hz), 7.50(1H,d,J=8.0 Hz)

Example III-7

R$^1$ = Me; R$^2$ = negative charge; R* =

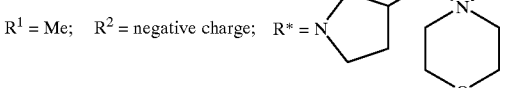

IR(KBr)cm$^{-1}$: 1754,1604,1438,1380

$^1$H-NMR(D$_2$O) δ: 1.13(3H,d,J=7.2 Hz),1.28(3H,d,J=4.2 Hz),1.86–2.10(1H,m),2.32–2.51(1H,m),2.95–3.15(1H,m), {3.27 (s),3.29(s)}(3H),3.50–3.81(11H,m),4.02–4.15(5H,m), 4.25–4.30(1H,m),4.34–4.45(1H,m)

Example III-8

R¹ = Me; R² = negative charge;

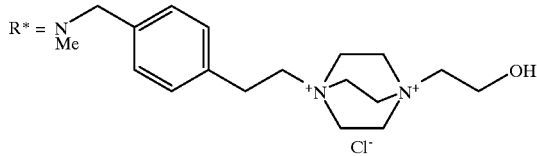

IR(KBr)cm⁻¹: 3396,1753,1606,1387,1093
¹H-NMR(D₂O) δ: {1.02(d,J=7.2 Hz),1.11(d,J=7.2 Hz)}(3H),1.29 (3H,d,J=6.5 Hz),3.19–3.30(2H,m),{3.44(s),3.49(s)}(3H), 3.40–3.56(1H,m),3.66–3.90(5H,m),4.05–4.38(16H,m), {5.12(s),5.20–5.35(m)}(2H),7.29–7.45(4H,m)

Example III-9

R¹ = Me; R² = negative charge;

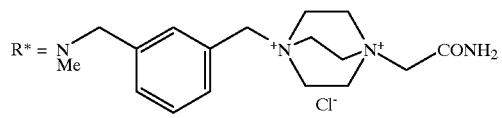

IR(KBr)cm⁻¹: 3425,1749,1697,1388,1278
¹H-NMR(D₂O) δ: 1.01–1.12(3H,m),1.24(3H,d,J=6.3 Hz), 3.48–3.73(5H,m),3.99–4.37(18H,m),4.95–5.61(2H,m), 7.32–7.61(4H,m)

Example III-10

R¹ = Me; R² = negative charge;

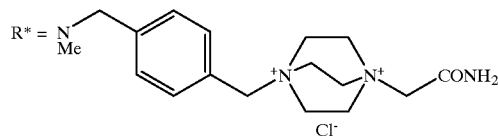

IR(KBr)cm⁻¹: 3731,2970,1757,1693,1385,1209,1113
¹H-NMR(D₂O) δ: 0.98–1.10(3H,m),1.22–1.24(3H,d,J=6.5 Hz), 3.45–3.71(5H,m),3.99–4.36(18H,m),5.13–5.30(2H,m), 7.42–7.57(4H,m)

Example III-11

R¹ = Me; R² = negative charge;

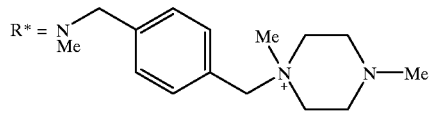

IR(KBr)cm⁻¹: 3398,1756,1604,1387
¹H-NMR(D₂O) δ: {0.95(d,J=7.2 Hz),1.08(d,J=7.2 Hz)}(3H),1.23 (3H,d,J=6.3 Hz),2.34(3H,s),2.70–2.83(2H,m), 2.89–3.00 (2H,m),2.98(3H,s),3.20–3.54(5H,m),{3.42(s), 3.46(s)}(3H),3.63–3.75(1H,m),4.16–4.24(1H,m),4.24–4.32 (1H,m),4.51–4.58(2H,m),5.10–5.35(2H,m),7.32–7.40(2H, m),7.48–7.56(2H,m)

Example III-12

R¹ = Me; R² = negative charge;

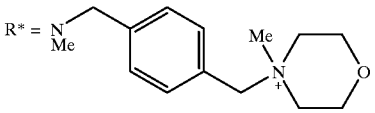

IR(KBr)cm⁻¹: 1749,1604,1386

¹H-NMR(D₂O) δ: {0.93(d,J=6.6 Hz),1.06(d,J=6.6 Hz)}(3H),1.22 (3H,d,J=5.8 Hz),3.06(3H,s),3.27–3.72(9H,m), 3.98–4.08 (4H,m),4.12–4.29(2H,m),4.59(2H,s),{5.14(s), 5.27(s)}(2H),7.31–7.39(2H,m),7.43–7.56(2H,m)

Example III-13

R¹ = Me; R² = negative charge;

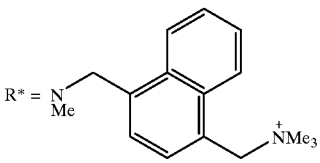

IR(nujor)cm⁻¹: 1758,1600

¹H-NMR(D₂O) δ: 0.87(1H,d,J=7.0 Hz),1.07(2H,d,J=7.2 Hz),1.22 (3H,d,J=6.4 Hz),3.06(6H,s),3.08(3H,s),3.47(2H,s), 3.49 (1H,s),3.68(2H,m),4.21(2H,m),4.91(2H,m),5.59(2H, m),7.24(1H,m),7.63(3H,m),7.91(1H,m),8.20(1H,m)

Example III-14

R¹ = Me; R² = negative charge;

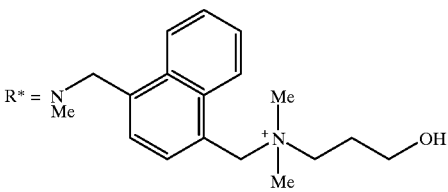

IR(nujor)cm⁻¹: 1756,1600

¹H-NMR(D₂O) δ: 1.04(3H,m),1.21(3H,d,J=6.4 Hz),2.06 (2H,m), 2.53(1H,m),2.66(1H,s),2.78(2H,s),2.97(6H,s),3.17 (1H, m),3.44(2H,m),3.65(2H,m),4.18(2H,m),4.92(2H,m), 5.60 (2H,m),7.23(2H,m),7.67(2H,m),7.94(1H,m),8.23(1H, m)

Example III-15

R¹ = Me; R² = negative charge;

IR(nujor)cm⁻¹: 1760,1604

¹H-NMR(D₂O) δ: 0.81(1H,d,J=7.0 Hz),1.00(2H,d,J=7.2 Hz),1.17 (3H,d,J=6.3 Hz),2.26(6H,s),2.91(3H,m),2.97(6H, s),3.32 (2H,s),3.39(1H,s),3.40(1H,m),3.52(1H,m),3.64(1H, m), 4.13(1H,m),4.89(2H,m),5.46(2H,m),7.22(2H,m),7.58 (3H,m),8.18(1H,m)

Example III-16

R¹ = Me; R² = negative charge;

IR(nujor)cm⁻¹: 1756,1695,1600

¹H-NMR(DMSO-d₆+D₂O) δ: 1.04(6H,m),3.51(20H,m), 4.98(4H,m), 7.58(6H,m)

Example III-17

R¹ = Me; R² = negative charge;

IR(nujor)cm⁻¹: 1754,1697,1598

¹H-NMR(DMSO-d₆+D₂O) δ: 0.92(3H,m),1.11(3H,m), 3.03–4.22 (18H,m),4.98–6.02(4H,m),7.03–8.41(4H,m)

Example III-18

R¹ = Me; R² = negative charge;

IR(nujor)cm⁻¹: 1754,1600

¹H-NMR(D₂O) δ: {0.72(d,J=7.6 Hz),0.82(d,J=7.1 Hz)} (2H),{0.94 (d,J=6.0 Hz),1.08(d,J=6.3 Hz)}(2H),3.22(1H, m),{3.26(s), 3.28(s)}(2H),3.46(1H,m),3.69(3H,m),3.78(1H, m),4.05(14H,m),4.78(2H,m),5.13(1H,m),5.46(1H,m),7.37 (1H,m),7.50 (1H,m),7.62(1H,m),7.91(3H,m)

Example III-19

R¹ = Me; R² = negative charge;

IR(nujor)cm⁻¹: 1754,1600

¹H-NMR(DMSO-d₆) δ: 0.90(3H,m),1.11(3H,m),1.57 (1H,m),1.81 (5H,m),2.00(1H,m),2.90(1H,m),3.09(1H,m), 3.42(6H,m), 3.90(1H,m),4.06(1H,m),4.50(2H,s),5.43(2H, m),7.52(2H,m),7.69(1H,m),7.99(3H,m)

Example III-20

R¹ = Me; R² = negative charge;

IR(nujor)cm⁻¹: 1760,1602

¹H-NMR(DMSO-d₆) δ: 0.82(3H,m),1.12(3H,m),3.23 (1H,s),3.52 (6H,m),3.74(2H,m),4.08(8H,m),4.80(2H,m), 7.31(1H,m),7.50(2H,m),7.82(3H,m)

Example III-21

R¹ = Me; R² = negative charge;

IR(nujor)cm⁻¹: 1758,1602

¹H-NMR(DMSO-d₆) δ: 0.89(3H,m),1.12(3H,d,J=6.4 Hz),3.11 (1H,M),3.40(3H,m),3.70(1H,m),3.89(1H,m),4.06 (1H,m), 4.18(2H,s),4.48(6H,m),5.34(8H,m),7.51(2H,m), 7.80(1H,m),7.99(3H,m)

Example III-22

R¹ = Me; R² = negative charge;

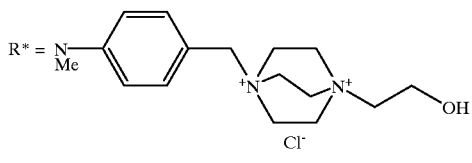

IR(KBr)cm⁻¹: 3450,1759,1371,1097

¹H-NMR(D₂O) δ: 1.05(3H,d,J=7.3 Hz),1.21(3H,d,J=6.3 Hz),3.45 (2H,m),3.73(2H,m),3.79(3H,s),4.09(16H,m),4.82 (2H,s), 7.65(3H,br s)

Example III-23

R¹ = Me; R² = negative charge;

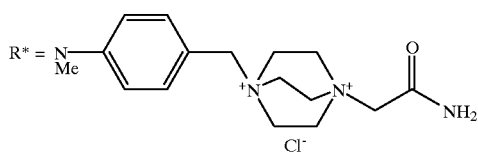

IR(KBr)cm⁻¹: 3452,1759,1695,1623,1458,1354,1275, 1078

¹H-NMR(D₂O) δ: 1.05(3H,d,J=7.0 Hz),1.20(3H,d,J=6.5 Hz),3.45 (2H,m),3.78(3H,s),4.07(7H,m),4.26(7H,m),4.39 (2H,s),4.82(2H,s),7.64(4H,s)

Example IV-1

Sodium (1R,5S,6S)-6-[(R)-1-hydroxyethyl]-2-(methylallylaminothiocarbonylthio)-1-methyl-1-carbapen-2-em-3-carboxylate

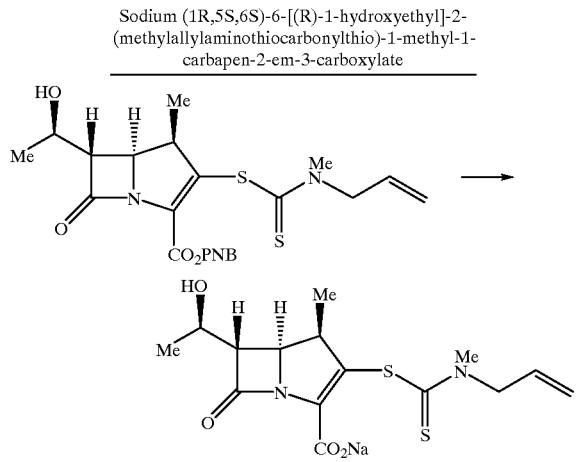

p-Nitrobenzyl (1R,5S,6S)-6-[(R)-1-hydroxyethyl]-2-(methylallylaminothiocarbonylthio)-1-methyl-1- carbapen-2-em-3-carboxylate (400 mg, 0.814 mmol) obtained in the same manner as in Step 1 of Example I-1 was dissolved in an mixed solution of tetrahydrofuran (7 ml) and a phosphate buffer (pH 6.0, 0.35 M, 15 ml), zinc powder (1.2 g) was added to this mixed solution, and the mixture was stirred at room temperature for 2 hours. The insoluble matter was removed by filtration, the filtrate was concentrated under reduced pressure up to such an extent that dryness did not occur, the deposited insoluble matter was removed by filtration, the filtrate was subjected to reverse phase column chromatography (YMC™•GEL ODS-AQ-120-S50, 14 ml, aqueous 3% acetonitrile solution), and the fractions containing the desired substance were concentrated and freeze-dried to give the captioned compound (132 mg, yield: 41.5%).

IR(KBr)cm⁻¹: 3431,1759,1606,1367

¹H-NMR(D₂O) δ: {1.13(d,J=6.9 Hz),1.15(d,J=6.9 Hz)} (3H),1.32 (3H,d,J=6.3 Hz),{3.48(s),3.50(s)}(3H),3.52–3.60 (1H,m),3.69–3.83(1H,m),4.24–4.35(1H,m),4.36–4.44(1H, m), {4.52–4.65(m),4.72–4.78(m)}(2H),5.17–5.40(2H,m), 5.80–6.01(1H,m)

¹H-NMR data of p-nitrobenzyl (1R,5S,6S)-6-[(R)-1-hydroxyethyl]-2-(methylallylaminothiocarbonylthio)-1-methyl-1-carbapen-2-em-3-carboxylate ¹H-NMR(CDCl₃) δ: 1.10–1.20(3H,m),1.37(3H,d,J=6.3 Hz),3.30–3.50(4H,m),3.95–4.10(1H,m),4.23–4.51(2H,m), 4.60–4.69(1H,m),5.18–5.34(3H,m),5.49(1H,d,J=13.5 Hz), 5.74–5.90(1H,m),7.64(2H,d,J=8.6 Hz),8.18–8.26(4H,m)

Compounds from Example IV-2 to Example IV-7 were produced by the same reaction as above.

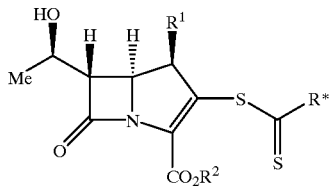

Example IV-2

R¹ = Me; R² = Na; R* = 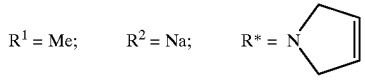

IR(KBr)cm⁻¹: 1757,1610,1327,1390

¹H-NMR(D₂O) δ: 1.12(3H,d,J=7.5 Hz),1.28(3H,d,J=6 Hz),3.55 (1H,dd,J=6,3 Hz),3.80(1H,m),4.27(1H,m),4.38 (1H,dd,J=10,3 Hz),4.55(4H,m),5.98(2H,m)

Example IV-3

R¹ = Me; R² = K; R* = 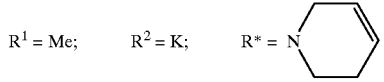

IR(KBr)cm⁻¹: 3396,1753,1386,1427

¹H-NMR(D₂O) δ: 1.18(3H,d,J=6.9 Hz),1.35–1.37(3H,m), 2.35–2.50(2H,m),3.59–3.62(1H,m),3.77(1H,dq,J=7.3,6.8 Hz), {4.18–4.24(m),4.60–4.72(m)}(3H),4.28–4.37(1H,m), 5.74–5.90(1H,m),6.03–6.13(1H,m)

Example IV-4

R¹ = Me; R² = Na; R* = 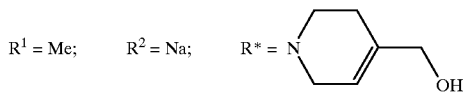

IR(KBr)cm⁻¹: 1754,1604,1388

¹H-NMR(D₂O) δ: 1.15–1.21(3H,m),1.35(3H,d,J=6.4 Hz), 2.32–2.46(2H,m),3.61(1H,dd,J=5.9,3.0 Hz),3.76(1H,dq,J=

9.8,7.6 Hz),4.10–4.23(4H,m),4.33(1H,quint,J=6.1 Hz),4.43 (1H,dd,J=9.6,2.9 Hz),4.66–4.72(2H,m),5.72–5.82(1H,m)

Example IV-5

$R^1$ = Me; $R^2$ = H; R* = 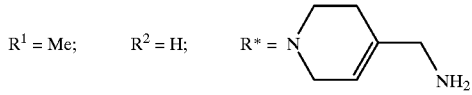

IR(KBr)cm$^{-1}$: 1758,1583,1421,1382

$^1$H-NMR(DMSO-d$_6$) δ: 0.95(3H,d,J=6.8 Hz),1.13(3H,d, J=6.3 Hz), 2.10–2.40(2H,m),3.10–3.67(4H,m),3.78–4.70 (6H,m),5.80 (1H,br s),8.30(1H,br S)

Example IV-6

$R^1$ = Me; $R^2$ = negative charge; R* = 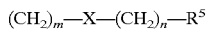

IR(KBr)cm$^{-1}$: 1756,1604,1419,1384,1268

$^1$H-NMR(D$_2$O) δ: 1.17(3H,d,J=7.2 Hz),1.34(3H,d,J=6.3 Hz),2.52–2.82(2H,m),3.17(9H,s),3.61(1H,dd,J=5.9,3.0 Hz), 3.71–3.83(1H,m),4.04(2H,s),4.10–4.48(4H,m),4.61–4.99 (2H,m),6.21–6.32(1H,m)

Example IV-7

$R^1$ = Me; $R^2$ = negative charge;

R* = 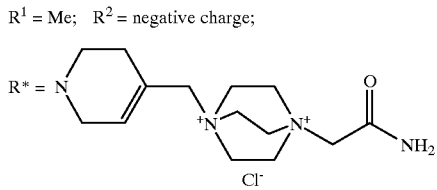

IR(KBr)cm$^{-1}$: 1749,1695,1608,1388

$^1$H-NMR(D$_2$O) δ: 1.11(3H,d,J=7.2 Hz),1.28(3H,d,J=6.3 Hz),2.50–2.62(2H,m),3.56(1H,dd,J=5.6,2.9 Hz),3.70(1H, quint,J=7.6 Hz),4.02–4.13(6H,m),4.20–4.33(12H,m),4.38 (1H, dd,J=7.7,2.7 Hz),4.45(2H,s),4.63–4.73(1H,m), 6.38–6.47 (1H,m)

Industrial Aplicability

The compounds of the invention are novel compounds not disclosed in literatures, and since they have wide antibacterial spectra and strong antibacterial activities against Gram-positive bacteria and Gram-negative bacteria and excellent stability against β-lactamase, they are expected to contribute greatly to treatment of refractory infectious diseases.

What is claimed is:
1. A compound represented by the formula

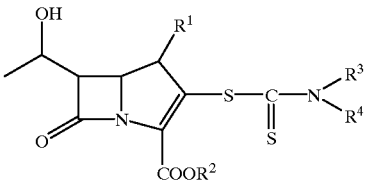

wherein
$R^1$ represents a hydrogen atom or a lower alkyl group,
$R^2$ represents a hydrogen atom, an ester residue, an alkali metal or negative charge, and
$R^3$ and $R^4$ are the same or different, and each represent a hydrogen atom or a group represented by the formula:

$(CH_2)_m$—X—$(CH_2)_n$—$R^5$ wherein
$R^5$ represents a hydrogen atom, a lower alkyl group, a cyclo-lower alkyl group, a lower alkenyl group, a lower alkynyl group, an aryl group, an aromatic heterocyclic group selected from a thiazolyl group, an isothiazolyl group, an oxazolyl group, an isoxazolyl group, a pyrazolyl group, an imidazolyl group, a triazolyl group, a pyridyl group, a pyrimidinyl group, a pyrazinyl group, a quinolinyl group, an isoquinolinyl group, a benzothiazolyl group, a benzoxazolyl group, a benzopyrazolyl group, a quinoxalinyl group, a benzimidazolyl group, a benzotriazolyl group, a thiadiazolyl group, a thienyl group, a furyl group, and a tetrazolyl group, a non-aromatic heterocyclic group selected from

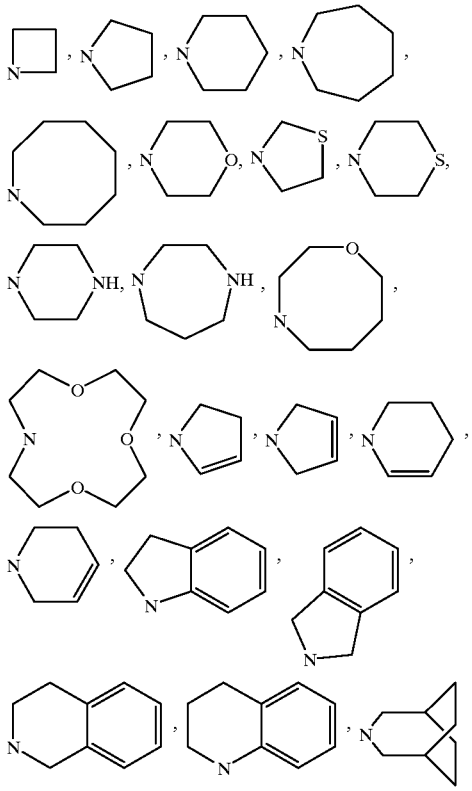

-continued

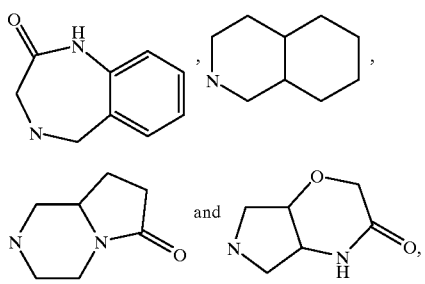

or a polycyclic group selected from

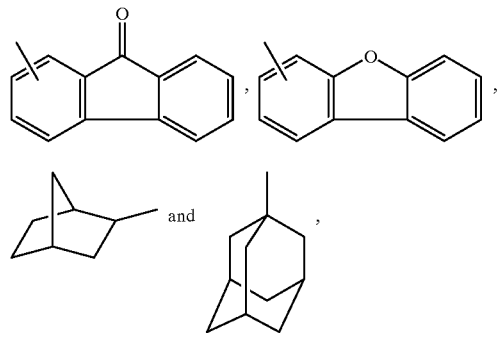

each of the lower alkyl group, the cyclo-lower alkyl group, the lower alkenyl group, the lower alkynyl group, the aryl group, the aromatic heterocyclic group, the non-aromatic heterocyclic group and the polycyclic group optionally having substituent(s) selected from a hydroxyl group, a cyano group, hydroxy-lower alkyl groups, a carboxyl group, lower alkoxycarbonyl groups, a carbamoyl group, N-lower alkylcarbamoyl groups, N,N-dilower alkylcarbamoyl groups, a carbamoyloxy group, N-lower alkylcarbamoyloxy groups, N,N-dilower alkylcarbamoyloxy groups, an amino group, N-lower alkylamino groups, N,N-dilower alkylamino groups, N,N,N-trilower alkylammmonio groups, amino-lower alkyl groups, N-lower alkylamino-lower alkyl groups, N,N-dilower alkylamino-lower alkyl groups, N,N,N-trilower alkylammmonio-lower alkyl groups, lower alkanoylamino groups, aroylamino groups, lower alkanoylamidino-lower alkyl groups, lower alkylsulfonylamino groups, N,N-dilower alkyl-N-hydroxy-lower alkylammonio-lower alkyl groups, N,N-dilower alkyl-N-dilower alkylamino-lower alkylammonio-lower alkyl groups, a hydroxyimino group, lower alkoxyimino groups, groups:

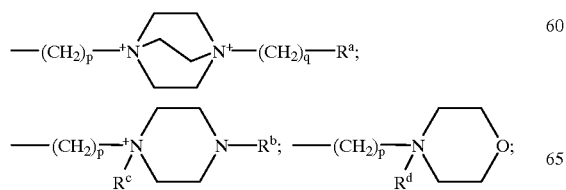

-continued

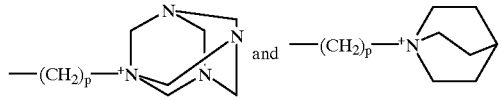

wherein $R^a$ represents a hydroxyl group or a carbamoyl group, $R^b$ represents a lower alkyl group, a formyl group or a lower alkanoyl group, $R^c$ and $R^d$ are the same or different and each represent a lower alkyl group, and p and q are the same or different and each represent 0 to 4, halogen atoms, a trifluoromethyl group, an azido group, a nitro group, $SR^6$, $COR^6$, $N(R^6)CHO$, $COOR^6$, $SO_2N(R^6)R^7$, $CSN(R^6)R^7$, $SC(S)N(R^6)R^7$, wherein the definition of $R^6$ and $R^7$ are the same as that in the later-described definition of X, cyclo-lower alkyl groups, groups:

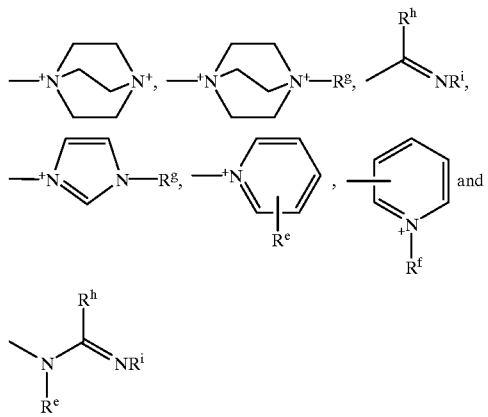

wherein $R^e$, $R^f$, $R^g$ and $R^h$ are the same or differrent, and each represent a hydrogen atom, a lower alkyl group, a cyclo-lower alkyl group, a lower alkenyl group, a lower alkynyl group, an aryl group, an aromatic heterocyclic group selected from thiazolyl, isothiazolyl, oxazolyl, isoxazolyl, pyrazolyl, imidazolyl, triazolyl, pyridyl, pyrimidinyl, pyrazinyl, quinolinyl, isoquinolinyl, benzothiazolyl, benzoxazolyl, benzopyrazolyl, quinoxalinyl, benzimidazolyl, benzotriazolyl, thiadiazolyl, thienyl, furyl and tetrazolyl groups, or a non-aromatic heterocyclic group selected from

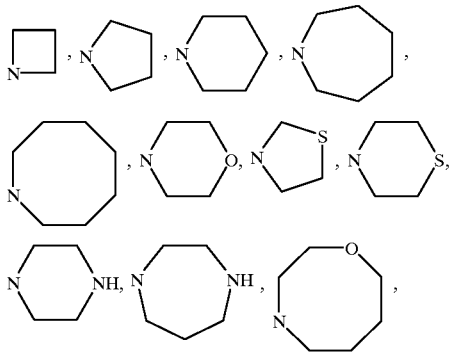

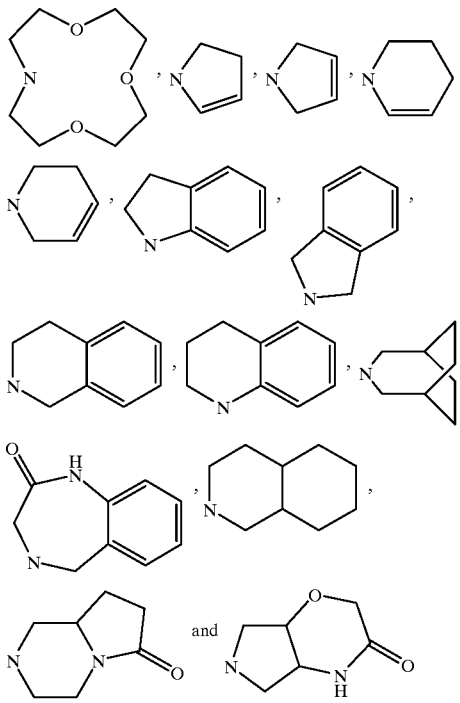

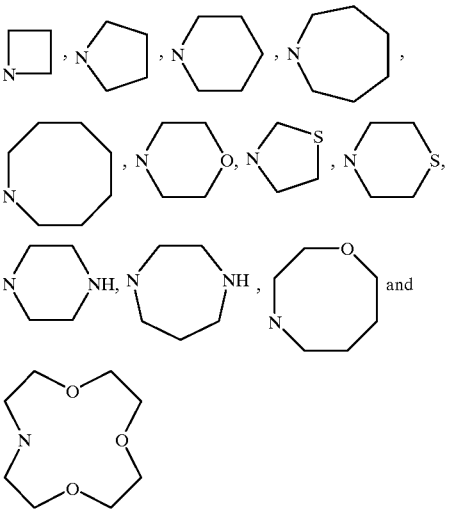

$R^i$ represents a hydrogen atom, a lower alkyl group or a cyclo-lower alkyl group, optionally substituted lower alkyl groups, optionally substituted lower alkenyl groups, and optionally substituted lower alkynyl groups, wherein the substituent(s) in the optionally substituted lower alkyl groups, optionally substituted lower alkenyl groups and optionally substituted lower alkynyl groups can be selected from a hydroxyl group, a methoxy group, an amino group, a nitro group, a cyano group, a carbamoyl group, a carbamoyloxy group, a formyl group, a hydrazylcarbonyloxy group, a sulfamoyl group, a trifluoromethyl group, a carboxyl group and a sulfo group, X represents a single bond, an oxygen atom, a sulfur atom, a sulfinyl group, a sulfonyl group, $NR^6$, $SO_2NR^6$, $N(R^6)SO_2NR^7$, $N(R^6)SO_2$, $CH(OR^6)$, $CONR^6$, $N(R^6)CO$, $N(R^6)CONR^7$, $N(R^6)COO$, $N(R^6)CSO$, $N(R^6)COS$, $C(R^6)=CR^7$, $C\equiv C$, $CO$, $CS$, $OC(O)$, $OC(O)NR^6$, $OC(S)NR^6$, $SC(O)$, $SC(O)NR^6$ or $C(O)O$ wherein $R^6$ and $R^7$ each represent a hydrogen atom or an optionally substituted lower alkyl group wherein the substituent(s) in the optionally substituted lower alkyl group can be selected from a hydroxyl group, a methoxy group, an amino group, a nitro group, a cyano group, a carbamoyl group, a carbamoyloxy group, a formyl group, a hydrazylcarbonyloxy group, a sulfamoyl group, a trifluoromethyl group, a carboxyl group and a sulfo group, and m and n are the same or different and each represent an integer of 0 to 10, or $R^3$ and $R^1$ are combined together with the nitrogen atom to which they bound to form a heterocyclic group selected from the following groups (a)

wherein each of the groups may have substituent(s) selected from lower alkyl groups, a hydroxyl group, lower alkoxy groups, hydroxy-lower alkyl groups, a carboxyl 1group, a carbamoyl group, N-lower alkylcarbamoyl groups, N,N-dilower alkylcarbamoyl groups, an amino group, N-lower alkylamino groups, N,N-dilower alkylamino groups, N,N,N-trilower alkylammmonio groups, amino-lower alkyl groups, N-lower alkylamino-lower alkyl groups, N,N-dilower alkylamino-lower alkyl groups, N,N,N-trilower alkylammmonio-lower alkyl groups, groups, lower alkanoylamino groups, aroylamino groups, lower alkylsulfonylamino groups, lower alkylthio-lower alkyl groups, lower alkylsulfonyl-lower alkyl groups, lower alkylsulfinyl-lower alkyl groups, a hydroxyimino group, lower alkoxyimino group, an oxogroup, a formyl group, lower alkanoyl groups, carbamoyl-lower alkylcarbonyl groups, amino-lower alkylcarbonyl groups, carboxy-lower alkylcarbonyl groups, N-lower alkylamino-lower alkylcarbonyl groups, N,N-dilower alkylamino-lower alkylcarbonyl groups, N,N,N-trilower alkylammonio-lower alkylcarbonyl groups, hydroxy-lower alkylcarbonyl groups, and groups:

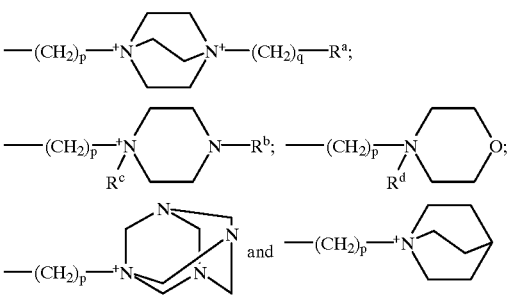

wherein $R^a$ represents a hydroxyl group or a carbamoyl group, $R^b$ represents a lower alkyl group, a formyl group or a lower alkanoyl group, $R^c$ and $R^d$ are the same or different and each represent a lower alkyl group, and p and q are the same or different and each represent 0 to 4, (b)

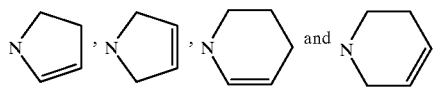

wherein each of the groups may have substituent(s) selected from halogen atoms, lower alkoxy groups, lower alkyl groups, a carbamoyl group, carbamoyl-lower alkyl groups, amino-lower alkyl groups, N-lower alkylamino-lower alkyl groups, N,N-dilower alkylamino-lower alkyl groups, N,N,N-trilower alkylammonio-lower alkyl groups, pyridinio-lower alkyl groups, hydroxy-lower alkyl groups, groups:

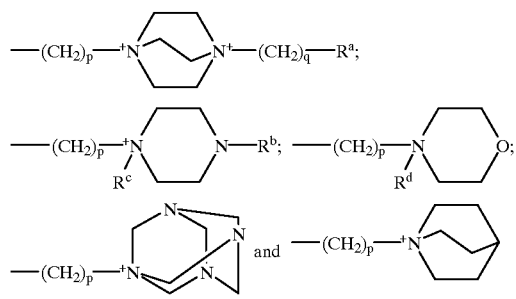

wherein $R^a$ represents a hydroxyl group or a carbamoyl group, $R^b$ represents a lower alkyl group, a formyl group or a lower alkanoyl group, $R^c$ and $R^d$ are the same or different and each represent a lower alkyl group, and p and q are the same or different and each represent 0 to 4, (c)

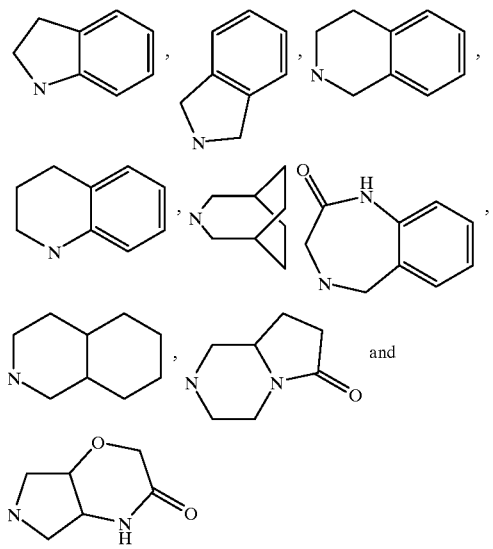

wherein each of the groups may have substituent(s) selected from halogen atoms, lower alkoxy groups, lower alkyl groups, a carbamoyl group, carbamoyl-lower alkyl groups, amino-lower alkyl groups, N-lower alkylamino-lower alkyl groups, N,N-dilower alkylamino-lower alkyl groups, N,N,N-trilower alkylammonio-lower alkyl groups, pyridinio-lower alkyl groups, hydroxy-lower alkyl groups, groups:

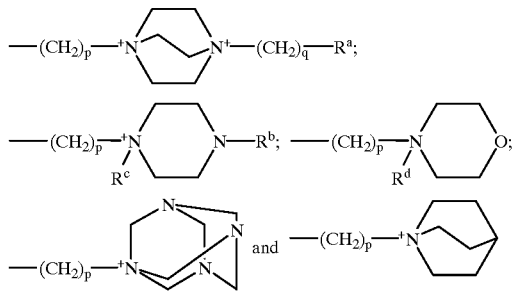

wherein $R^a$ represents a hydroxyl group or a carbamoyl group, $R^b$ represents a lower alkyl group, a formyl group or a lower alkanoyl group, $R^c$ and $R^d$ are the same or different and each represent a lower alkyl group, and p and q are the same or different and each represent 0 to 4, and (d)

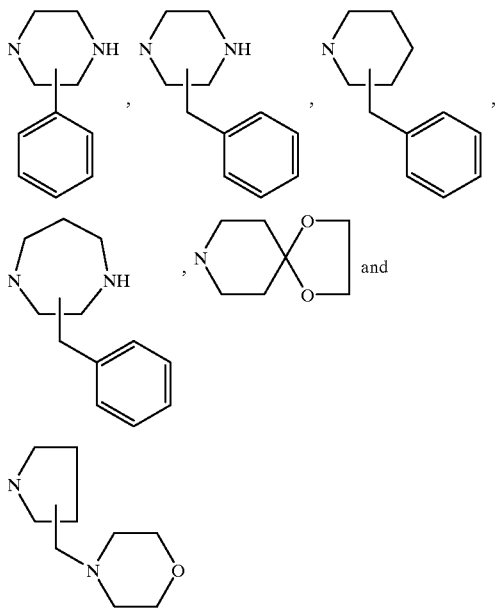

wherein each of the groups may have substituent(s) selected from lower alkyl groups, a hydroxyl group, hydroxy-lower alkyl groups, a carbamoyl group, N-lower alkylcarbamoyl groups, N,N-dilower alkylcarbamoyl groups, an amino group, N-lower alkylamino groups, N,N-dilower alkylamino groups, N,N,N-trilower alkylammmonio groups, amino-lower alkyl groups, N-lower alkylamino-lower alkyl groups, lower alkanoylamino groups, aroylamino groups, and lower alkylsulfonylamino groups, provided that when R is negetive charge, the compound has quaternary ammonium group(s), and these quaternary ammonium group(s) are neutralized with the negative charge of $R^2$ or with the negative charge of $R^2$ and another counter anion selected from the group consisting of an inorganic anion and an organic anion.

2. The compound according to claim 1 wherein $R^5$ represents the same $R^5$ as in claim 1 except that the hydrogen atom, the lower alkynyl group and the polycyclic group are excluded, X represents the same x as in claim 1 except that $N(R^6)CSO$, $N(R^6)COS$, $C(R^6)=CR^7$, $C{\equiv}C$, CO, CS, OC(O), $OC(O)NR^6$, $OC(S)NR^6$, SC(O), $SC(O)NR^6$ and C(O)O are excluded, and m and n each are an integer of 0 to 4.

3. An antibacterial agent comprising a compound according to claim 1 together with a pharmaceutical carrier.

* * * * *